United States Patent
Linask

(10) Patent No.: US 8,883,744 B2
(45) Date of Patent: Nov. 11, 2014

(54) METHOD AND COMPOSITION FOR MODULATING CANONICAL WNT PATHWAY USING FOLATE AND INOSITOL

(71) Applicant: Kersti K. Linask, Clearwater, FL (US)

(72) Inventor: Kersti K. Linask, Clearwater, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/048,824

(22) Filed: Oct. 8, 2013

(65) Prior Publication Data

US 2014/0094467 A1   Apr. 3, 2014

Related U.S. Application Data

(63) Continuation of application No. 13/226,096, filed on Sep. 6, 2011, now abandoned, which is a continuation of application No. PCT/US2010/026374, filed on Mar. 5, 2010.

(60) Provisional application No. 61/157,633, filed on Mar. 5, 2009.

(51) Int. Cl.

| A61K 31/70 | (2006.01) |
| A61K 31/519 | (2006.01) |
| A61K 31/047 | (2006.01) |
| A61K 9/08 | (2006.01) |
| A61K 9/00 | (2006.01) |

(52) U.S. Cl.
CPC .............. *A61K 31/047* (2013.01); *A61K 31/70* (2013.01); *A61K 9/08* (2013.01); *A61K 9/0014* (2013.01); *A61K 31/519* (2013.01)
USPC .......................................... 514/23; 514/249

(58) Field of Classification Search
USPC .................................................. 514/23, 249
See application file for complete search history.

(56) References Cited

U.S. PATENT DOCUMENTS

| 5,658,594 A | 8/1997 | Al-Hassan |
| 5,661,132 A | 8/1997 | Eriksson et al. |
| 2004/0043013 A1 | 3/2004 | McCleary |
| 2004/0171559 A1 | 9/2004 | Weissman et al. |
| 2004/0234626 A1 | 11/2004 | Gardiner et al. |
| 2008/0075714 A1 | 3/2008 | Lee et al. |

FOREIGN PATENT DOCUMENTS

DE   19627627 A1 * 1/1998

OTHER PUBLICATIONS

Gaereskog et al. (Teratology (2006), 76(6), 483-490) (Abstract sent).*
Hod et al. (Israel journal of medical sciences, (Oct. 1990) vol. 26, No. 10, pp. 541-544) (Abstract sent).*
Berndt, Heinz; DE 19627627 A1; Jan. 22, 1998 (English Machine Translation).*
STN abstract of Berndt, Heinz; DE 19627627 AI Jan. 22, 1998 (Abstract sent).*
Gaereskog et al. (Teratology (2006), 76(6), 483-490).*
Hod et al. (Israel journal of medical sciences, (Oct. 1990) vol. 26, No. 10, pp. 541-544).*
Ionescu-Ittu R, Marelli A, Mackie AS, Pilote L. Prevalence of severe congenital heart disease after folic acid fortification of grain products: time trend analysis in Quebec, Canada. BMJ 2009;338:b1673.
/Datta S, Turner D, Singh R, Ruest LB, Pierce WM, Jr., Knudsen TB. Fetal alcohol syndrome (FAS) in C57BL/6 mice detected through proteomics screening of the amniotic fluid. Birth Defects Res A Clin Mol Teratol 2008;82:177-186.
De Lange FJ, Moorman AF, Anderson RH, et al. Lineage and morphogenetic analysis of the cardiac valves. Circ Res 2004;95:645-654.
Grewal J, Carmichael SL, Ma C, Lammer EJ, Shaw GM. Maternal periconceptional smoking and alcohol consumption and risk for select congenital anomalies. Birth Defects Res A Clin Mol Teratol 2008;82:519-526.
Heusner AA. What does the power function reveal about structure and function in animals of different size? Ann. Rev. Physiol. 1987;49:121-133.
Kirby ML, Lawson A, Stadt H, et al. Hensen's node gives rise to the ventral midline of the foregut: implications for organizing head and heart development. Dev Biol 2003;253:175-188.
Kotch L, Sulik K. Patterns of ethanol-induced cell death in the developing nervous system of mice: neural fold states through the time of anterior neural tube closure. Int J Dev Neurosci 1992;10:273-279.
Kwon C, Cordes KR, Srivastava D. Wnt/beta-catenin signaling acts at multiple developmental stages to promote mammalian cardiogenesis. Cell Cycle 2008;7:3815-3818.
Liu Z, Li T, Liu Y, et al. WNT signaling promotes Nkx2.5 expression and early cardiomyogenesis via downregulation of Hdac1. Biochim Biophys Acta 2009;1793:300-311.
Lo CM, Buxton DB, Chua GC, Dembo M, Adelstein RS, Wang YL. 2004. Nonmuscle myosin IIb is involved in the guidance of fibroblast migration. Mol Biol Cell 15:982-989.

(Continued)

*Primary Examiner* — Shaojia Anna Jiang
*Assistant Examiner* — Michael C Henry
(74) *Attorney, Agent, or Firm* — Michele L. Lawson; Smith & Hopen, P.A.

(57) ABSTRACT

The canonical Wnt signaling pathway is implicated in many disorders including neural tube defects, limb malformations, and heart defects, developmental disorders associated with alcohol exposure (fetal alcohol syndrome) or exposure to bipolar medications (i.e. lithium), wound healing, and Alzheimer's disease. Elevated plasma homocysteine (HCy), which results from folate (folic acid, FA) deficiency, the mood-stabilizing drug lithium (Li), and alcohol (ethanol) are linked to the induction of human congenital heart and neural tube defects. FA supplementation ameliorates the observed developmental errors in the Li-HCy, or alcohol-exposed mouse embryos and normalized heart function. Li, HCy or Wnt3A suppress Wnt-modulated Hex and Islet-1 expression. FA protects from the gene misexpression that is induced by all three factors. Administration of myo-inositol with FA synergistically enhances the protective effect.

13 Claims, 24 Drawing Sheets

(56) References Cited

OTHER PUBLICATIONS

Marvin MJ, Di Rocco G, Gardiner A, Bush SM, Lassar AB. Inhibition of Wnt activity induces heart formation from posterior mesoderm. Genes Dev 2001;15:316-327.

Memon S, Pratten MK. Developmental toxicity of ethanol in chick heart in ovo and in micromass culture can be prevented by addition of vitamin C and folic acid. Reprod. Toxicol. 2009;28:262-269.

Pandey SC, Ugale R, Zhang H, Tang L, Prakash A. Brain chromatin remodeling: a novel mechanism of alcoholism. J Neurosci 2008;28:3729-3737.

Yamaguchi TP. Heads or tails: wnts and anterior-posterior patterning. Current Biology 2001;11:R713-R724.

Sonderegger S, Husslein H, Leisser C, Knofler M. Complex expression pattern of Wnt ligands and frizzled receptors in human placenta and its trophoblast subtypes. Placenta 2007;28 Suppl A:S97-S102.

Yeh CH, Chang JK, Wang YH, Ho ML, Wang GJ. Ethanol may suppress Wnt/beta-catenin Signaling on human bone marrow stroma cells. Clin Orthop. Relat Res. 2008;466:1047-1053.

Soshnikova N, Duboule D. Epigenetic temporal control of mouse Hox genes in vivo. Science 2009;324:1320-1323.

Verzi MP, McCulley DJ, De Val S, Dodou E, Black BL. The right ventricle, outflow tract, and ventricular septum comprise a restricted expression domain within the secondary/anterior heart field. Dev Biol 2005;287:134-145.

Webster W, Walsho D, McEwen S, Lipson A. Some teratogenic properties of ethanol and acetaldehyde in C57BL/6J mice: implications for the study of the fetal alcohol syndrome. Teratology 1983;27:231-243.

Wang J, Alexander P, Wu L, Hammer R, Cleaver O, McKnight SL. Dependence of mouse embryonic stem cells on threonine catabolism. Science 2009;325:435-439.

Armstrong EJ, Bischoff J. Heart valve development: endothelial cell signaling and differentiation. Circ Res 2004;95:459-470.

Czeizel AE, Timar, L., Sarkozi, A. Dose-dependent effect of folic acid on the prevention of orofacial clefts. Pediatrics 1999;104:e66.

Bailey LB. Folate and vitamin B12 recommended intakes and status in the United States. Nutr Rev 2004;62:S14-20.

Dasgupta et al., 1999 Multiple roles for activated LEF/TCF transcription complexes during hair follicle development and differentiation. Development 126, 4557-4568.

Bailey B, Sokol R. Pregnancy and alcohol use: Evidence and recommendations for prenatal care. Clin Obstet Gynecol 2008;51:436-444.

Butcher JT, Markwald RR. Valvulogenesis: the moving target. Philos Trans R Soc Lond B Biol Sci 2007;362:1489-503.

Cavieres MF, Smith SM. Genetic and developmental modulation of cardiac deficits in prenatal alcohol exposure. Alcohol Clin Exp Res 2000;24:102-109.

Linask KK, Lash JW. 1990. Fibronectin and integrin distribution on migrating precardiac mesoderm cells. Ann. N.Y. Acad. Sci. 588:417-420.

Linask KK, Lash JW. 1988b. A role for fibronectin in the migration of avian precardiac cells. II. Rotation of the heart-forming region during different stages and its effects. Dev. Biol. 129:324-329.

Linask KK, Lash JW. 1988a. A role for fibronectin in the migration of avian precardiac cells. I. Dose dependent effects of fibronectin antibody. Dev. Biol. 129:315-323.

Linask KK, Lash JW. 1986. Precardiac cell migration:Fibronectin localization at mesoderm-endoderm interface during directional movement. Dev. Biol. 114:87-101.

Liu et al., Augmented Wnt signaling in a mammalian model of accelerated aging. Science 2007;317:803-806.

Clevers, Wnt/beta-catenin signaling in development and disease. Cell 2006;127:469-480.

Zhang et al., Folate stimulation of wound DNA synthesis. Journal of Surgical Research 2008;147:15-22.

Brack et al., Increased Wnt signaling during aging alters muscle stem cell fate and increases fibrosis. Science 2007;317:807-810.

Suda et al., Wnt signaling in the niche. Cell 2008; 132:729-730.

Han et al., Folate rescues lithium-, homocysteine- and Wnt3A-induced vertebrate cardiac anomalies. Disease Models & Mechanisms 2009;2:467-478.

Human genetic diseases and Wnt signaling components, http:www.stanford.edu/~rnusse/diseases/Humangeneticdis.htm accessed Feb. 25, 2009.

Linask KK, Tsuda T. Application of plastic embedding for sectioning whole-mount immunostained early vertebrate embryos. Methods Mol Biol, vol. 135, Developmental Biology Protocols, vol. 1, 2000;135:165-173.

Linask KK, Huhta JC. Use of doppler echocardiography to monitor embryonic mouse heart function. Methods Mol Biol, vol. 135, Developmental Biology Protocols 2000;1:245-252.

Cohen, L. S., Friedman, J. M., Jefferson, J. W., Johnson, E. M. and Weiner, M. L. A reevaluation of risk of in utero exposure to lithium. Jama 1994;271: 146-150.

Stojadinovic et al., Molecular Pathogenesis of Chronic Wounds, The Role of Beta-Catenin and c-myc in the Inhibition of Epithelialization and Wound Healing, American Journal of Pathology, 2005;167(1), 59-69.

Seifert et al., The Avian Prechordal Head Region: a Morphological Study, J. Anat. 1993;183: 75-89.

Huhta et al., Recent Advances in the Prevention of Congenital Heart Disease, Current Opinion in Pediatrics 2006;18: 484-489.

Anderson et al., Development of the Heart: (3) Formation of the Ventricular Outflow Tracts, Arterial Valves, and Intrapericardial Arterial Trunks, Heart 2003;89: 1110-1118.

Gould et al., Glycogen Synthase Kinase-3: a Putative Molecular Target for Lithium Mimetic Drugs, Neuropsychopharmacology 2005; 30: 1223-1237.

De La Cruz et al., The Primitive Cardiac Regions in the Straight Tube Heart (Stage9-) and Their Anatomical Expression in the Mature Heart: and Experimental Study in the Chick Embryo, J. Anat. 1989;165: 121-131.

Rosenquist et al., Genes, Folate and Homocysteine in Embryonic Development, Proceedings of the Nutrition Society, 2001;60: 53-61.

Smithberg et al., Teratogenic Effects of Lithium in Mice, Teratology 1982;26: 239-246.

International Search Report for PCT/US2010/026374, dated Nov. 11, 2010.

Wohrle, S., Wallmen, B. and Hecht, A. (2007). Differential control of Wnt target genes involves epigenetic mechanisms and selective promoter occupancy by T-cell factors. Mol Cell Biol 27, 8164-77.

Williams, K. T. and Schalinske, K. L. (2007). New insights into the regulation of methyl group and homocysteine metabolism. J Nutr 137, 311-314.

Zhang, F., Phiel, C., Spece, L., Gurvich, N. and Klein, P. (2003). Inhibitory phosphorylation of glycogen synthase kinase-3 (GSK-3) in response to lithium. J Biol. Chem. 278, 33067-33077.

Yu, W. McDonnell, K., Taketo, M. M. and Bai, C. B. (2008). Wnt signaling determines ventral spinal cord cell fates in a time-dependent manner. Development 135, 3687-3696.

Sierra, J., Yoshida, T., Joazeiro, C. A. and Jones, K. A. (2006). The APC tumor suppressor counteracts beta-catenin activation and H3K4 methylation at Wnt target genes. Genes Dev 20, 586-600.

Ochi, H., Matsubara, K., Kusanagi, Y., Furutani, K., Katayama, T. and Ito, M. (1999). The influence of the maternal heart rate on the uterine artery pulsatility index in the pregnant ewe. Gynecol. Obstet. Invest. 47, 73-75.

Schou, M., Weinstein, M. R. and Villeneuve, A. (1973). Lithium and pregnancy. I. Report from the Register of Lithium Babies. Br. Med. J. 2, 135-136.

Morrison, J. L., Botting, K. J., Dyer, J. L., Williams, S. J., Thornburg, K. L. and McMillen. (2007). Restriction of placental function alters heart development in the sheep fetus. Am J. Physiol. Integr Comp. Physiol 293, R306-R313.

Rosenquist, T. H., Ratashak, S. A. and Selhub, J. (1996). Homocysteine induces congenital defects of the heart and neural tube: effect of folic acid. Proc Natl Acad Sci U S A 93, 15227-15232.

(56) References Cited

OTHER PUBLICATIONS

Mohamed, O. A., Jonnaert, M., Labelle-Dumais, C., Kuroda, K., Clarke, H. J. and Dufort, D. (2005). Uterine Wnt/beta-catenin signaling is required for implantation. Proc Natl Acad Sci., USA 102, 8579-8584.

Rakyan, V. K., Chong, S., Champ, M. E., Cuthbert, P. C., Morgan, H. D. and Luu, K. V. (2003). Transgenerational inheritance of epigenetic states at the murine Axin (Fu) allele occurs after maternal and paternal transmission. Proc Natl Acad Sci U S A 100, 2538-2543.

Manisastry, S. M., Han, M. and Linask, K. K. (2006). Early temporal-specific responses and differential sensitivity to lithium and Wnt-3A exposure during heart development. Dev Dyn 235, 2160-2174.

Schmidt, C., McGonnell, I., Allen, S. and Patel, K. (2008). The role of Wnt signalling in the development of somites and neural crest. Adv Anat Embryol Cell Biol 195, 1-64.

Willert, K. and Jones, K. (2006). Wnt signaling: is the party in the nucleus? Genes Dev 20, 1394-1404.

Ulloa, F. and Briscoe, J. (2007). Morphogens and the control of cell proliferation and patterning in the spinal cord. Cell Cycle 6, 2640-2649.

Ueno, S., Weidinger, G., Osugi, T., Kohn, A. D., Golob, J. L., Pabon, L., Reinecke, H., Moon, R. T. and Murry, C. E. (2007). Biphasic role for Wnt/beta-catenin signaling in cardiac specification in zebrafish and embryonic stem cells. Proc Natl Acad Sci U S A 104, 9685-9690.

Tang, L. S., Wlodarczyk, B. J., Santillano, D. R., Miranda, R. C. and Finnell, R. H. (2004). Developmental consequences of abnormal folate transport during murine heart morphogenesis. Birth Defects Res A Clin Mol Teratol 70, 449-458.

Spiegelstein, O., Mitchell, L. E., Merriweather, M. Y., Wicker, N. J., Zhang, Q., Lammer, E. J. and Finnell, R. H. (2004). Embryonic development of folate binding protein-1 (Folbp1) knockout mice: Effects of the chemical form, dose, and timing of maternal folate supplementation. Dev Dyn 231, 221-231.

Snarr, B. S., Wirrig, E. E., Phelps, A. L., Trusk, T. C. and Wessels, A. (2007). A spatiotemporal evaluation of the contribution of the dorsal mesenchymal protrusion to cardiac development. Dev Dyn 236, 1287-1294.

Zhu, H., Wlodarczyk, B. J., Scott, M., Yu, W., Merriweather, M., Gelineau-van Waes, J., Schwartz, R. J. and Finnell, R. H. (2007). Cardiovascular abnormalities in Folr1 knockout mice and folate rescue. Birth Defects Res A Clin Mol Teratol 79, 257-268.

Yonkers, K. A., Stowe, Z., Leibenluft, E., Cohen, L., Miller, L., Manber, R., Viguera, A., Suppes, T. and Altshuler, L. (2004). Management of bipolar disorder during pregnancy and the postpartum period. Am. J. Psychiatry 161, 608-620.

Linask, K. K., Knudsen, K. A. and Gui, Y. H. (1997). N-Cadherin-Catenin Interaction: Necessary component of cardiac cell compartmentalization during early vertebrate heart development. Dev. Biol. 185, 148-164.

Liu, Z., Choi, S. W., Crott, J. W., Keyes, M. K., Jang, H., Smith, D. E., Kim, M., Laird, P. W., Bronson, R. and Mason, J. B. (2007). Mild depletion of dietary folate combined with other B vitamins alters multiple components of the Wnt pathway in mouse colon. J. Nutr. 137, 2701-2708.

Linask, K. K., Han, M. D., Artman, M. and Ludwig, C. A. (2001). Sodium-calcium exchanger (NCX-1) and calcium modulation. NCX protein expression patterns and regulation of early heart development. Dev. Dynamics 221, 249-264.

Lin, L., Cui, L., Zhou, W., Dufort, D., Zhang, X., Cai, C. L., Bu, L., Yang, L., Martin, J., Kemler, R. et al. (2007). Beta-catenin directly regulates Islet1 expression in cardiovascular progenitors and is required for multiple aspects of cardiogenesis. Proc Natl Acad Sci U S A 104, 9313-9318.

Louvi, A., Yoshida, M. and Gorve, E. A. (2007). The derivatives of the Wnt3a lineage in the central nervous system. J Comp Neurol 504, 550-569.

Kamudhamas, A., Pang, L., Smith, S. D., Sadovsky, Y. and Nelson, D. M. (2004). Homocysteine thiolactone induces apoptosis in cultured human trophoblasts: A mechanism for homocysteine-mediated placental dysfunction. Am J. Obstet. Gynecol. 191, 563-571.

Jacobson, S., Ceolin, L., Kaur, P., Pastuszak, A., Einarson, T., Koren, G., Jones, K., Johnson, K. S., D., Donnenfeld, A. E., Rieder, M. and Santelli, R. (1992). Prospective multicentre study of pregnancy outcome after lithium exposure during first trimester. Lancet 330, 530-533.

Kwon, C., Arnold, J., Hsiao, E. C., Taketo, M. M., Conklin, B. R. and Srivastava, D. (2007). Canonical Wnt signaling is a positive regulator of mammalian cardiac progenitors. Proc Natl Acad Sci., USa 104, 10894-10899.

Iqbal, M. and Mahmud, S. (2001). The effects of lithium, valproic acid, and carbamazepine during pregnancy and lactation. J. Toxicol. Clini Toxicol. 39, 381-392.

Klein, P. S. and Melton, D. A. (1996). A molecular mechanism for the effect of lithium on development. Proc. Natl. Acad. Sci. U.S.A. 93, 8455-8459.

Hurlstone, A. F., Haramis, A. P., Wienholds, E., Begthel, H., Korving, J., Van Eeden, F., Cuppen, E., Zivkovic, D., Plasterk, R. H. and Clevers, H. (2003). The Wnt/beta-catenin pathway regulates cardiac valve formation. Nature 425, 633-637.

Hamburger, V. and Hamilton, H. L. (1951). A series of normal stages in the development of the chick embryo. J. Morphol. 88, 49-92.

Foley, A. C. and Mercola, M. (2005). Heart induction by Wnt antagonists depends on the homeodomain transcription factor Hex. Genes Dev 19, 387-396.

Gui, Y. H., Linask, K. K., Khowsathit, P. and Huhta, J. C. (1996). Doppler Echocardiography of Normal and Abnormal Embryonic Mouse Heart. Ped. Res. 40, 633-642.

Foley, A. and Mercola, M. (2004). Heart induction: embryology to cardiomyocyte regeneration. Trends Cardiovasc Med 14, 121-125.

Garcia-Castro, M. I., Marcelle, C. and Bronner-Fraser, M. (2002). Ectodermal Wnt function as a neural crest inducer. Science 297, 848-851.

Ernest, S., Carter, M., Shao, H., Hosack, A., Lerner, N., Colmenares, C., Rosenblatt, D. S., Pao, Y. H., Ross, M. E. and Nadeau, J. H. (2006). Parallel changes in metabolite and expression profiles in crooked-tail mutant and folate-reduced wild-type mice. Hum Mol Genet 15, 3387-3393.

Gao, Y. and Wang, H. Y. (2007). Inositol pentakisphosphate mediates Wnt/beta-catenin signaling. J. Biol. Chem 282, 26490-26502.

Darnell, D. K. and Schoenwolf, G. C. (2000). Culture of Avian Embryos. In Developmental Biology Protocols, vol. 1 (ed. R. S. Tuan and C. W. Lo), pp. 31-38. Totowa, NJ: Humana Press.

Csepregi, A., Rocken, C., Hoffmann, J., Gu, P., Saliger, S., Muller, O., Schneider-Stock, R., Kutzner, N., Roessner, A., Malfertheiner, P. et al. (2008). APC promoter methylation and protein expression in hepatocellular carcinoma. J Cancer Res Clin Oncol. 134, 579-589.

Cai, C. L., Liang, X., Shi, Y., Chi, P. H., Pfaff, S. L., Chen, J. and Evans, S. (2003). Isl1 identified a cardiac progenitor population that proliferates prior to differentiation and contributes a majority of cells to the heart. Dev Cell 5, 877-889.

Chen, J., Han, M., Manisastry, S. M., Trotta, P., Serrano, M. C., Huhta, J. C. and Linask, K. K. (2008). Molecular effects of lithium exposure during mouse and chick gastrulation and subsequent valve dysmorphogenesis. Birth Defects Res A Clin Mol Teratol 82, 508-518.

Cohen, E. D., Wang, Z., Lepore, J. J., Lu, M. M., Tekato, M. M., Epstein, D. J. and Morrisey, E. E. (2007). Wnt/beta-catenin signaling promotes expansion of Isl-1-positive cardiac progenitor cells through regulation of FGF signaling. J Clin Invest 117, 1794-804.

Corstius, H., Zimanyi, M. A., Maka, N., Herath, T., Thomas, W., Van der Laarse, A., Wreford, N. G. and M.J., B. (2005). Effect of intrauterine growth restriction on the number of cardiomyocytes in rat hearts. Pediatr Res 57, 796-800.

Boot, M. J., Steegers-Theunissen, R. P., Poelmann, R. E., van Iperen, L. and Gittenberger-de Grooth, A. C. (2004). Cardiac outflow tract malformations in chick embryos exposed to homocysteine. Cardiovasc Res 64, 365-373.

Belmaker, R. H., Agam, G., van Calker, D., Richards, M. H. and Kofman, O. (1998). Behavioral reversal of lithium effects by four inositol isomers correlates perfectly with biochemical effects on the PI cycle. Neuropsychopharmacology 19, 220-232.

(56) References Cited

OTHER PUBLICATIONS

Alvarez-Medina, R., Cayuso, J., Okubo, T., Takada, S. and Marti, E. (2008). Wnt canonical pathway restricts graded Shh/Gli patterning activity through the regulation of Gli3 expression. Development 135, 237-247.

Ai, D., Fu, X., Wang, J., Lu, M. F., Chen, L., Baldini, A., Klein, W. H. and Martin, J. F. (2007). Canonical Wnt signaling functions in second heart field to promote right ventricular growth. Proc Natl Acad Sci U S A 104, 9319-9324.

* cited by examiner

Figure 8A-B

Wnt (2ng) DATA

| St. 3 | Normal | Total | St.4 | Normal | Total |
|---|---|---|---|---|---|
| | 3 | 26 | | 3 | 8 |
| TOTAL | 3 | 26 | TOTAL | 3 | 8 |

| CHART | Normal | Total | Percentage |
|---|---|---|---|
| St.3/4 | 6 | 34 | 17.6 |

C

Wnt (2ng)/ FA (10 ug) DATA

| St. 3 | Normal | Total | St.4 | Normal | Total |
|---|---|---|---|---|---|
| | 15 | 33 | | 10 | 13 |
| TOTAL | 15 | 33 | TOTAL | 10 | 13 |

| CHART | Normal | Total | Percentage |
|---|---|---|---|
| St.3/4 | 25 | 46 | 54.3 |

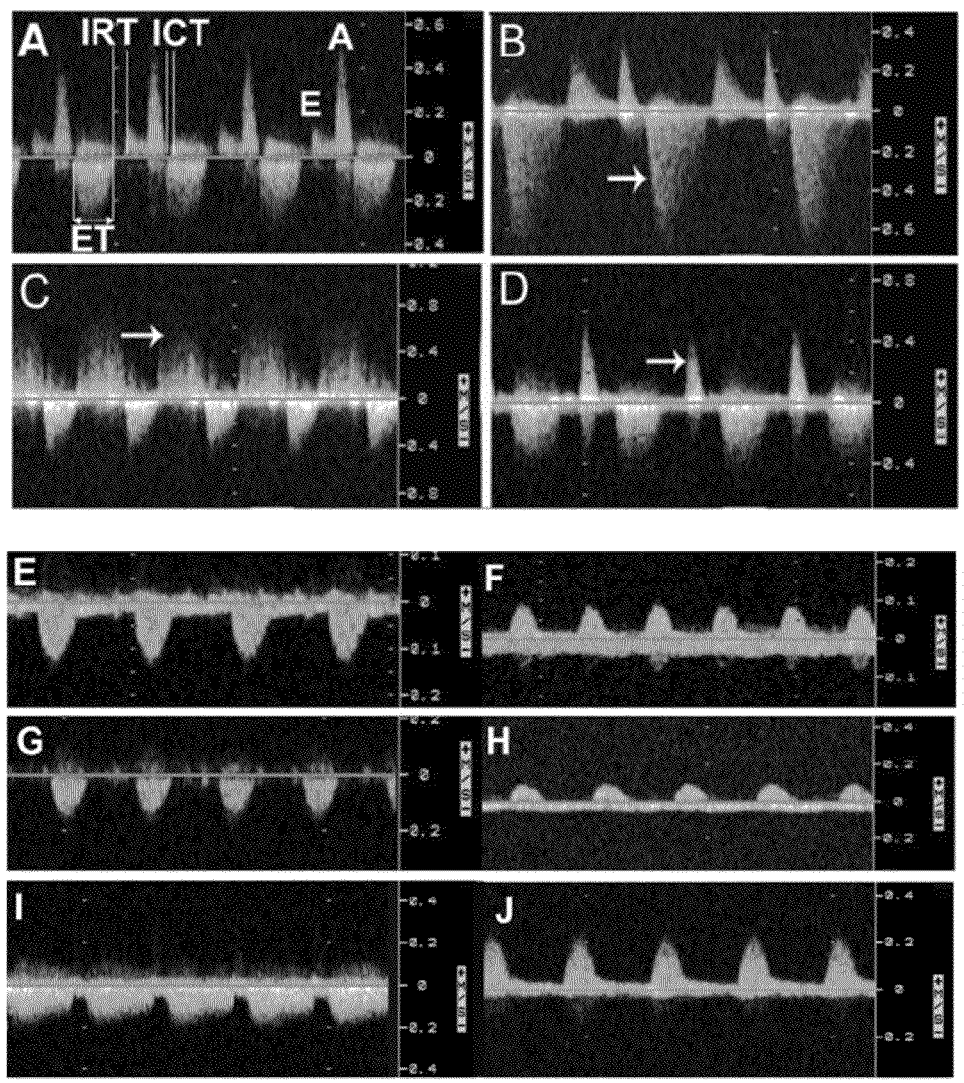
Figure 11A-J

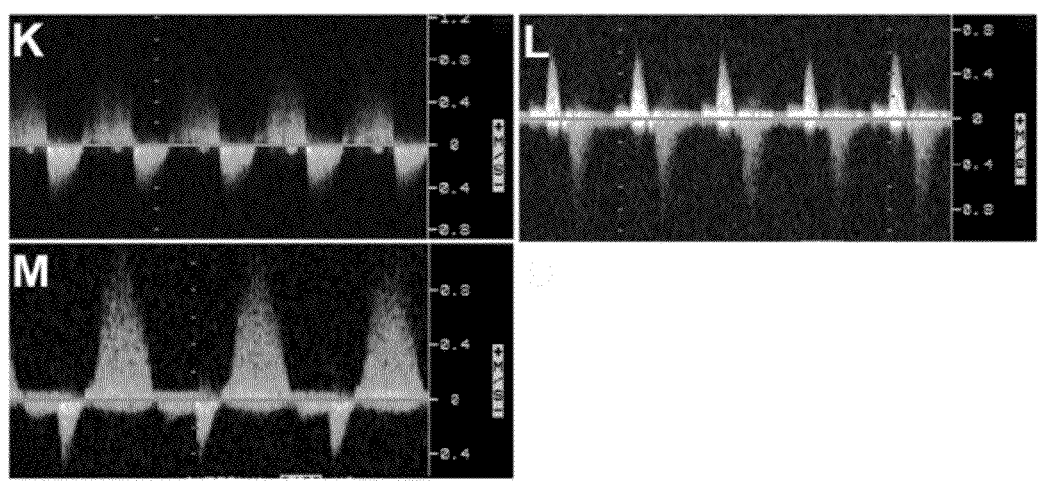
Figure 11K-M

METHOD AND COMPOSITION FOR MODULATING CANONICAL WNT PATHWAY USING FOLATE AND INOSITOL

CROSS REFERENCE TO RELATED APPLICATION

This application is a continuation of and claims priority to currently pending U.S. patent application Ser. No. 13/226,096, entitled "Method and Composition for Modulating Canonical Wnt Pathway Using Folate and inositol", filed Sep. 6, 2011, which is a continuation of and claims priority to International Application, Serial No. PCT/US2010/026374, entitled "Method and Composition for Modulating Canonical Wnt Pathway Using Folate and Inositol", filed Mar. 5, 2010, which claims priority to U.S. Provisional Patent Application No. 61/157,633, entitled "Combination of Folate and Inositol for Altering Wnt Pathway", filed on Mar. 5, 2009, the contents of each of which are herein incorporated by reference.

GOVERNMENT SUPPORT

This invention was made with government support under HL067306 awarded by National Institutes of Health. The government has certain rights in the invention.

FIELD OF THE INVENTION

This invention relates to protein modulation. Specifically, this invention uses the combination of folate and inositol to modulate the canonical Wnt signaling pathway.

BACKGROUND OF THE INVENTION

WNT Signaling

Wnt proteins are characterized by a high number of conserved cysteine residues. Although Wnt proteins carry an N-terminal signal peptide and are secreted, they are relatively insoluble due to a particular protein modification, cysteine palmitoylation, which is essential for Wnt function (Willert et al., 2003). The porcupine gene, which displays homology to acyl-transferases, and its worm homolog mom-1 are believed to encode the enzyme that is responsible for Wnt palmitoylation (Zhai et al., 2004). Other genes that are conserved and are essential for Wnt secretion, named wntless (wls) and evenness interrupted (evi), respectively. These genes encode a seven-pass transmembrane protein that is conserved from worms (mom-3) to man (hWLS).

In the absence of Wls/evi, Wnts are retained inside the cell that produces them. The Wntless protein resides primarily in the Golgi apparatus, where it colocalizes and physically interacts with Wnts. The retromer, a multiprotein complex involved in intracellular trafficking and conserved from yeast to man, is also essential for Wnt secretion and for the generation of a Wnt gradient (Coudreuse et al., 2006). The retromer complex is involved in recycling a Wnt cargo receptor (such as Wntless) between the default secretory pathway and a compartment dedicated to Wnt secretion. Wnt is thought to act as a morphogen (that is, a long range signal whose activity is concentration dependent) (reviewed in Logan and Nusse, 2004). Morphogen action may occur when the palmitoyl moiety constrains movement away from membranes or lipid particles. Thus, Wnts may be tethered to intercellular transport vesicles or lipoprotein particles (Panakova et al., 2005). Alternatively, Wnts may be transported by cytonemes, which are long, thin filopodial processes. Additionally, extracellular heparan sulfate proteoglycans (HSPG) act in the transport or stabilization of Wnt proteins.

Receptors, agonists, and antagonists for Wnts bind Frizzled (Fz) proteins, which are seven-pass transmembrane receptors with an extracellular N-terminal cysteine-rich domain (CRD) (Bhanot et al., 1996). The Wnt-Fz interaction appears promiscuous, in that a single Wnt can bind multiple Frizzled proteins (e.g., Bhanot et al., 1996) and vice versa. In binding Wnt, Fzs cooperate with a single-pass transmembrane molecule of the LRP family known as LRP5 and -6 in vertebrates (Pinson et al., 2000; Tamai et al., 2000). The transport of LRP5/6 to the cell surface is dependent on a chaperone called Mesd in mice (Culi and Mann, 2003; Hsieh et al., 2003). And consistent with a role of the Mesd chaperone in the transport of LRP5/6 transport, mutations in Mesd resemble loss of LRP5/6. Although it has not been formally demonstrated that Wnt molecules form trimeric complexes with LRP5/6 and Frizzled, surface expression of both receptors is required to initiate the Wnt signal.

The secreted Dickkopf (Dick) proteins inhibit Wnt signaling by direct binding to LRP5/6 (Glinka et al., 1998). Through this interaction, Dkk1 crosslinks LRP6 to another class of transmembrane molecules, the Kremens (Mao et al., 2002), thus promoting the internalization and inactivation of LRP6. An unrelated secreted Wnt inhibitor, Wise, also acts by binding to LRP (Itasaki et al., 2003), as does the WISE family member SOST (Li et al., 2005; Semenov et al., 2005).

Canonical Wnt Signaling

Once bound by their cognate ligands, the Fz/LRP coreceptor complex activates the canonical signaling pathway. Fz can physically interact with Dsh, a cytoplasmic protein that functions upstream of β-catenin and the kinase GSK-3. Wnt signaling controls phosphorylation of Dsh (reviewed in Wallingford and Habas, 2005). Recent studies have indicated that the coreceptor LRP5/6 interacts with Axin through five phosphorylated PPP(S/T)P repeats in the cytoplasmic tail of LRP (Davidson et al., 2005; Zeng et al., 2005). Wnts are thought to induce the phosphorylation of the cytoplasmic tail of LRP, thus regulating the docking of Axin. GSK3 phosphorylates the PPP(S/T) P motif, whereas caseine kinase I-γ (CK1γ) phosphorylates multiple motifs close to the GSK3 sites. CK1γ is unique within the CK1 family in that it is anchored in the membrane through C-terminal palmitoylation. Both kinases are essential for signal initiation.

Wnt Target Genes

Loss of components of the Wnt pathway can produce dramatic phenotypes that affect a wide variety of organs and tissues. A popular view equates Wnt signaling with maintenance or activation of stem cells (Reya and Clevers, 2005). It should be realized, however, that Wnt signals ultimately activate transcriptional programs and that there is no intrinsic restriction in the type of biological event that may be controlled by these programs.

Thus, Wnt signals can promote cell proliferation and tissue expansion but also control fate determination or terminal differentiation of postmitotic cells. Sometimes, these disparate events, proliferation and terminal differentiation, can be activated by Wnt in different cell types within the same structure, such as the hair follicle or the intestinal crypt (Reya and Clevers, 2005). Numerous Tcf target genes have been identified in diverse biological systems. These studies tend to focus on target genes involved in cancer, as exemplified by the wide interest in the Wnt target genes cMyc and Cyclin D1.

The Wnt pathway has distinct transcriptional outputs, which are determined by the developmental identity of the responding cell, rather than by the nature of the signal. In other words, the majority of Wnt target genes appear to be cell type specific. It is not clear whether "universal" Wnt/Tcf target genes exist. The best current candidates in vertebrates are Axin2/conductin (Jho et al., 2002) and SP5 (Weidinger et al., 2005). As noted (Logan and Nusse, 2004), Wnt signaling is autoregulated at many levels. The expression of a variety of positive and negative regulators of the pathway, such as Frizzleds, LRP and HSPG, Axin2, and TCF/Lef are all controlled by the β-catenin/TCF complex.

Patterning of the embryo and cell specification events are activated by a few evolutionarily conserved pathways, one of which is the Wnt/β-catenin pathway. These signaling proteins are used repeatedly during development and in diverse regions. The canonical Wnt pathway has been shown to regulate cell fate decisions, cell proliferation, and cell migration in the embryo. Canonical Wnt signaling is important for neural development, neural crest specification and differentiation, and cardiac development. The signals are transduced in a cell-context dependent manner to result in rapid changes in gene transcription. Reported evidence indicates that canonical Wnt signaling during narrow windows has differential effects during cardiac specification and heart development.

Congenital birth defects can arise with embryonic exposure to therapeutic drugs, high levels of normal plasma metabolites, or other environmental factors. Congenital cardiac defects arising from lithium (Li) exposure, a drug used for management of mood disorders, or from elevated plasma homocysteine (HCy) often involve tricuspid, pulmonary or aortic valve defects; a thickened heart wall; and/or defects in the outflow tract. Cardiac abnormalities are accompanied by neural tube defects and craniofacial anomalies that occur through unknown mechanisms. Previous studies failed to define a developmental window of primary susceptibility or any specific pathway(s) that may be targeted. In addition, chronic knockout approaches were unable to determine when early effects may arise. Thus what is needed is a defined developmental window of primary susceptibility as well as the identification of any specific pathways that may be targeted.

SUMMARY OF INVENTION

The inventors have discovered that both HCy and Li target canonical Wnt signaling during the same early developmental window, but this modulation of the pathway occurs at different regulatory levels. The inventors discovered that HCy, Li and Wnt3A, repress the Wnt-β-catenin-modulated genes Hex (also known as Hhex) and Isl1 in the cardiogenic regions. FA restores normal Hex and Isl1 gene expression and protects against the birth defects that are induced by the three factors thus indicating that FA metabolism intersects with canonical Wnt signaling to provide protection. The addition of myo-inositol synergizes with the FA protection following Li exposure.

During human pregnancy, alcohol use is linked to induction of congenital heart defects associated with Fetal Alcohol Syndrome (FAS). EtOH potentiates the Wnt/β-catenin inhibition of early cardiogenesis by suppressing expression of two cardiac inducing molecules, Hex and Isl-1. These genes are normally activated when canonical Wnt signaling is inhibited by Wnt antagonists. There is an intersection between Wnt/β-catenin signaling, EtOH, and folate metabolism. Folate tips the balance toward the differentiated state, which includes formation of the important methyl group donor, S-adenosylmethionine (SAM). Folate supplementation at a high dose, or in combination with myo-inositol, prevents alcohol potentiation of Wnt/β-catenin signaling allowing normal gene activation and cardiogenesis.

The inventors discovered that factors similar to β-catenin involving the canonical Wnt pathway are involved both in the induction of heart defects during early embryonic development as well as in wound healing efficiency. As chronic wound development is similarly associated with enhanced Wnt/β-catenin signaling, administering folic acid and myo-inositol precludes adverse molecular effects during wound healing and enhances the healing process. Specifically, a combination of folate and inositol is effective in suppressing the effects of the nuclear β-catenin presence in the epidermis thus allowing for the acceleration of healing.

The invention includes a method of treating a patient in need thereof with a therapeutically effective combination of folate and inositol. The patient in need is being treated for at least one disorder selected from the group consisting of developmental disorders including neural tube defects, limb malformations, and heart defects, developmental disorders associated with alcohol exposure (fetal alcohol syndrome) or exposure to bipolar medications (i.e. lithium), stem cell development and proliferation, wound healing, cancer, Alzheimer's disease, diabetes and osteoporosis.

The disorder being treated can be a disorder in which there is an elevated level of homocysteine. The disorder can also be a disorder which is caused by the Wnt signaling pathway. The disorder can be caused by exposure to lithium or alcohol. The folate compound that is administered can be folic acid and the inositol compound can be myo-inositol.

Another embodiment includes a method of preventing the formation of a disorder caused by altered Wnt signaling in a patient comprising the step of administering a therapeutically effective combination of folate and inositol.

In alternate embodiments, the disorder is selected from the group consisting of developmental disorders including neural tube defects, limb malformations, and heart defects, developmental disorders associated with alcohol exposure (fetal alcohol syndrome) or exposure to bipolar medications (i.e. lithium), stem cell development and proliferation, wound healing, cancer, Alzheimer's disease, diabetes and osteoporosis.

The invention includes a method of modulating Wnt signaling comprising the step of contacting a target cell with a therapeutically effective combination of folate and inositol.

The invention also includes a composition that is comprised of a folate compound, an inositol compound and a pharmaceutically acceptable carrier.

BRIEF DESCRIPTION OF THE DRAWINGS

For a fuller understanding of the invention, reference should be made to the following detailed description, taken in connection with the accompanying drawings, in which:

FIGS. 11A-M are a series of images showing Doppler velocity waveforms of blood flow on E15.5 during mouse gestation. Inflow is shown above the zero line and outflow below the line. The outflow is the systolic ejection velocity. (A) A normal pattern of blood flow. (B) Holosystolic AV valve regurgitation (arrow), (C) SL valve regurgitation (arrow), and (D) monophasic inflow pattern with merged E and A waves (arrow). E, early ventricular filling; A, late ventricular filling during atrial contraction; ICT, isovolemic contraction time; IRT, isovolemic relaxation time; ET, ejection time. (E-J) Blood flow velocity waveforms obtained from the descending aorta (E,G,I) and umbilical artery (F,H,J) of a control embryo (E,F), a Li-exposed embryo (G,H), and an Hcy-exposed embryo (I,J). The control embryo waveforms show a normal pattern with diastolic flow (E,F), whereas the Li-exposed embryo waveforms show an absence of diastolic flow (G,H). (I,J) Blood flow in the maternal uterine artery (I) and the descending aorta (J) of an HCy-exposed embryo is similar to control animals. (K-M) Doppler velocity waveforms of blood flow on E15.5 after a single exposure to HCy on E6.75. The waveforms show SL valve regurgitation (K), SL valve stenosis (L), and AV valve regurgitation (M). Calculation of Tei index by pulsed-wave Doppler interrogation of inflow and outflow simultaneously. MPI=(ICT+IRT)/ET, where ICT is isovolumic contraction time, IRT is isovolumic relaxation time, and ET is ejection time. E (passive filling) and A (active filling) waves depicting inflow is indicated.

DETAILED DESCRIPTION OF THE PREFERRED EMBODIMENT

Figure 1:
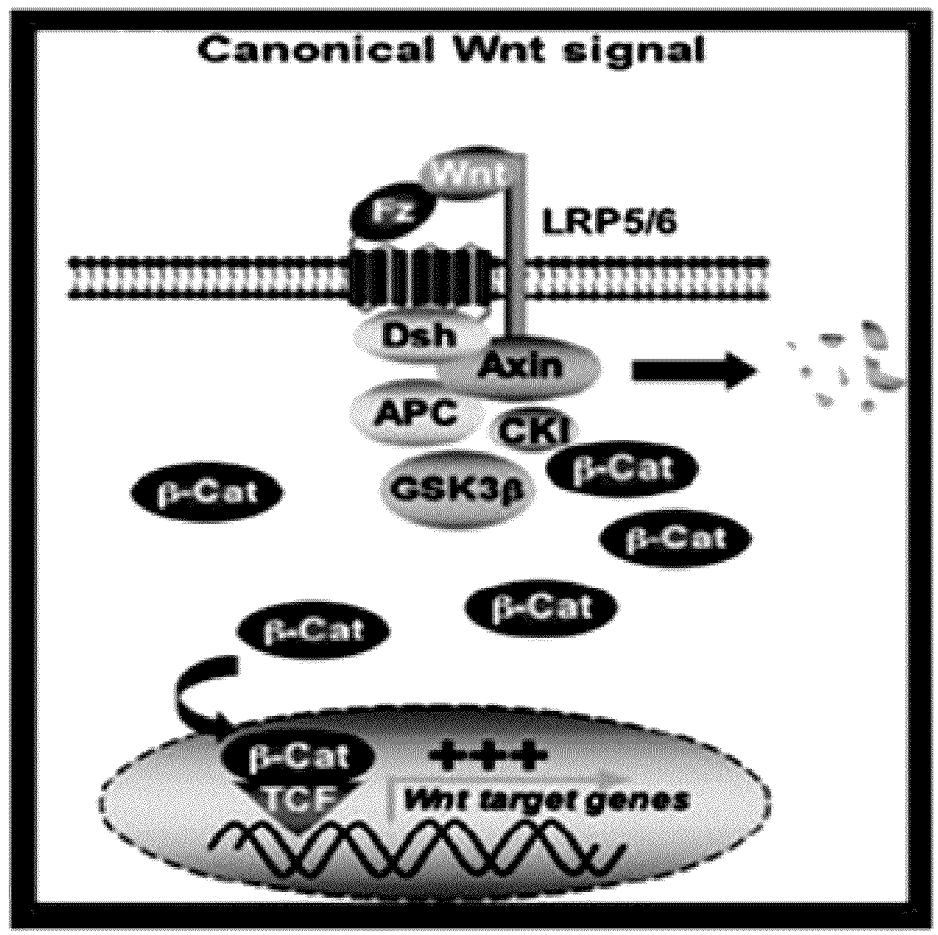
FIG. 1 is an image showing canonical Wnt signaling.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

"Patient" is used to describe an animal, preferably a human, to whom treatment is administered, including prophylactic treatment with the compositions of the present invention.

"Patient at risk therefrom" is used to describe an animal, preferably a human, who exhibits risk factors for potentiation of the Wnt signaling pathway including exposure to lithium, exposure to alcohol, elevated homocysteine levels, folate deficiency, environmental impacts on the folate cycle, mutations in the gene methyltetrafolatereductase or other genes in the folate pathway, modulations of enzymes within the folate pathway such as adenosylmethionine synthase, high levels of nuclear β-catenin and presence of at least one external or internal wound, among others.

"A disorder caused by altered Wnt signaling" is used to describe any disorder that involves the misregulation of the canonical Wnt signaling pathway, including, but not limited to, developmental disorders such as neural tube defects, limb malformations, heart defects, developmental disorders associated with alcohol exposure, lithium exposure, stem cell development and proliferation, wound healing, cancer, Alzheimer's Disease, diabetes and osteoporosis.

"Wnt/β-catenin signaling pathway" is used herein interchangeably with "canonical Wnt signaling pathway".

The "therapeutically effective amount" for purposes herein is thus determined by such considerations as are known in the art. A therapeutically effective amount of a compound or combination of compounds is that amount necessary to provide a therapeutically effective result in vivo. The amount of compound or combination of compounds thereof must be effective to achieve a response, including but not limited to total prevention of (e.g., protection against) and to improved survival rate or more rapid recovery, or improvement (rescue) or elimination of symptoms associated with developmental disorders including neural tube defects, limb malformations, and heart defects, developmental disorders associated with alcohol exposure (fetal alcohol syndrome) or exposure to bipolar- or mood altering medications (i.e. lithium and selective serotonin reuptake inhibitors (SSRIs) including but not limited to paroxetine (Paxil)), stem cell development and proliferation, wound healing, cancer, Alzheimer's disease, diabetes, osteoporosis, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which a compound or combination of compounds of the present invention are delivered to a patient. The composition may be administered in various ways including oral, topical, parenteral (referring to intravenous and intraarterial and other appropriate parenteral routes), intratheceal, intraventricular, intracisternal, intranigral, among others. Each of these conditions may be readily treated using other administration routes of compound or any combination of compounds thereof to treat a disorder or condition.

"Folate", as used herein, is used interchangeably with folic acid (FA) and is meant to include all derivatives thereof.

"Inositol", as used herein, is used interchangeably with myo-inositol and is meant to include all derivatives and isomers thereof.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

Cell specification events and patterning of the embryo are activated by a few evolutionarily conserved pathways, one of which is the Wnt-β-catenin pathway. These signaling proteins are used repeatedly during development and in diverse regions to regulate cell fate decisions, cell proliferation and cell migration in the embryo (Clevers, 2006). Besides cardiac development (Foley and Mercola, 2004; Kwon et al., 2007; Linask et al., 1997; Manisastry et al., 2006; Ueno et al., 2007), canonical Wnt signaling is important for neural development (Alvarez-Medina et al., 2008; Louvi et al., 2007; Ulloa and Briscoe, 2007; Yu et al., 2008) and neural crest specification and differentiation (Garcia-Castro et al., 2002; Schmidt et al., 2008).

Canonical Wnt signaling is initially necessary for normal cardiogenesis, and neurogenesis, but then must be downregulated by Wnt antagonists. The inventors were able to reverse the abnormal situation of maintenance of Wnt signaling that was induced by the environmental factors, and discovered that the administration of FA/myo-inositol did not interfere with the normal signaling. The Wnt antagonist is suppressed by the environmental factors, but its expression is protected by folate/myo-inositol.

Two factors, an elevated level of the metabolic intermediary homocysteine (HCy) and the therapeutic drug lithium (Li), have been a focus of birth defects research for over 30 years. Low dietary folate (FA) and mutations in methylenetetrahydrofolate reductase (MTHFR) lead to elevated maternal plasma HCy levels. Elevated HCy increases the risk for neural tube, neural crest, craniofacial and congenital heart defects in the offspring (Boot et al., 2004; Huhta et al., 2006; Rosenquist et al., 1996; Tang et al., 2004). The association of elevated HCy is particularly strong for specific outflow tract defects, including pulmonary valve stenosis, coarctation of the aorta, and aortic valve stenosis (Huhta et al., 2006). Lithium (Li) is a drug used for bipolar disorder affecting about 2% of women in child bearing age. During human pregnancy, Li has been associated with cardiac teratogenicity in the developing fetus. Recent biochemical, genetic, pharmacological and rodent behavioral studies support the hypothesis that inhibition of glycogen synthase kinase-3 (GSK-3) is the target for lithium's mood-stabilizing properties (Gould and Manji, 2005). In developing embryos GSK-3 is a known intermediary of the canonical Wnt pathway leading to a stabilization of β-catenin that has a role in modulating gene expression (Klein and Melton, 1996) and cell differentiation (Clevers, 2006). β-catenin plays an important role in the formation of the cardiac compartment in the early embryo (Linask, 1992; Linask et al., 1997), suggesting that lithium would affect cardiogenesis via the Wnt signaling pathway. Maternal Li therapy for bipolar disorder, similarly to Hcy, is associated with neural, skeletal, craniofacial, and cardiac valve defects, specifically of the tricuspid valve in association with Ebstein anomaly (Iqbal and Mahmud, 2001; Yonkers et al., 2004). Despite Li and HCy being linked with neural tube and heart defects, the etiology of the induced congenital defects associated with these chemicals has remained unknown.

It was observed that the phenotypic defects induced after a single exposure to Li during gastrulation (Chen et al., 2008) are similar to those reported by others for elevated HCy in a transgenic mouse model (Tang et al., 2004). Because of the similarities in the cardiac and neural anomalies induced by either HCy or Li exposure and because Li is known to mimic Wnt/β-catenin signaling, it was found that both HCy and Li target canonical Wnt signaling during the same early developmental window, but this modulation of the pathway occurs at different regulatory levels.

Clinically Li continues to be considered only a modest risk factor for development of birth defects with first-trimester embryonic exposure (Cohen et al., 1994; Jacobson et al., 1992). Evidence relating peak cardiac defects to an early timing of exposure during vertebrate gastrulation stages (Chen et al., 2008; Manisastry et al., 2006), means that the most susceptible exposure period for heart defects occurs before most women are aware they are pregnant. Moreover, evidence published since the mid-1990s suggests the risk of birth defects arising from Li exposure during early pregnancy is high and can result in early embryonic lethality. This evidence includes: (i) Li mimics canonical Wnt signaling by inhibiting glycogen synthase kinase-3 (GSK-3) (Klein and Melton, 1996; Zhang et al., 2003); (ii) canonical Wnt signaling regulates embryonic cell fate decisions, including of pre-cardiac cells (Ai et al., 2007); (iii) Li and Wnt3A adversely impact cardiogenesis already during gastrulation (Manisastry et al., 2006); (iv) β-catenin functions in defining the cardiac compartment (Linask et al., 1997); (v) β-catenin promotes right ventricular and outflow tract development via Isl1 activation in the second heart field (Lin et al., 2007); and (vi) β-catenin regulates valvulogenesis (Chen et al., 2008; Hurlstone et al., 2003). Based on the aforementioned studies, Li, by its mimicking Wnt/β-catenin signaling, would pose a serious risk to the developing human embryo, specifically in relation to heart development.

The origins of the controversy of Li's effects on cardiogenesis derive from insufficient basic knowledge at the time of the previous investigations of the existence of two heart fields, the first heart field that defines primarily the left ventricle and the second (anterior) heart field that defines part of the right ventricle and outflow tract, and that the timing of their specification coincides with gastrulation (de la Cruz et al., 1989; de la Cruz et al., 1991; Verzi et al., 2005). Li mimics canonical Wnt signaling by inhibiting GSK-3 (Klein and Melton, 1996; Zhang et al., 2003). Li and Wnt3A similarly inhibit cardiogenesis early in development (Manisastry et al., 2006). β-catenin, an important intermediary in canonical Wnt signaling, functions in defining the cardiac compartment (Linask et al., 1997) and promotes right ventricular and outflow tract development via Isl1 activation in the second heart field (Lin et al., 2007) as well as being involved in valvulogenesis (Chen et al., 2008; Hurlstone et al., 2003). Using rodent or avian models, the inventors targeted the embryo during the primitive streak stage. Previous studies exposed the embryo to Li or HCy, after a tubular cardiac structure already was present at E8.0 or later (Nelson et al., 1955; Rosenquist et al., 1996; Smithberg and Dixit, 1982) and thus did not expose embryos at the early time points that the inventors address. Previous studies also failed to define a developmental window of primary susceptibility or any specific pathway(s) that may be targeted. In addition, chronic knockout approaches were unable to determine when early effects may arise.

There is an anterior to posterior progression of heart development and the severity of Li and HCy effects on cardiogenesis decreases with increasing development. When cardiac cells differentiate, they are no longer sensitive to the inhibitory effects of Wnt β-catenin signaling. The inventors have shown in the avian embryonic model that three populations of cells, the neural crest, prechordal plate and cardiac progenitor cells are affected by a potentiation of Wnt signaling by Li during gastrulation (Chen et al., 2008). The prechordal plate cells contribute to valve dysmorphogenesis a week later due to their being inhibited in their migration to the permanent dorsal mesocardial attachment area, also known as the dorsal mesenchymal protrusion, a region important for valve development (Snarr et al., 2007). With Li exposure, the prechordal plate cells populate this important region for valve development in reduced numbers (Chen et al., 2008). With the same timing of exposure, elevated HCy produces similar gene misexpression of two Wnt-modulated genes Hex and Isl-1, as was seen with Li exposure in avian embryos. In addition with mouse embryonic exposure, although not identical, the inventors observed similarities in valve defects induced with both Li and HCy acute exposure by i.p. injection during gastrulation. The results suggested that a common pathway that is modulated by both Li and HCy apparently relates to the dominant Wnt/β-catenin signaling pathway in early cardiac development.

In the avian model, all three of the molecules, that is, HCy, Li and Wnt3A, repress the Wnt-β-catenin-modulated genes Hex (also known as Hhex) and Isl1 in the cardiogenic regions. FA restores normal Hex and Isl1 gene expression and protects against the birth defects that are induced by the three factors. The addition of myo-inositol synergizes with the FA protection following Li exposure. The results, which are based on two different vertebrate models, demonstrate that the two dissimilar factors, Li and HCy, both potentiate the canonical Wnt pathway, which is a crucial pathway in early cardiogenesis and neurogenesis. This pulse of augmentation of Wnt signaling induces birth defects. The finding that FA can rescue direct canonical Wnt3A induction of embryonic defects indicates that FA metabolism intersects with canonical Wnt signaling to provide protection.

During human pregnancy, alcohol use is linked to induction of congenital heart defects associated with Fetal Alcohol Syndrome (FAS). Exposure of vertebrate embryos by a single injection to binge-drinking ethanol levels induced cardiac and valve defects and the severity of anomalies was found to be related to timing of exposure during cardiac specification. EtOH potentiates the Wnt/β-catenin inhibition of early cardiogenesis by suppressing expression of two cardiac inducing molecules, Hex and Isl-1. These genes are normally activated when canonical Wnt signaling is inhibited by Wnt antagonists. There is an intersection between Wnt/β-catenin signaling, EtOH, and folate metabolism. Folate tips the balance toward the differentiated state, which includes formation of the important methyl group donor, S-adenosylmethionine (SAM). Folate supplementation at a high dose, or in combination with myo-inositol, prevents alcohol potentiation of Wnt/β-catenin signaling allowing normal gene activation and cardiogenesis.

β-catenin, an important molecular intermediary in the canonical Wnt signaling pathway, is a recognized factor in the pathogenic impairment of wound healing (Stojadinovic et al., 2005). The inventors discovered that similar factors involving the canonical Wnt pathway are involved both in the induction of heart defects during early embryonic development as well as in wound healing efficiency. As chronic wound development is similarly associated with enhanced Wnt/β-catenin signaling, administering folic acid and myo-inositol precludes adverse molecular effects during wound healing and enhances the healing process. Specifically, a combination of folate and inositol is effective in suppressing the effects of the nuclear β-catenin presence in the epidermis thus allowing for the acceleration of healing. The combination also up-regulates the extracellular matrix molecule fibronectin that is important in enhancing cell migration and wound healing.

A schematic of canonical Wnt signaling is shown in FIG. 1. The canonical Wnt pathway has been shown to regulate cell fate decisions, cell proliferation, and cell migration in the embryo. Canonical Wnt signaling is important for neural development, neural crest specification and differentiation, and cardiac development. The signals are transduced in a cell-context dependent manner to result in rapid changes in gene transcription. Reported evidence indicates that canonical Wnt signaling during narrow windows has differential effects during cardiac specification and heart development.

Figure 2:
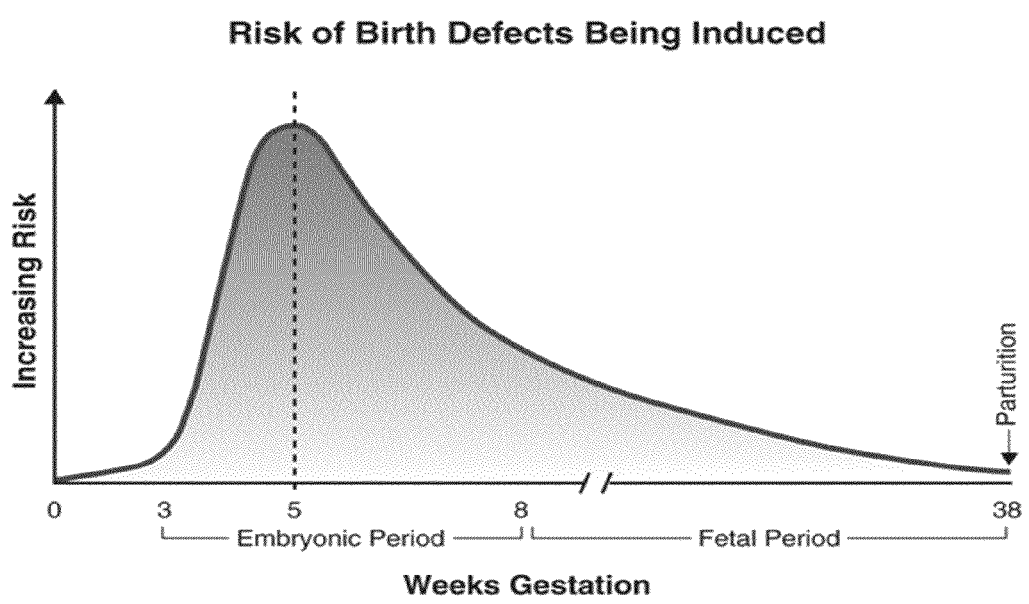
FIG. 2 is a graph showing the risk of birth defects being induced.
Figure 3:
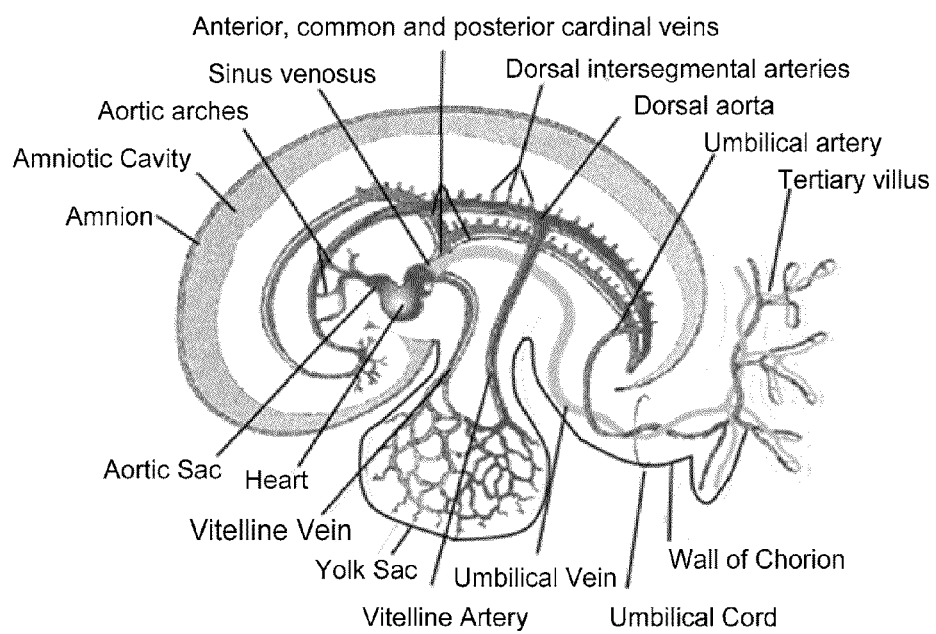
FIG. 3 is a schematic showing the cardiovascular system in a human ~21 days after fertilization.

The heart is the first organ to develop in the embryo and different regions of the heart, including the right and left ventricles and the outflow tract, are already specified at the gastrulation stages. The development is complex, involving two heart fields and the sequential activation of multiple signaling pathways together with regulation of genetic cascades in the cardiogenic crescent. Genetic and environmental effectors can severely impact these pathways and lead to abnormal development. Congenital heart malformations, the most common of human birth defects, occur in ~1% of the population worldwide. Valve and associated structures continue to be the most common subtype of CHDs accounting for 25-30% of all cardiovascular malformations. Cardiovascular defects are also responsible for the majority of embryonic deaths that occur after successful implantation. FIG. 2 is a graph showing the risk of birth defects being induced. The heart compartment develops in an anterior/posterior progression of cell sorting across the bilateral regions of the mesoderm layer. FIG. 3 shows the cardiovascular system in the human ~21 days after fertilization.

Folate (FA) has a pivotal role in DNA synthesis and methylation and the maintenance of normal homocysteine levels. Folic acid prevents neural tube defects and protects other birth defects, including congenital heart defects. It has also been found that folate supplementation can rescue neural tube defects and more recently, using transgenic knockout animals, heart defects. Folate added at the same time with Li or with HCy in the culture medium rescues normal Hex and Isl-1 gene expression and heart development. Folate suppresses effects of Wnt/β-catenin potentiation and reverses the adverse effects of direct canonical Wnt3A exposure on heart development.

The underlying mechanism by which folate (FA) provides protection against neural tube defects has remained unknown (Huhta et al., 2006; Rosenquist and Finnell, 2001). Folate supplementation has been found to rescue gene expression and the cardiac defects induced by canonical Wnt3A, Li or HCy in both avian and mouse embryos. Folate plus inositol synergistically provide the highest percentage rescue of normal avian heart development. A common pathway of Li and HCy induction of cardiac birth defects involves intracellular potentiation of Wnt/β-catenin signaling and an important underlying mechanism of folate protection involves suppression of canonical Wnt signal transduction. The modulation of a dominant early developmental pathway, i.e., canonical Wnt signaling, involved in neurogenesis and cardiogenesis, underlies a mechanism of FA protection against birth defects.

The invention includes methods of modulating Wnt/β-catenin signaling. Lithium (Li), elevated homocysteine (HCy), and canonical Wnt3A (Wnt3A) induce similar heart birth defects during the same stage of development thus indicating that all three factors impact canonical Wnt/β-catenin signaling, although acting at different regulatory levels. Li and Wnt3A both lead to a stabilization of β-catenin that translocates to the nucleus to target certain gene expression in a cell context dependent manner. Because it is known that elevated homocysteine relates to folate (FA) deficiency and it is tied to neural tube defects, the inventors found that folate is able to rescue Li and Wnt3A/β-catenin induced heart defects. This indicates that FA targets the canonical Wnt/β-catenin pathway in providing protection. Because Li also impacts the phosphatidyinositol pathway, the inventors found that the combination of folate and inositol increased the efficacy of protection against Li/Wnt3A effects on heart development in an additive or synergistic manner. Thus, folate and phosphatidyinositol signaling intersect with the canonical Wnt/β-catenin pathway and in combination provide better protection against potentiation of Wnt signaling than either alone.

Example I

Folate Rescues Lithium, Homocysteine, or Wnt3A Induced Vertebrate Cardiac Anomalies Elevated plasma homocysteine (HCy), which results from folate (folic acid, FA) deficiency, and the mood-stabilizing drug lithium (Li) are both linked to the induction of human congenital heart and neural tube defects. The inventors demonstrated previously that acute administration of Li to pregnant mice on embryonic day (E) 6.75 induced cardiac valve defects by potentiating Wnt-β-catenin signaling. HCy similarly induces cardiac defects during gastrulation by targeting the Wnt-β-catenin pathway. Maternal elevation of HCy or Li on E6.75 induced defective heart and placental function on E15.5, as identified noninvasively using echocardiography. This functional analysis of HCy-exposed mouse hearts revealed defects in tricuspid and semilunar valves, together with altered myocardial thickness. A smaller embryo and placental size was observed in the treated groups.

FA supplementation ameliorates the observed developmental errors in the Li- or HCy-exposed mouse embryos and normalized heart function. Molecular analysis of gene expression within the avian cardiogenic crescent determined that Li, HCy or Wnt3A suppress Wnt-modulated Hex (also known as Hhex) and Islet-1 (also known as Isl1) expression, and that FA protects from the gene misexpression that is induced by all three factors. Furthermore, myo-inositol with FA synergistically enhances the protective effect. Although the specific molecular epigenetic control mechanisms remain to be defined, it appears that Li or HCy induction and FA protection of cardiac defects involve intimate control of the canonical Wnt pathway at a crucial time preceding, and during, early heart organogenesis.

Avian Model

HCy or Li Exposure in Avian Embryos During Hamburger-Hamilton (HH) Stages 3+ to 5 Induced Similar Heart Defects Pathogen-free White Leghorn chick (*Gallus gallus*; Charles River, MA) and quail (*Coturnix coturnix japonica*; Strickland Farms, GA) embryos were used to analyze the effects of HCy on early embryogenesis. The early processes of heart development are well conserved among vertebrates and the avian model allows for more precise timing of exposure in early embryos. The incubation methodology using agarose-albumin has been described previously (Darnell and Schoenwolf, 2000). Briefly, the experimental paradigm involved exposing specific early stages of chick embryos, at HH stages 4 to 7 (Hamburger and Hamilton, 1951), to different concentrations of HCy (L-homocysteine thiolactone hydrochloride, Sigma) made up in physiological saline. Final concentrations of HCy included 30 µM, 50 µM, 75 µM and 100 µM. The minimal teratogenic dose was determined empirically to be 50 µM. This fit within the concentration range of 30 µM to 300 µM used by others that induced heart defects at later stages of development (Boot et al., 2004). Control embryos were incubated using the vehicle, physiological saline, in the agarose-albumin medium. Control and experimental cultures were incubated on the agarose-albumin plates for either 8 or 24 hours.

Carrier-free, recombinant mouse Wnt3A was purchased from R&D Systems (Minneapolis, Minn.). Wnt3A concentrations were empirically tested to find those that would induce cardiac defects but maintain embryonic viability. Wnt3A was tested at concentrations of 2 ng, 10 ng, 20 ng, 50 ng and 100 ng per ml. Concentrations of 2 ng/ml and 10 ng/ml were both effective in inducing cardiac defects. Both Wnt3A concentrations were used in the FA rescue experiments, as described. For the FA rescue experiments, folate (folic acid, Sigma-Aldrich) was added at a concentration of 2 µg, 5 µg or 10 µg per ml. In subsequent experiments, 10 µg/ml FA was used, which consistently rescued the heart defects induced by Li, HCy or Wnt3A in the avian model. For the experiments using inositol (myo-inositol, Sigma) supplementation, a concentration of 50 mg/ml was used.

In situ hybridizations on control and experimentally manipulated chick embryos were carried out using digoxigenin-labeled riboprobes with alkaline phosphatase detection (Linask et al., 2001). Images of whole-mounted chick embryos were taken with a Nikon DS-L2 camera unit. Probes for chick Hex were provided by Parker Antin, University of Arizona and probes for chick Islet-1 (Isl1) were provided by Thomas Jessell, Columbia University, NY.

Figure 4:
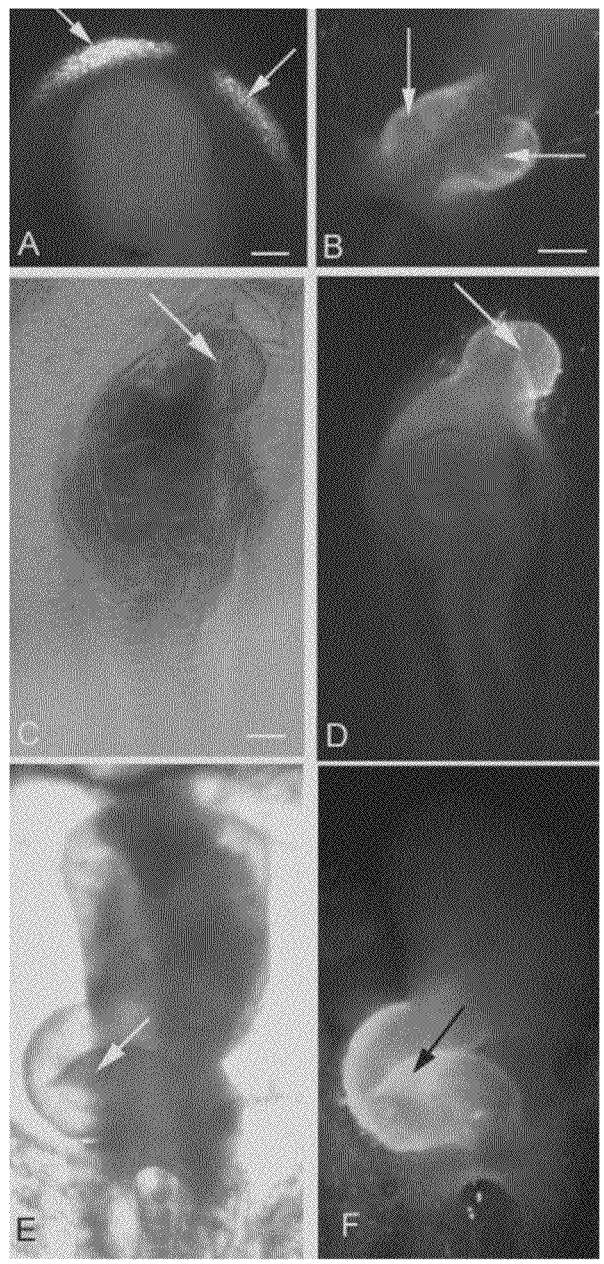
FIGS. 4A-F are a series of images showing the effects of exogenous Hcy on early chick heart development after 24 hr incubation. Immunolocalization of MF20 defines presence of cardiac tissue (arrows). (A and B). Two extremes of cardiabifida: (A). Two small cardiogenic regions are differentiating bilaterally. (B). The two heart fields have moved close to the midline and are almost touching, ready to fuse. (C) Light microscopic view of an embryo displaying a severely truncated neural tube with (D) cardiac tissue differentiating cephalad to the neural area. (E-F). Ventral view of a normal, control, right-looping heart. Magnification bars for A-F=300 µm

The peak time of sensitivity corresponded to HH stages 3+/4 to stage 5, in which 78% (n=128) and 68% (n=74) of embryos, respectively, that were exposed to elevated HCy (50 µM) displayed cardiac abnormalities, which were defined by immunolocalization of sarcomeric myosin heavy chain using MF20 antibody (FIG. 4). Exposure at HH stages 6 and 7 led to normal development. The main embryonic defects related to the timing of embryonic exposure; the regions that were primarily affected related to an anterior-to posterior (AP) wave of development along this embryonic axis. The exposure effects ranged from early effects (e.g. no cardiac tissue, heart development occurring anterior to neural tissue, cardiabifida) to later effects, such as wide hearts and left looping (Table 1). The cardiac phenotypes observed with early HCy exposure were similar, although not identical, to those obtained from previous studies of Li exposure on avian heart development (Manisastry et al., 2006). The Wnt/β-catenin modulated genes Hex and Isl1 in the chick embryo also were similarly repressed with HCy, as with Li in the chick cardiogenic region. Analysis of ultrasound parameters indicated that myocardial function of Li-exposed embryos is more affected than HCy-exposed embryos. Embryonic growth restriction was noted in both groups. Histological evaluation of the HCy hearts showing abnormal echo patterns revealed alterations in tricuspid and semilunar valves and changes in myocardial thickness. Investigation of regulatory gene activity in chick embryos indicates Li, HCy and Wnt3A suppress Wnt-modulated genes Hex and Islet-1 in the heart fields.

HCy and Li suppress Hex and Islet-1 (Isl1) gene expression in the avian heart fields. The avian model allows for more precise targeting of exposure to specific early stages of development. Mouse embryos within a litter can vary widely in their developmental stages, leading to misinterpretation of results when, at the time of the acute exposure, the window of susceptibility for some embryos has already passed. In the Li study, the inventors detected that the viable defects in the mouse embryo were related to derivatives of the SHF. Therefore, the inventors also analyzed the effects of HCy and Li exposure on Isl1 expression, a SHF marker that is modulated by β-catenin in the canonical Wnt signaling pathway (Cai et al., 2003; Lin et al., 2007).

TABLE 1

Early Embryonic Chick Model:
Exposure to 50 µM HCy leads to cardiac defects

| AbnormalityType | Frequency | Percent |
|---|---|---|
| Left looping* | 11 | 10.2 |
| Cardiabifida* | 11 | 10.2 |
| Wide heart* | 24 | 22.2 |
| Heart above head | 18 | 16.7 |
| Heart close midline* | 15 | 13.9 |
| Tubular heart | 3 | 2.8 |
| Very abnormal (or no hearts) | 18 | 16.7 |
| Delayed development | 2 | 1.9 |
| Dead | 6 | 5.6 |
| Total | 108 | 100.0 |

*Midline related anomaly

Figure 5:
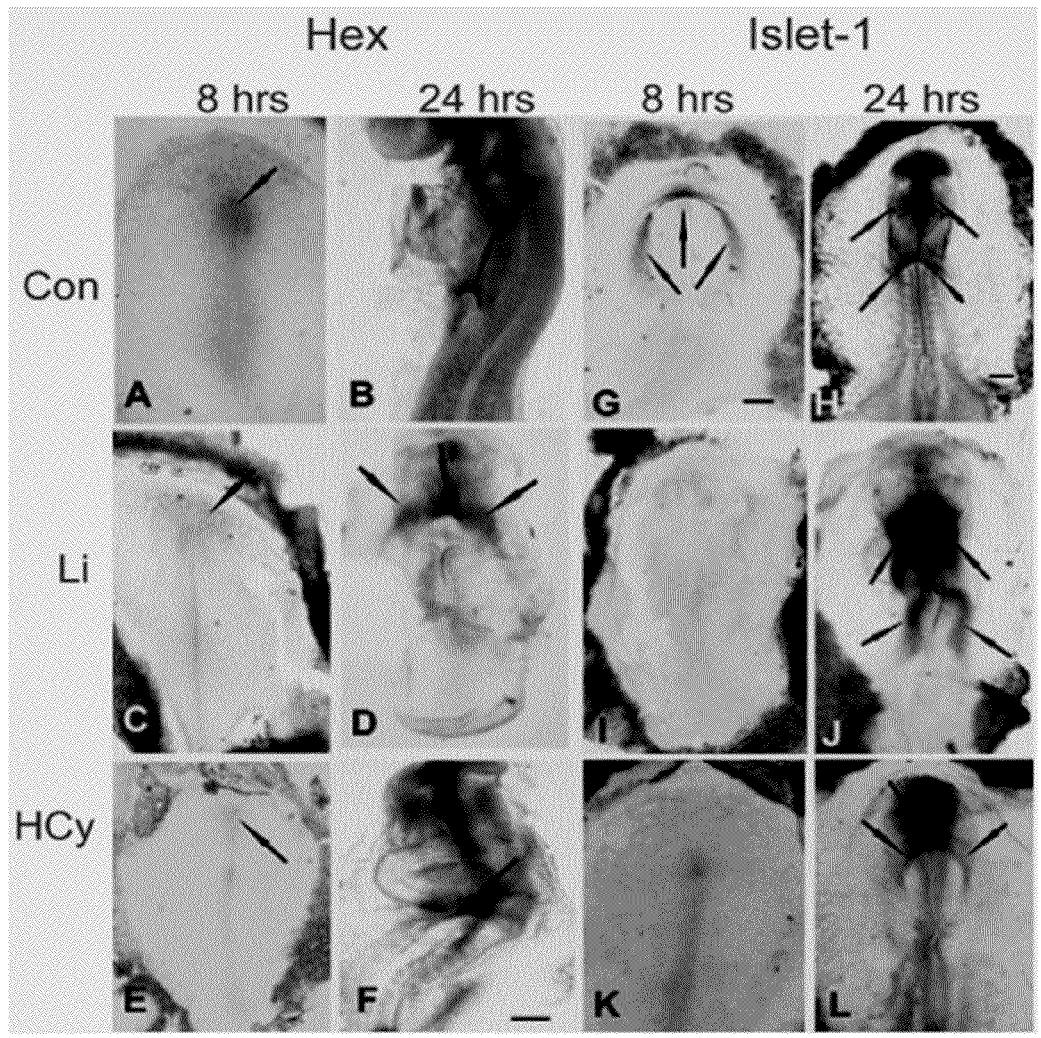
FIGS. 5A-L are a series of images showing Hex and Islet-1 (Isl-1) gene expression patterns after 8 and 24 hrs in control and Li-(A-F) and HCy-(G-L) exposed embryos. Red arrows point to cardiac tissue; black arrows to in situ gene expression. Top row: Control (Con) Hex and Isl-1 expression is seen at relatively high levels after 8 (A, G) and 24 (B, H) hrs incubation. Hex and Isl-1 gene expression is suppressed in chick embryos with Li (C; second row) or HCy (E; bottom row) exposure at HH stages 3+/4−. By 24 hr, a recovery of expression is noted, but embryos remain delayed in development (D, F). Modulation of Islet-1 is similar: Little or no Ist-1 gene expression is detectable after 8 hr to Li or HCy exposure (Li, I; HCy, K). By 24 hrs, heart development is delayed and cardiac anomalies arise (J, L). Magnification bars=300 µm

Chick embryos (HH stages 3+/4) were incubated on agarose albumin supplemented with HCy (50 µM). Instead of giving a single injection in ovo, embryos were exposed to HCy for 8 hours in order to define the effect on early cardiac gene expression. Another group of embryos were exposed to HCy for 24 hours at which time the effects on gene expression were determined. To analyze the effects during the looping stages, incubation was stopped after between 22 and 24 hours. After the 8-hour incubation, Li and HCy suppressed Hex and Isl1 expression in the cardiogenic crescent (FIG. 5).

In the untreated control embryo, Hex expression was apparent in the Hensen's node region, anteriorly in the prechordal plate, and extending laterally (FIG. 5A). By 24 hours, Hex was still apparent in the anterior intestinal portal (AIP) endoderm in a looping HH stage 14 heart (FIG. 5B). Exposure to either Li (FIG. 5C) or HCy (FIG. 5E) for 8 hours decreased Hex expression in the prechordal plate. After exposure to Li for 24 hours, Hex was expressed in the AIP and cardiogenic regions of a developmentally delayed embryo (FIG. 5D). After exposure to HCy for 24 hours, the embryo had a looping heart with a truncated neural tube, and the AIP region displayed only diffuse Hex expression (FIG. 5F). By contrast, the control embryo had developed to a late-looping stage (FIG. 5B). If HCy or Li exposure occurred at HH stages 6 or 7, Isl1 expression was already activated and was similar to control embryos (not shown). In summary, 8 hours of Li or HCy exposure during the early stages of chick development repressed Hex and Isl1 expression. By 24 hours, Isl1 gene expression had recovered but heart development and neural tube development were abnormal and remained delayed.

FA Protects Against HCy- and Li-Induced Adverse Effects in Early Chick Cardiac Development FA-supplemented medium rescued HCy- and Li-induced heart defects in embryos that were exposed between HH stages 3 and 5 (Table 2). At HH stages 3 and 4, FA supplementation at 10 µg/ml provided protection in embryos exposed to HCy (50 µM) or Li, with 54% and 48% of HCy- and Li-exposed embryos, respectively, displaying normal heart development. Without FA supplementation, only 22% and 28% of HCy- and Li-exposed embryos, respectively, had normal heart development. Of the HH stage ¾ control embryos that had been treated with physiological saline, 48% showed normal development.

TABLE 2

FA or Inositol Supplementation Increases Percent Normal Heart Development

| HH Stage | *Treatment | # Embryos | Abnormal | Normal | % Normal Hearts |
|---|---|---|---|---|---|
| 3+/4 | Control (NaCl) | 87 | 45 | 42 | 48% |
| 3+/4 | HCy | 128 | 100 | 28 | 22% |
| 3+/4 | HCy + FA | 57 | 26 | 31 | 54% |
| 5 | Control (NaCl) | 42 | 11 | 31 | 74% |
| 5 | HCy | 74 | 50 | 24 | 32% |
| 5 | HCy + FA | 22 | 6 | 16 | 73% |
| 3+/4 | FA only | 11 | 5 | 6 | 55% |
| 3+/4 | Inositol only | 5 | 2 | 3 | 60% |
| 3+/4 | Li only | 29 | 21 | 8 | 28% |
| 3+/4 | Li + FA | 40 | 21 | 19 | 48% |
| 3+/4 | Li + Inositol | 30 | 18 | 12 | 40% |
| 3+/4 | Li + FA + Inositol | 34 | 9 | 25 | 74% |

*Concentrations used: HCy, 50 μM; Li, 50 μM; FA, 10 μM; inositol, 280 mM

There was an association between the severity of defects and the developmental stage at exposure. HCy exposure (50 μM) beginning at HH stage 5 resulted in normal cardiac development in 32% of embryos. With FA supplementation, 73% of HH stage 5 embryos had normal cardiac development. In summary, FA rescued cardiac defects, but was less effective at the early stages of development when the HCy- or Li-induced defects would be embryonic lethal.

Inclusion of FA and Inositol is Additive or Synergistic, and Increases the Percentage of Li-Exposed Embryos that Display Normal Development In addition to mimicking canonical Wnt signaling, Li modulates phosphatidylinositol signaling (Belmaker et al., 1998). The inventors analyzed whether the combination of inositol (50 mg/ml) and FA supplementation would result in a higher percentage of embryos with normal heart development within the more severely affected HH stage 3+/4 group (Table 2). FA supplementation or inositol alone produced similar percentages of normal heart development (55% and 60%, respectively) compared with the control group (48%). A combination of inositol and FA was additive or synergistic and, in the presence of Li, increased normal development to 74% in in vitro culture conditions.

FA Protects Against Wnt3A-Induced Heart Defects

Figure 6:
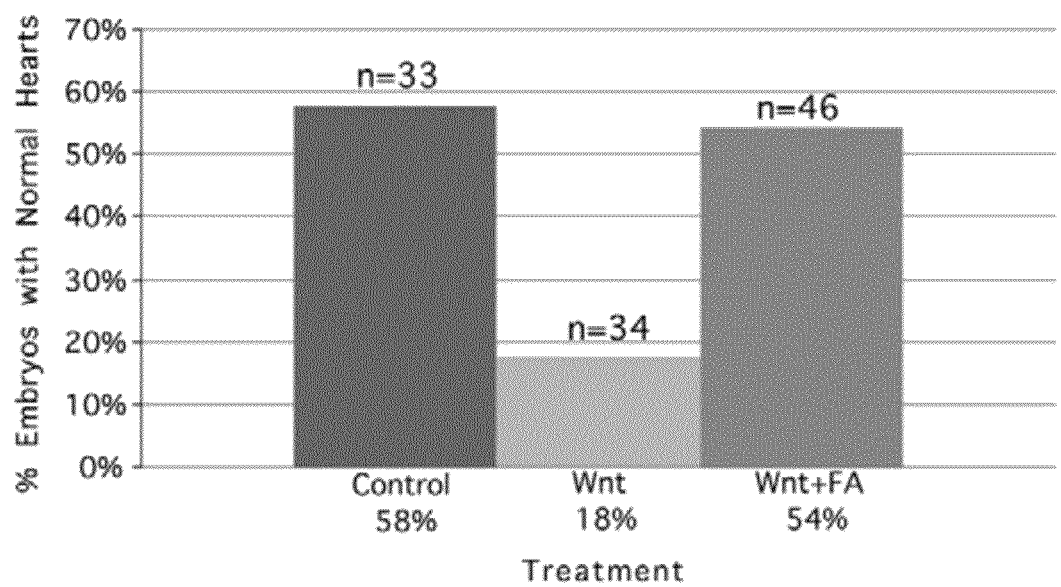
FIG. 6 is a graph showing that folate supplementation with embryonic Wnt3A-exposure increases the percentage of normal heart development. Control group displayed 58% normal development in contrast to 18% in Wnt3A exposed group. FA supplementation increased the percentage of Wnt3A-exposed embryos with normal development to control levels.
Figure 7:
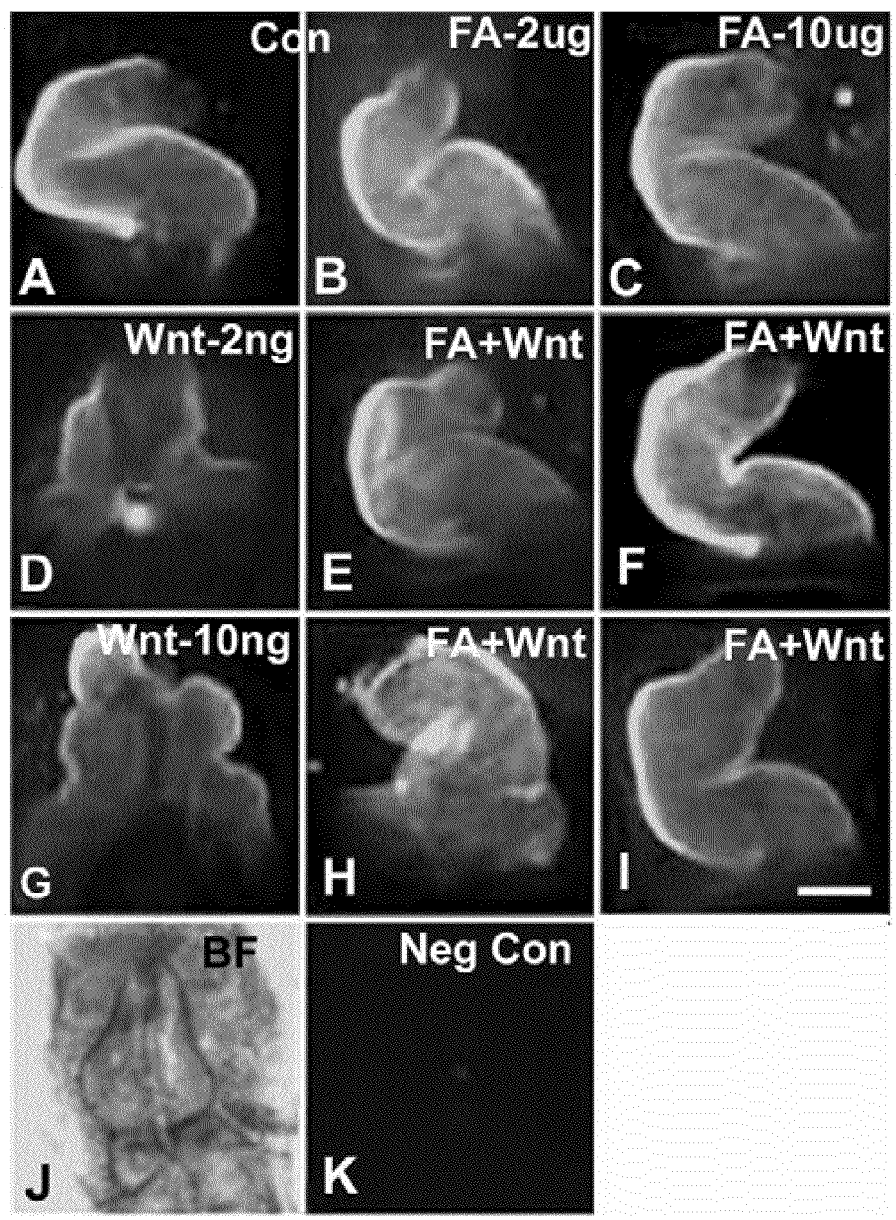
FIGS. 7A-K are a series of images showing that folate rescues heart development of Wnt 3A exposed avian embryos. Embryos were immunostained with MF20 antibody for sarcomeric myosin heavy chain as a marker for differentiated cardiomyocytes. Control embryonic hearts in whole mounts are shown in top row. (A) Untreated embryo; (B) FA only, 2 µg/ml; and (C) FA only, 10 µg/ml. HH stages 3+/4 embryos exposed to 2 ng/ml (D) or 10 ng/ml Wnt3A (G) display abnormal heart development. FA supplementation administered at a concentration of 2 µg/ml (E) rescues embryonic heart development at the 2 ng/ml Wnt3A concentration, but only partially rescues heart development in embryos exposed to 10 ng/ml Wnt3A concentration (H; left looping heart). FA supplementation at a concentration of 10 µg/ml completely normalized heart development with either low or high level of Wnt 3A exposure (F and I). J, bright field of embryo shown in K, a negative control without primary antibody treatment. In all panels, the embryonic anterior is at the top. Bar 275 µm.

Since both HCy and Li modulate the canonical Wnt pathway during the cardiac specification stages, FA rescues the deleterious effects of augmentation of canonical Wnt3A (Manisastry et al., 2006) on heart development as shown in FIGS. 6 and 7.

To define the effective dose of Wnt3A needed to induce cardiac dysmorphogenesis, Wnt3A was tested at concentrations of 2 ng, 10 ng, 20 ng, 50 ng, and 100 ng per ml. The minimal effective doses of Wnt3A that induced cardiac and neural anomalies were 2 ng/ml and 10 ng/ml, respectively. Using these concentrations, the inventors analyzed whether FA supplementation of media at $10^3$-fold higher concentrations, that is 2 μg/ml or 10 μg/ml, would provide protection against the augmentation of canonical Wnt3A signaling.

Figure 8:
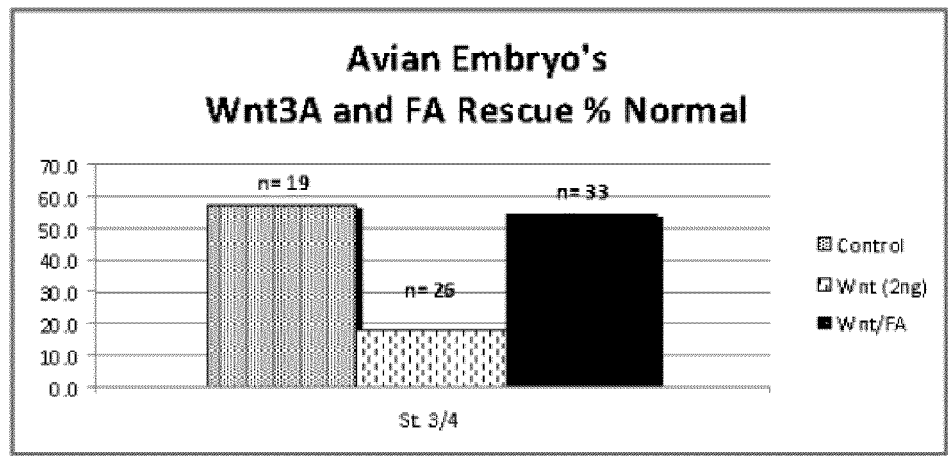
FIG. 8A-D are a series of images depicting FA rescue of cardiac development in avian embryos. (A) is a graph depicting that Wnt3A media supplemented with FA rescued normal heart development (54.3%) to near control levels (57.6%); (B) is the raw control data; (C) is the raw data for Wnt (2 ng) administration; (D) is the raw data for the combination of 2 ng Wnt administered with 10 µg FA.

With only Wnt3A exposure at HH stages 3+/4, 18% of embryos had normal hearts; Wnt3A media supplemented with FA rescued normal heart development (54%) to near control levels (58%) (FIGS. 6, 7 and 8). A normal looping control heart is shown with MF20 immunolocalization of sarcomeric myosin heavy chain (FIG. 7A). The addition of FA alone, at a concentration of 2 μg/ml or 10 μg/ml, resulted in normal heart development (FIGS. 7B and 7C, respectively). Embryos exposed to 2 ng/ml of Wnt 3A (FIG. 7D) displayed incomplete cardiac tube formation, whereas those exposed to 10 ng/ml displayed cardiabifida (FIG. 7G). Wnt3A (2 ng/ml) in the presence of 2 μg/ml (FIG. 7E) or 10 μg/ml (FIG. 7F) of FA supplementation resulted in normal heart development. At the higher Wnt 3A concentration (10 ng/ml) (FIGS. 7G-I), FA supplementation at the 2 μg/ml level provided only partial rescue of tube formation (FIG. 7H), and left-looping hearts were observed occasionally. The higher FA concentration (10 μg/ml) also rescued heart development in the high Wnt3A exposure group (FIG. 7I). To summarize, FA suppressed the effects of direct Wnt3A potentiation of canonical Wnt signaling and normalized development.

Figure 9:
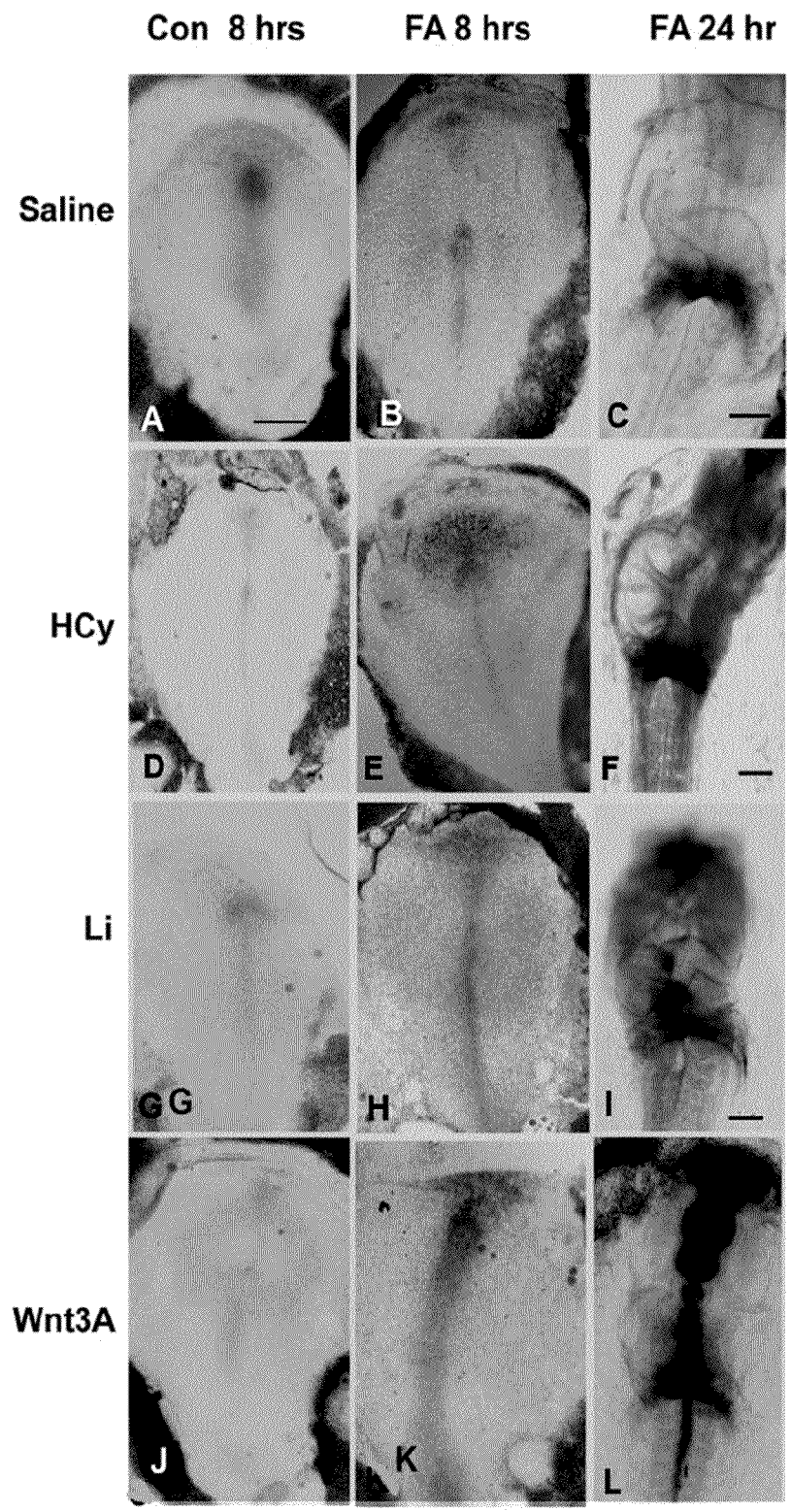
FIGS. 9A-L are a series of images showing that folate rescues Hex expression in Li, HCy, and Wnt3a-exposed avian embryos. Top row shows normal patterns of Hex expression in (A) control embryos (saline added) after 8 hrs, (B) after folate exposure only at 8 hrs, and (C) at 24 hrs. Second row depicts gene expression 8 hrs after (D) HCy only exposure, (E) HCY with FA supplementation; and (F) 24 hrs after HCy with FA supplementation. Third row depicts gene expression 8 hrs after (G) Li only exposure, (H) Li with FA supplementation; and (I) 24 hrs after Li with FA supplementation. Fourth row depicts gene expression 8 hrs after (J) Wnt3A only exposure, (K) Wnt3A with FA supplementation; and (L) 24 hrs after Wnt3A with FA supplementation. In all panels, the embryonic anterior is at the top. Bars, 300 µm.
Figure 10:
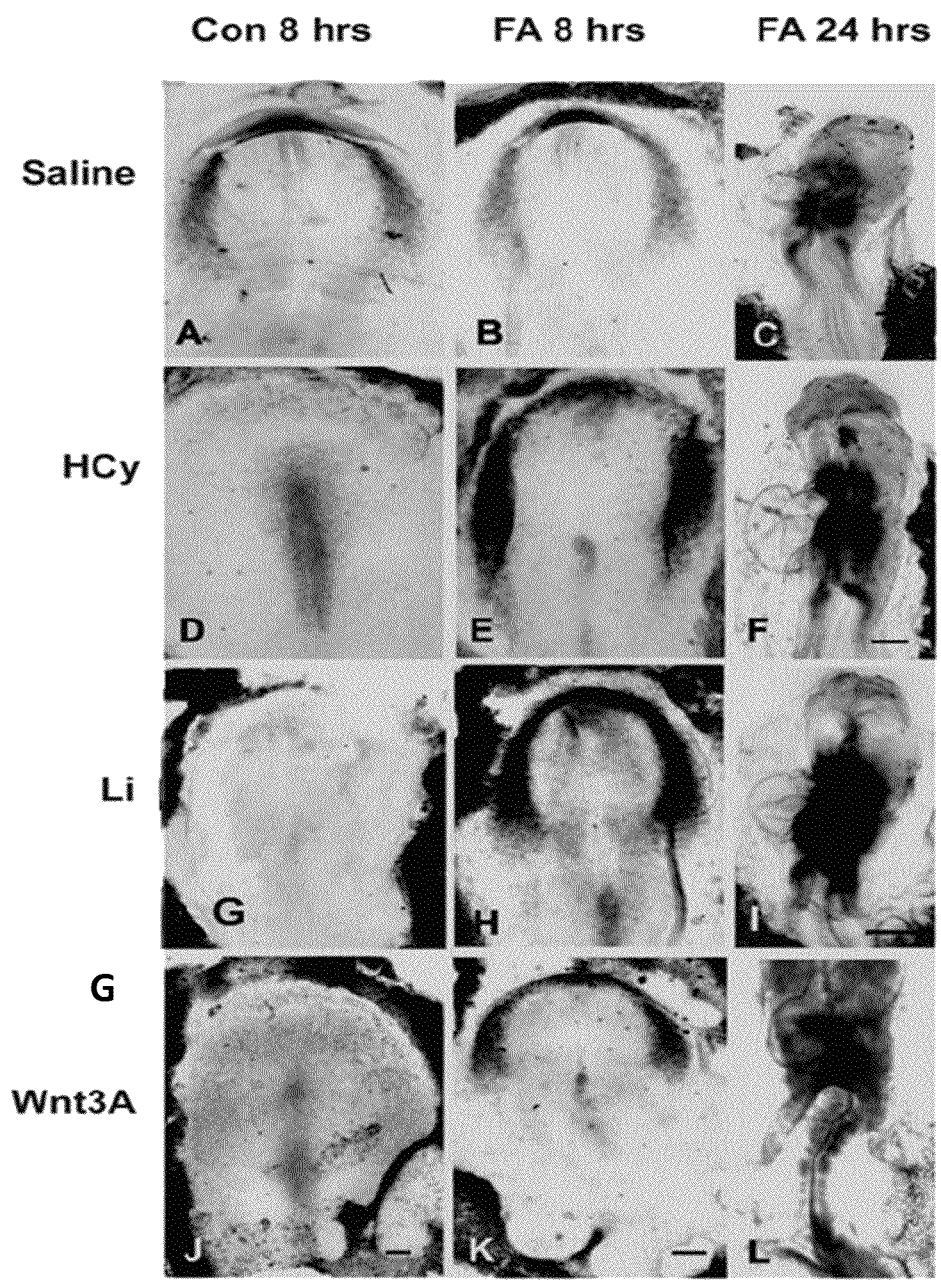
FIGS. 10A-L are a series of images showing that folate rescues Isl-1 expression in Li, HCy, and Wnt3A-exposed avian embryos. Top row shows normal patterns of Isl-1 expression in (A) control embryos (saline added to medium) after 8 hrs, (B) after folate exposure only at 8 hrs, (C) at 24 hrs. Second row depicts gene expression 8 hrs after (D) HCy only exposure, (E) HCY with FA supplementation; and (F) 24 hrs after HCy with FA supplementation. Third row depicts gene expression 8 hrs after (G) Li only exposure, (H) Li with FA supplementation; and (I) 24 hrs after Li with FA supplementation. Fourth row depicts gene expression 8 hrs after (J) Wnt3A only exposure, (K) Wnt3A with FA supplementation; and (L) 24 hrs after Wnt3A with FA supplementation. In all panels, the embryonic anterior is at the top. Bars, 300 µm.
Figure 12:
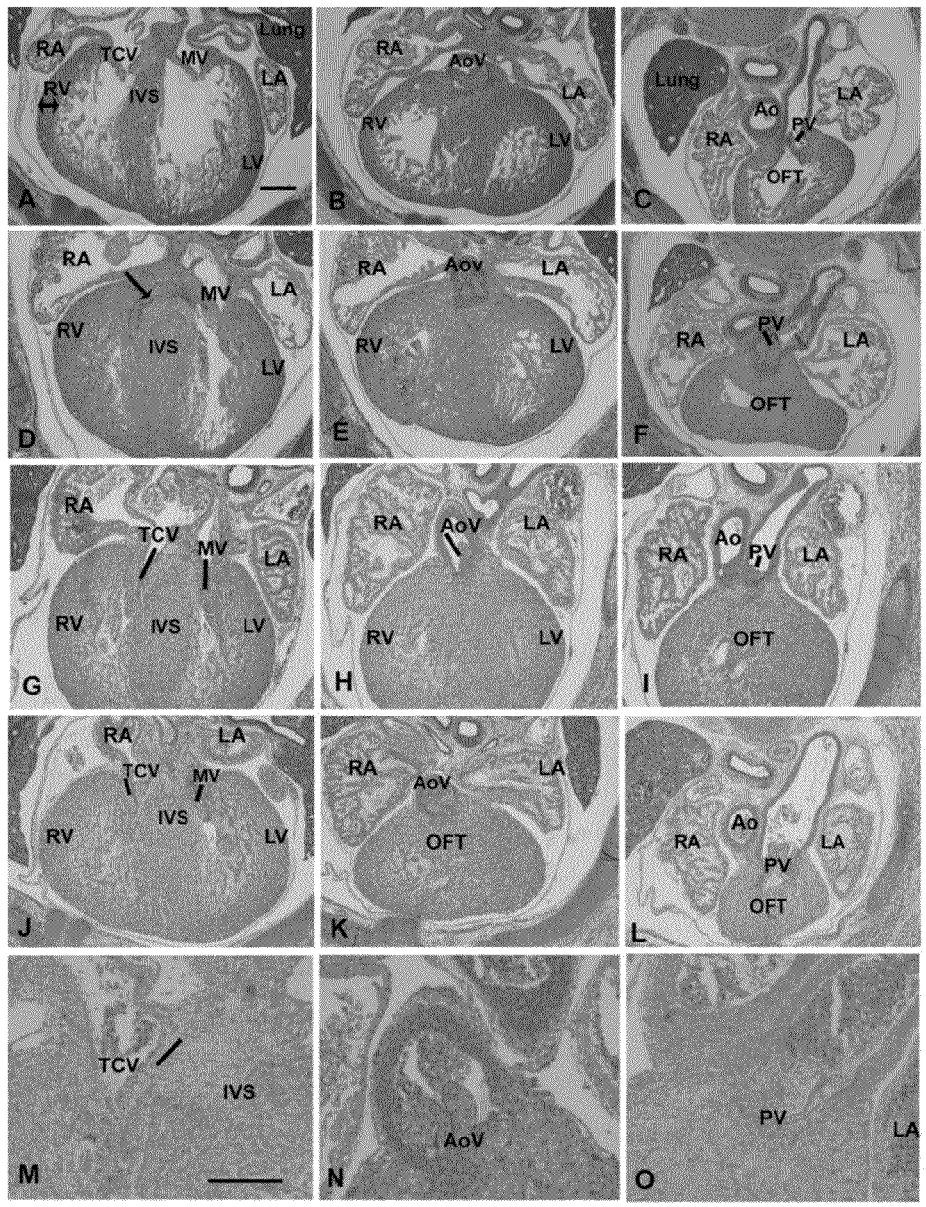
FIGS. 12A-O are a series of images showing the pathology of HCy-exposed E15.5 mouse hearts displaying abnormal echo patterns. The panels in the left column depict AV valves (TCV, tricuspid valve; MV, mitral valve); the middle column shows aortic valves (AoV); and the right column shows pulmonary valves (PV). (A-C) A control heart. (D-F) An embryo with AV valve regurgitation. (G-I) An embryo displaying SL and AV valve regurgitation upon echocardiography. (J-L) The echo patterns for this embryo defined pulmonary stenosis. (M-O) Higher magnification of valves in hearts showing valve regurgitation upon echocardiography of an AV valve (M) and SL valves (N,O). RA, right atrium; RV, right ventricle, LA, left atrium; LV, left ventricle; IVS, interventricular septum; Ao, aorta; OFT, outflow tract. In all panels, the embryonic anterior is to the top. Bars, 152 µm.

FA Rescues Li-, HCy- and Wnt3A-Induced Misexpression of Hex and Isl1 at the Gastrulation Stages The inventors next analyzed whether FA rescues the down-regulation of Hex and Isl1. Chick embryos were exposed to Li, HCy or Wnt3A, as above, with and without 10 μg/ml of FA; the experiments were terminated after either an 8-hour or 24-hour exposure period, at which time in situ hybridizations for gene expression were performed. After 8 hours of exposure, Li, HCy and Wnt3A all suppressed Hex (FIG. 9D, G, J) and Isl1 (FIGS. 10D, G, J) compared with the control embryonic expression patterns (FIG. 9A; FIG. 10A). FA supplementation for 8 hours resulted in normalized gene expression patterns and the expression was at higher levels than in control embryos [FIGS. 9B, E, H, K (for Hex); FIGS. 10B, E, H, K (for Isl1)]. By 24 hours, normal beating hearts had formed and normal Hex (FIGS. 9C, F, I, L) and Isl1 (FIGS. 10C, F, I, L) gene expression was apparent in the developing atrial region in the SHF. Thus, FA supplementation suppressed the potentiation of the inhibitory Wnt signaling, allowing for normal induction of Hex and Isl1 gene expression.

Mouse Model

To determine whether the results in the avian system would extend to the mammalian system, the inventors conducted studies in the mouse embryo. All mice were maintained according to protocols approved by the Institutional Animal Care and Use Committee at the University of South Florida. The C57BL/6 mouse strain (Jackson Laboratories, Bar Harbor, Me.) was used throughout the study. E0.5 was defined as the morning when the vaginal sperm plug was detected. Timed pregnant mice were randomly allocated to receive a single dose of 100 μl of 6.25 mg/ml Li chloride, as determined previously (Chen et al., 2008), 100 μl of 75 μM HCy, or 100 μl of 6.25 mg/ml sodium chloride (control group); all treatments were given intraperitoneally (i.p). On E15.5, the uteroplacental circulation of the pregnant mice, and the central and peripheral circulations of the embryos were examined non-invasively in utero using Doppler ultrasonography (Gui et al., 1996; Linask and Huhta, 2000). Sixty-eight embryos were exposed to Li, 59 to HCy and 42 to physiological saline.

An HCy concentration of 75 μM, used for maternal exposure, was determined empirically using different doses of HCy (i.e. 150, 75, 50 and 15 μM). The minimal teratogenic dose was determined to be 75 μM. An acute, single dose of HCy at E5.5 resulted in embryonic lethality (79% of embryos; there were 11 resorptions and 3 small, but viable, embryos). The single i.p. injection of HCy at E6.75 produced a high number of valve defects (66%), as well as resorptions (46%). An i.p. injection on E7.75 did not cause any valve defects (n=16). Because not all embryos within litters are at exactly the same stage of development, the variability of effects seen with either Li or HCy probably reflects the differences in developmental stage. Hence, the variable effects that were observed on heart and valve development were expected.

FA Diet for Rescue of Cardiac Defects in Mouse Embryos

Animal chow was supplemented with 10.5 mg/kg of FA, which was the concentration used in trial human population studies. As a control diet (i.e. normal mouse chow), mice continued to receive 3.3 mg/kg of FA as the baseline to maintain the health of the female mice. The baseline supplementation does not rescue cardiac defects. The animal chow supplemented with 10.5 mg/kg of FA was prepared for us by Harlan Laboratories. As recommended by Harlan, the calculations for the FA level in the special diet are based on the metabolic body weight of mice. Because of the obvious large difference in body weight between humans and mice, and because of the large difference in metabolic rate, Harlan uses the metabolic weight as a method of scaling these differences between species; for mice this was calculated to be BW0.75 (i.e. metabolic weight equals body weight to the 0.75 power). Each mouse consumes approximately 4 g of chow per day; therefore, to obtain the desired dose of 10.5 mg/kg, we added 7.2 mg/kg of FA to the normal 3.3 mg/kg that is present in commercial chow. Pregnant mice were divided randomly into the experimental group that was supplemented with 10.5 mg/kg of FA and the control group of mice that did not receive any additional FA. On the morning of the plug date (E0.5), the pregnant mice were placed on the defined Harlan chows and maintained on this diet throughout the study. On E6.75 (at 15:30 PM) all pregnant females received Li (6.25 mg/125 µl), by an i.p. injection, which consistently induced valve and heart defects, as detected by echo on E15.5.

Doppler Ultrasonography

Doppler ultrasonographic examinations were carried out using the Philips Sonos 5500 (Andover, Mass.) with a 12 MHz transducer and, more recently, with a Vevo 770 (VisualSonics) system. Both instruments provided similar echo patterns. On E15.5, the pregnant mice were anesthetized using a Surgivet Tech 4 anesthesia system (Waukesha, Wis.) with inhalation anesthesia, consisting of 3% isoflurane, administered through a nose cone; the mice were then maintained on 1% isoflurane with 21% oxygen. The mother was placed supine on a heating pad with electrode footpads. The heart rate and temperature of the pregnant mice were monitored using a THM100 (Indus Instruments, Houston, Tex.) during scanning. The body temperature was maintained at 37° C.

Maternal uterine artery blood flow velocity waveforms were obtained and the pulsatility index was calculated. The embryos were visualized and their position mapped in each uterine horn. Blood flow in the heart and blood vessels was detected in each embryo using color Doppler, and blood flow velocity waveforms were obtained using pulsed wave Doppler. Once the embryonic heart was identified by color Doppler, the sample volume of the pulsed Doppler was placed over the entire heart to obtain blood velocities. The gate length was adjusted to completely insonate the beating embryonic heart. The high-pass filter was at its lowest setting of 50 Hz. The embryonic heart was examined from several angles of insonation to obtain the maximal velocities and inflow and outflow waveforms. The pulsatility index (PI) was calculated from the descending aorta, umbilical artery and ductus venosus blood flow velocity waveforms. The cardiac cycle time intervals were measured from the inflow-outflow velocity waveforms, and the index of global myocardial performance (Tei index) was calculated as: (ICT+IRT)/ET, where ICT is the isovolemic contraction time, IRT is the isovolemic relaxation time and ET is the ejection time (FIG. 11). The presence of any valvular regurgitation was recorded. Holosystolic AV valve regurgitation was defined as regurgitation that occurred from the closure to the opening of the AV valve and with a peak velocity higher than 50 cm/second. SL valve regurgitation was identified as the diastolic blood velocity waveform that is usually superimposed on the inflow waveforms. During echo, although the diastolic regurgitation jet of the SL valve is usually superimposed on the inflow waveform, by manipulating the ultrasound transducer and sample volume of the Doppler gate it is possible to obtain the inflow waveforms in the same Doppler envelope, thus allowing the measurement of IRT. After the ultrasonographic examination, the female mouse was euthanized and the fetuses within the uterine horns were identified according to their location during the ultrasonographic examination. The embryos were removed and processed for paraffin sectioning.

Statistical Analysis

Statistical analysis was performed using SAS version 9.1 (Cary, N.C.). The non-parametric Kruskal-Wallis test was used to determine if there was any significant difference among the three groups (global test). If the global test indicated that a significant difference existed, pair-wise comparisons were carried out to test which pair(s) had a significant difference, again using the non-parametric Kruskal-Wallis test. Three possible pairs were analyzed: control versus HCy, control versus Li, and Li versus HCy. The significant differences are highlighted in Table 3. $P<0.05$ was considered statistically significant.

Histology and Microscopy

Li- and HCy-exposed embryos, and control NaCl-exposed embryos, were fixed in 4% paraformaldehyde in phosphate buffered saline (PBS, pH 7.4) and paraffin sectioned. Sections were stained with hematoxylin-eosin, and some were stained with Toluidine Blue, and examined. Cardiac regions were analyzed for the presence of any obvious malformations using a Nikon SMZ1500 fluorescent stereomicroscope, and digitized images were obtained using a Nikon DS-L2 camera unit.

Histological analysis shows defects in tricuspid and semilunar valves and altered myocardial thickness in HCy- and Li treated embryos. These embryos, and their placentas, were also smaller than control animals. When FA supplementation was started immediately after fertilization, it prevented these developmental errors. Gene expression studies within the avian heart-forming regions demonstrate that Li, HCy and Wnt3A suppress Wnt-modulated Hex and Isl1 expression, and that FA prevents this effect. Inclusion of myo-inositol with FA supplementation potentiates the protection of Li-induced errors.

The effects of increased maternal HCy serum levels were studied by acute targeting of the same E6.75 developmental window that induced cardiac defects with Li exposure. Doppler ultrasound was used to monitor non-invasively the effects on heart and placental function. As revealed with subsequent echocardiography of embryonic heart function on E15.5, the same types of cardiac valve defects developed in Hcy exposure as with Li exposure (Chen et al., 2008). Both experimental groups displayed valve regurgitation: Li group (63.2%) and HCy (66.1%). The maternal and embryonic hemodynamic variables measured by Doppler ultrasonography on E15.5 embryos are shown in FIG. 11, and a comparison between the HCy and Li echo data is provided in Tables 3 and 4. The significant differences are highlighted below.

Li Group Compared with Control Group

Based on the median values shown in Table 3, the maternal heart rate was higher and the uterine artery pulsatility index was lower in the Li group versus the control group. With Li exposure, 63% (n=43/68) of embryos displayed valve regurgitation (FIG. 11A, normal pattern; FIGS. 11B-D, abnormal pattern): semilunar (SL) valve regurgitation (FIG. 11C) occurred in 34 (50%) of the embryos, and both SL and atrioventricular (AV) valve regurgitation occurred in 9 (13%) of the embryos. The increased atrial contractility may be a compensatory mechanism, since compliance of the ventricles was reduced.

TABLE 3

Comparison of Maternal and Embryonic Hemodynamic Parameters obtained by Doppler Ultrasonography at E15.5 (C57Bl/6J mice) after Exposure at E6.75 to Lithium Chloride, Homocysteine, or NaCl (0.9%, Control)

| Variable | Hcy (n = 59) | NaCl (n = 42) | LiCl (n = 68) | p value |
|---|---|---|---|---|
| Maternal | | | | |
| Heart Rate (beats/min) | #458 | 421 | 491 ↑ | <0.0001* |
| Uterine Artery PI | 2.82 | 2.77 | 2.12 ↓ | 0.0001* |
| Embryonic | | | | |
| Heart Rate (beats/min) | 181 | 169 | 195 ↑ | 0.0004* |
| Umbilical Artery PI | 1.55 | 1.68 | 1.76 | NS |
| Ductus Veno sus PI | 0.97 | 0.97 | 0.97 | NS |
| Descending Aorta PI | 1.99 | 1.94 | 2.11 | NS |
| ICT % | 6.56 | 7.27 | 7.54 | NS |
| IRT % | 11.93 | 12.30 | 16.82 ↑ | 0.0025* |
| ET % | 42.51 | 41.71 | 41.26 | NS |
| MPI | 0.44 | 0.48 | 0.60 ↑ | 0.0049* |
| E vel (cm/sec) | 12.25 | 11.32 | 11.46 | NS |
| A vel (cm/sec) | 40.14 | 37.27 | 41.36 ↑ | 0.0214* |
| E/A ratio | 0.30 | 0.31 | 0.27 ↓ | 0.0065* |
| OF peak velocity (cm/sec) | 39.92 | 36.56 | 41.05 ↑ | 0.0476* |

Median of the variables in each of the three groups is shown.
*Parameters showing significant values of lithium in comparison to control group, as based on non-parametric Kruskal Wallis test.
Abbreviations:
PI = pulsatility index,
ICT % = proportion of isovolemic contraction time in the cardiac cycle,
IRT % = proportion of isovolemic relaxation time in the cardiac cycle,
ET % = proportion of the ejection time in the cardiac cycle,
MPI = myocardial performance index,
E = inflow velocity during early ventricular filling,
A = inflow velocity during atrial contraction,
OF = ventricular outflow tract.

HCy Group Compared with Control Group

Except for the structural and valve defects described below, there were few statistically significant differences in myocardial performance between the HCy and control groups. As with Li, when one compares the mean values for outflow peak velocity, the minimum value was 18.53 cm/sec and the maximum 84.00 cm/sec. FIGS. 11E-M depicts the typical waveforms that were obtained. Thirty-nine (66%) embryos exposed acutely to HCy displayed valve regurgitation. SL valve regurgitation occurred in 53% of embryos, AV valve regurgitation in 10%, and both AV and SL valve regurgitation occurred in 3% of embryos. All control animals had normal Doppler patterns (FIG. 11A). In summary, cardiac valve defects developed at a similar rate in embryos following a single exposure to Li or HCy on E6.75. Based on statistically significant differences, acute Li exposure results in poorer myocardial performance than that observed with HCy.

Following echo monitoring on E15.5, placental weight and morphometric measurements of crown-rump length and body weight were obtained. With a single exposure to Li or HCy, all three morphometric measurements were significantly decreased compared with control embryos (Table 4). There were also significantly more resorptions with HCy (46%, n=27/59 embryos) than with Li exposure (24%, n=16/68 embryos). HCy administered on E6.75 induced valve defects in 66.1% of the embryos (39/59 embryos). Some litters were allowed to develop to E18.5. No recovery of development was apparent and the same valve defects were seen on E18.5 (data not shown) compared with those seen earlier in gestation, indicating that it was not only a delay in valve development that was monitored on E15.5.

TABLE 4

Summary of Folate Rescue of Li or HCy Effects on Mouse Heart Development

| | Valve Regurgitation | CRL (mm) | Body Weight (g) | Placenta Weight (g) | Resorptions |
|---|---|---|---|---|---|
| HCys | 39/59 (66.1%) | 13 | 0.35 | 0.11 | 27/59 (45.7%) |
| Li | 43/68 (63.2%) | 13.8 | 0.37 | 0.11 | 16/68 (23.5%) |
| NaCl | 0/42 | 15.2 | 0.41 | 0.13 | 0/42 |
| HCys + FA Rescue | 0/27 | 14.8 | 0.42 | 0.12 | 0/27 |
| Li + FA Rescue | 1/30 (3.3%) | 14.6 | 0.40 | 0.11 | 1/30 (3.3%) |

Pathological Assessment of HCy-Exposed Embryonic Hearts

On E15.5 (FIGS. 12A-C, control heart), HCy exposure was associated with right and left side cardiac hypertrophy, as evidenced by an increase in myocardial wall thickness (FIGS. 12D-L). The lumen often had a spongy appearance and was not distinctly evident. In embryos that displayed AV valve regurgitation upon echo monitoring, most tricuspid valve leaflets had not formed normally: the septal leaflet had not delaminated and it remained attached to a wide interventricular septum (compare the normal AV valves in FIG. 12A with the AV valve anomalies that are apparent in FIG. 12D, G). The embryo shown in FIGS. 12G-I displayed an echo pattern indicating both AV and SL valve regurgitation. Malformed and small aortic valves (AoV in H) and pulmonary valves (PV in I) were apparent. The embryonic heart shown in the sections in FIGS. 12J-L displayed an echo pattern that was indicative of SL valve stenosis. This was exemplified by a post-stenotic dilatation of the pulmonary artery, apparent in FIG. 12L. FIGS. 12M-O shows enlargements of valve regions of hearts with abnormal echo patterns. In summary, in addition to the general cardiac hypertrophy, the viable cardiac anomalies that were observed on E15.5 following a single HCy exposure on E6.75 related primarily to derivatives of the SHF, that is the outflow, the right ventricle, and the tricuspid and SL valves.

FA Supplementation Results in Normal Cardiac Function in Li- and HCy-Exposed Mouse Embryos The inventors found that rescue of normal cardiac function and valve defects is possible using FA supplementation with Li or elevated HCy exposure. Pregnant females were administered concomitantly with FA (125 µl at 75 µM) and HCy (75 µM), both intraperitoneally (i.p.), on E6.75. FA supplementation resulted in normal valve development and cardiac function, as determined by echocardiography in the HCy-exposed group (100%, n=27/27 embryos). However, FA supplementation provided on E6.75 normalized the effects of HCy, but not Li, exposure. Protection from Li exposure was obtained when FA was administered in the diet at 10 mg/kg throughout gestation, beginning with the presence of the vaginal plug on the morning of E0.5. Cardiac development then remained protected following Li exposure on E6.75. Normal valve formation and cardiac function were observed in 40 out of 41 embryos monitored (97.6%) as shown in Table 4. The one embryo that did not have a normal echo pattern displayed mild SL valve regurgitation. In summary, FA rescued cardiac function in the mouse embryo after acute Li or HCy exposure; however, Li induced defects required earlier and higher levels of FA supplementation for rescue.

The results indicate that Li, a glycogen synthase kinase-3 (GSK-3) inhibitor, and elevated HCy pose a serious threat to embryonic heart development, and that heart defects can be induced by only a single exposure during gastrulation and cardiac specification. In the early embryo, Wnt-β-catenin signaling in the cardiogenic crescent is required to maintain the undifferentiated state of cells. A key downstream intermediary of the active pathway is β-catenin, which accumulates in the cytoplasm and translocates to the nucleus to activate target genes. Preceding specification, the mesendoderm of the bilateral heart fields begins to express the Wnt antagonists Crescent and Dickkopf-1 (Dkk-1). These antagonists suppress canonical Wnt signaling, resulting in decreased β-catenin levels. As a result, genes associated with the induction of cardiogenesis, such as Hex and Isl1, are upregulated. Hex is expressed in the prechordal plate and primary heart field and Islet-1, a marker for the SHF, is synthesized (Cohen et al., 2007; Foley and Mercola, 2005). Both Li and HCy act to augment canonical Wnt signaling intracellularly, and are able to bypass the extracellular Dkk-1 or Crescent antagonism. Therefore, both Li and HCy exposure cause the Wnt-β-catenin pathway to remain active at a time when it would normally be downregulated in the early embryo. Thus, Li and HCy repress and delay the induction of Hex and Islet-1.

An association between HCy and FA deficiency and the Wnt-β-catenin pathway has been suggested previously from microarray analysis (Ernest et al., 2006; Liu et al., 2007). Additionally, analysis of tumorigenesis indicates that histone and DNA methylation are fundamental processes in the Wnt-β-catenin pathway and in gene target regulation (Sierra et al., 2006; Wohrle et al., 2007), including by β-catenin, adenomatous polyposis coli (APC) and Dkk-1 regulation (Csepregi et al., 2007; Willert and Jones, 2006). HCy and FA are central molecules in the synthesis path for S-adenosylmethionine (SAM), the universal methyl donor for biological methylation. FA deficiency causes HCy accumulation and produces a cellular deficit of SAM, thus limiting transmethylation reactions in the nucleus (Williams and Schalinske, 2007). Since β-catenin/lymphoid-enhancer factor (LEF) complex also regulates Isl1 expression (Lin et al., 2007), elevated HCy, through an epigenetic mechanism involving methylation, modulates the Wnt-β-catenin pathway and its target gene expression. As a corollary, FA rescue of the effects of Li and Wnt3A could be either at the level of methylation of β-catenin nuclear-binding proteins and/or at the level of DNA methylation, which affects the expression and synthesis of the antagonist Dkk-1. Either possibility can lead to potentiation of β-catenin target genes.

Li action starts in the cytoplasm but, through β-catenin that translocates to the nucleus, it also has a nuclear effect on gene expression. Li potentiates Wnt-β-catenin signaling by inhibiting GSK-3 and thereby stabilizing cytoplasmic β-catenin. In addition, Li suppresses the inositol-signaling pathway by inhibiting inositol monophosphatase and inositol polyphosphate 1-phosphatase (Belmaker et al., 1998). Wnt3A triggers G-protein-linked phosphatidylinositol signaling, transiently generating inositol polyphosphates, including inositol pentakisphosphate (IP5, also known as Ins(1, 3, 4, 5, 6)P5). IP5, in turn, inhibits GSK-3β activity (Gao and Wang, 2007). Blocking IP5 formation blocks β-catenin accumulation (Gao and Wang, 2007). Excess inositol may decrease IP5 formation by increasing the generation of di- and tri-polyphosphates. The association between the inositol phosphatidyl pathway and its intermediates with canonical Wnt signaling would explain the level of severity and the varied phenotypic cardiac defects that are induced by Li exposure in comparison with HCy. The additive/synergistic effect of myo-inositol and FA in protection from Li exposure suggests the involvement of this second messenger pathway in Wnt signaling. The FA effect occurs primarily at the nuclear level by protecting transmethylation reactions and by replenishing nucleotide pools, whereas the inositol effect is cytoplasmic, involving inositol polyphosphate signaling. As a result, the protective effects of FA and myo-inositol are additive/synergistic.

In addition to the cardiac hypertrophy, the viable cardiac valve anomalies seen on E15.5 following a single HCy exposure on E6.75 are related primarily to derivatives of the SHF (i.e. the outflow, the right ventricle, and the tricuspid and SL valves). In the embryonic heart, the valves are derived from the endocardial cushions, including in the outflow (Anderson et al., 2003). Expression of Isl-1, a marker for the SHF, is suppressed for a time period by a pulse of Li or HCy, thus the tricuspid and SL valve structures are affected downstream since these structures are derivatives of the right ventricle and outflow, respectively. Published evidence, using regulatory elements from the mouse Mef2c gene to direct the expression of Cre recombinase exclusively in the anterior heart field (AHF) and in its derivatives, indicates that the AHF enhancer is active in the future right ventricle, which includes the tricuspid valve region, and in the outflow tract, including the pulmonary valve (Verzi et al., 2005). Verzi et al. also reported that the endocardial endothelial cells of the right ventricle and outflow tract, which contribute to cushion formation, are marked by the Mef2c-AHFCre transgene. This cell lineage analysis showed that near the base of the heart, both Wnt1-Cre- and Mef2c-AHF-Cre-derived cells contributed to the smooth muscle cells of the pulmonary trunk and to the cells of the pulmonary valve leaflets. Wnt signaling plays an important role in controlling endothelial-to-mesenchymal transition (EMT) and in proliferation of the endocardial cushion cells. Therefore, early exposure to Li and HCy affects cells that are later modulated by Wnt signaling in the endocardial cushion during valve formation. Some of these cells in the endocardial cushions are suggested to derive from the prechordal plate that arises from cells at the embryonic midline during gastrulation (Chen et al., 2008; Seifert et al., 1993). Other cell types may also contribute in a cell-autonomous or non-cell autonomous manner.

The anterior-to-posterior nature of development and the specification of the first and second (anterior) heart fields are both crucial to understanding how the timing of a single-pulse exposure can vary the severity and nature of the defects. The first heart field and Hex appear to be induced slightly ahead of Islet-1. In the mouse model, a great number of right ventricular, AV and SL valve defects were observed thus in the viable embryos on E15.5, exposure at ~E6.75 targets SHF specification over that of the first heart field. With earlier exposure a high number of resorbed mouse embryos was observed, indicating lethal effects; or, as in the avian model, no or limited areas of bilateral cardiac tissue were apparent (Manisastry et al., 2006).

HCy- and Li-induced valve defects can be phenotypically subtle and may be missed by routine histological evaluation. The defects may relate only to differences in cell numbers that populate endocardial cushion regions. Thus, the echo data was essential to determine whether valve integrity had been functionally compromised. In general, more semilunar valve-outflow related abnormalities were detected with E6.75 exposure, as opposed to tricuspid valve abnormalities. This could have two reasons: (1) SL valve regurgitation in the presence of normally appearing AV valve tissue may be better tolerated by the embryo than a similar degree of AV valve regurgitation. (2) The tricuspid valve and the right ventricle develop earlier than the outflow region. Peak sensitivity for the right ventricle and tricuspid atrioventricular valve regions may relate to exposure at a slightly earlier embryonic period than is usually present in litters of embryos that were exposed at E6.75. Additionally the echo data provided information on placental blood flow that related to the intrauterine growth restriction (IUGR) that was observed. IUGR is associated generally with effects on placental and heart development (Corstius et al., 2005; Morrison et al., 2007). Wnt-β-catenin signaling and HCy impact placental development. The fact that embryos within a litter are not all at the same stage of development explains the variability and severity of heart defects, such as those observed with Ebstein's anomaly in the human population. Cardiac development relates to the timing of a single exposure, the exposure dose, and the developmental stage of a specific embryo within the relatively narrow window of early gestation.

Isovolemic contraction time (ICT) is a marker of systolic function. No difference was observed between Li or HCy in comparison to controls. Although hypertrophy of the myocardial wall was noted in almost in all HCy-exposed embryos, this phenotype does not necessarily affect cardiac function. Isovolemic relaxation time (IRT) as a percentage of the cardiac cycle is significantly changed in the Li-exposed embryos. The prolonged IRT is indicative of diastolic dysfunction of the myocardium and could result from an interference with Ca++ fluxes. Alternatively, prolonged IRT could be the result of diastolic pressure elevation in the systemic (pulmonary or aortic) vascular beds. Given that no statistical difference was observed in ICT and ET in both groups, the MPI essentially equals IRT for the Li group thus signifying either diastolic dysfunction or increased work load for the Li-exposed embryos.

Peripheral Doppler changes included increased placental resistance and increased lower body systemic resistance which is most likely caused by a decrease in the number of peripheral arteriolar vessels, placental and systemic. The uterine artery PI has been shown to have a significant negative correlation with the maternal heart rate in that the diastolic velocity increases in response to an increase in the heart rate, but the systolic velocity remains unchanged or decreases slightly (Ochi et al., 1999).

Given that not all embryos within a litter are at the same point in their development during acute exposure, median values were used in the statistical analysis. For example, in considering the outflow peak velocities and the minimum and maximum mean values obtained with exposure to Li or HCy, the outlying numbers were consistently and similarly high (98.5 or 84.0, respectively) or consistently close to the control minimal value (23.8 or 18.5, respectively). Control embryo outflow peak velocity had an average maximum value of 48.7 and minimum value of 22.2. These maximum and minimum values suggest that timing of exposure was different for these embryos. Exposure at younger, more susceptible stages, lead to the much higher values, and slightly older embryos with already more differentiated cardiac cell populations would no longer be affected and thus show normal control values. The median value would not reflect the effects on different stage embryos within one litter which can result in diverse changes in placental and heart development.

With both Li and HCy exposure, the placental weight was significantly less and the crown-rump length and body weight of the embryos were significantly reduced. Fetal growth restriction is associated with placental development and heart development (Corstius et al., 2005; Morrison et al., 2007). The results presented herein support that both Wnt/13-catenin signaling and homocysteine can impact placenta development (Kamudhamas et al., 2004; Mohamed et al., 2008).

There is a variability of effects with Li and HCy that is based on timing of peak exposure and dose. The epidemiological literature would most likely reflect only the viable defects seen after birth and would not reflect the embryonic lethal numbers. Some clinical studies have indicated an increase in spontaneous abortions with Li and HCy. The variability of effects based on timing of exposure, the early window at which peak susceptibility is observed (extrapolating to the human between days 16-19 after fertilization), and the absence of adverse effects detected after that developmental window has passed, have led to controversy surrounding teratogenicity of these environmental factors.

Epigenetic events occurring in utero with only one acute exposure can lead to changes in gene expression which can be persistent, even transgenerational, and can be modified by diet (Raykan et al., 2003). Since epigenetic processes are sensitive to change, they represent excellent targets to explain how environmental factors modify gene expression of key early signaling pathways, as the Wnt pathway, thus contributing to birth defects.

FA supplementation has been used since 1998 to reduce the occurrence of neural tube defects. The underlying basis of the protection is not known. FA deficiency- and elevated HCy-associated birth defects involve Wnt-β-catenin signaling, and prophylactic FA supplementation, at levels that are higher than those used currently for neural tube defect prevention, can prevent cardiac defects. Histone and DNA methylation are fundamental processes in the Wnt-β-catenin pathway and gene target regulation. HCy and FA molecules are intermediaries in the S-adenosylmethionine (SAM), the universal methyl donor, synthesis pathway. FA deficiency leads to HCy accumulation and a cellular deficit of SAM, thereby limiting transmethylation reactions in the nucleus. These reactions are involved in epigenetic modifications, meaning that nonlethal Li and HCy effects could extend beyond the period of embryogenesis.

Example II

Folate Protection of Fetal Alcohol Syndrome Related Cardiac Defects by Modulation of Wnt/β-Catenin Signaling Additionally, Wnt-β-catenin signaling can be a target for other environmental factors that induce cardiac and neural birth defects, for example alcohol (ethanol). Since epigenetic processes are sensitive to change, they represent excellent targets to explain how environmental factors modify the gene expression of key early signaling pathways, such as the Wnt pathway, and thus how they contribute to birth defects.

Figure 13:
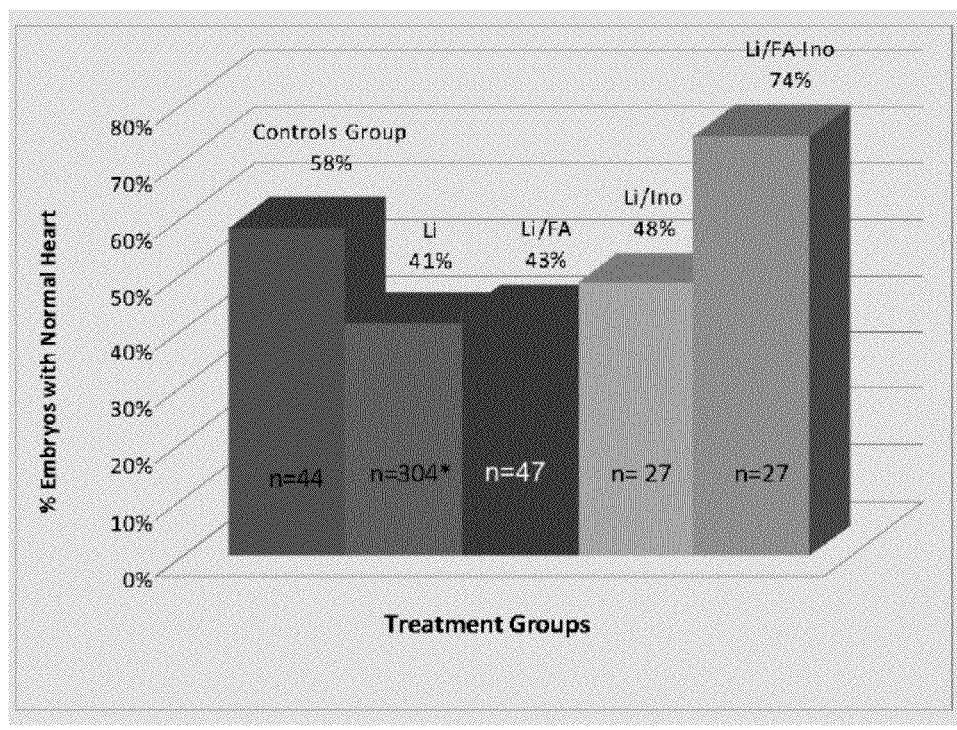
FIG. 13 is a graph showing the percentage of embryos with a normal heart according to treatment group. Asterisk (*) represents the numbers of embryos exposed to lithium included numbers previously published (Manisastry et al., 2006).
Figure 14:
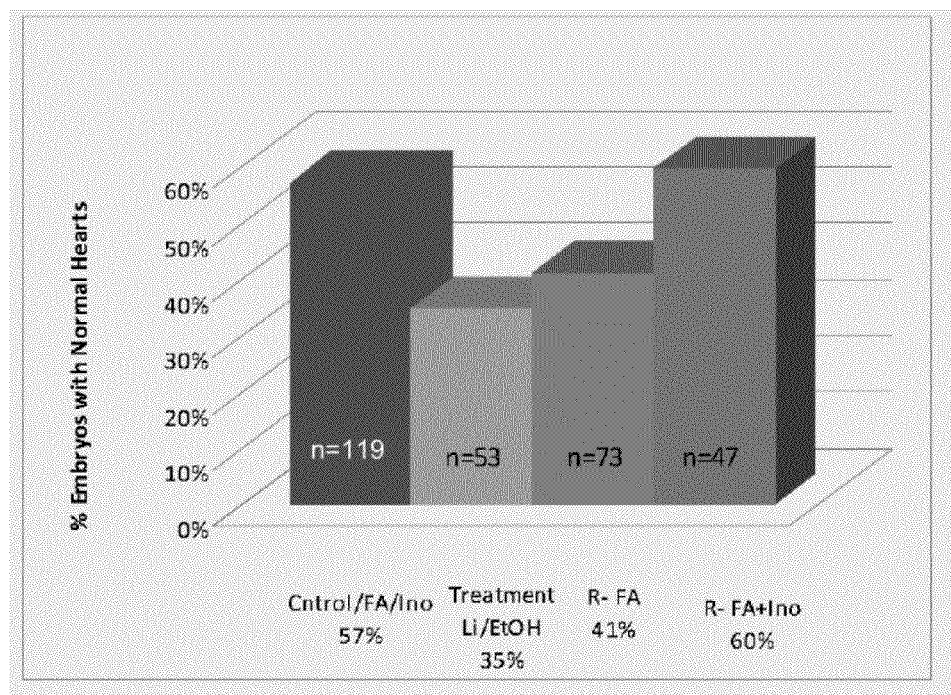
FIG. 14 is a graph showing the percentage of avian embryos with a normal heart according to treatment group— numbers of embryos exposed to FA, folic acid; EtOH, ethanol; R, rescue; Ino, myo-inositol.

The inventors have shown that elevated HCy and ethanol (EtOH) affects Wnt signaling during heart development to induce similar cardiac defects. The inventors have also previously shown that folic acid (FA) supplementation acts by overriding Wnt/β-catenin inhibition of the induction of cardiac gene expression in the heart fields. FA is known to protect against neural tube defects, and thus was tested for protective effects against ethanol potentiation of Wnt/β-catenin signaling during cardiac specification. As with lithium or Wnt3A exposure, the adverse effects of the environmental molecules can be rescued by addition of folate (FA) while the administration of FA concomitantly with myo-inositol produces synergistic effects of rescue and increased the percentage of embryos displaying normal heart development (FIGS. 13 and 14).

Fetal Alcohol Syndrome (FAS) is characterized by cardiac defects, fetal growth restriction, neurodevelopmental delays, and craniofacial malformations. In a recent epidemiological study periconceptional alcohol use was associated with cardiac birth defects, specifically conotruncal (outflow) defects and transposition of the great arteries. (GREWAL J, CARMICHAEL S L, MA C, LAMMER E J, SHAW G M. Maternal periconceptional smoking and alcohol consumption and risk for select congenital anomalies. Birth Defects Res A Clin Mol Teratol 2008; 82:519-26) The FAS-related outflow tract congenital birth defects are similar to those that we reported in animal models that were exposed acutely to the therapeutic drug lithium (Li) or to an elevated dose of the metabolic intermediary homocysteine (HCy). (HAN M, SERRANO M, LASTRA-VICENTE R, et al. Folate rescues lithium-, homocysteine-, and Wnt3A-induced vertebrate cardiac anomalies. Dis Models Mech 2009; 2:467-468) The inventors have demonstrated that a single exposure to Li or to HCy during gastrulation of vertebrate development induced cardiac valve defects by modulating canonical Wnt/β-catenin signaling. (HAN M, SERRANO M, LASTRA-VICENTE R, et al. Folate rescues lithium-, homocysteine-, and Wnt3A-induced vertebrate cardiac anomalies. Dis Models Mech 2009; 2:467-468; CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518) The inventors provided evidence that folic acid (folate, FA) alone or in combination with myo-inositol (FA/myo-Inos) can rescue the adverse effects on cardiac development that are induced by Li, HCy, and Wnt3A. (HAN M, SERRANO M, LASTRA-VICENTE R, et al. Folate rescues lithium-, homocysteine-, and Wnt3A-induced vertebrate cardiac anomalies. Dis Models Mech 2009; 2:467-468) It had been reported that EtOH suppresses Wnt/β-catenin signaling in bone marrow stromal cells (YEH C H, CHANG J K, WANG Y H, HO M L, WANG G J. Ethanol may suppress Wnt/beta-catenin Signaling on human bone marrow stroma cells. Clin Orthop. Relat Res. 2008; 2008:1047-1053) providing further credence to the possibility of alcohol interacting with the canonical Wnt pathway during cardiogenesis. Because of the similarities between cardiac birth defects associated with FAS and those induced by Li, HCy, or canonical Wnt exposure, the inventors investigated whether alcohol (ethanol, EtOH) impacts Wnt/β-catenin signaling and can be protected by FA or the combination of FA and inositol.

The mechanism by which alcohol induces congenital defects is not known, nor how early in gestation the damage occurs. The gastrulation stage of gestation was specifically targeted because it is an especially vulnerable period in pregnancy during which cardiac, neural crest, and neural cell fates are being specified. The cardiac effects of alcohol exposure during this early period of development have not been previously defined, specifically in relation to the canonical Wnt pathway, an important regulatory pathway in cardiac progenitor cell fate specification. (KWON C, CORDES K R, SRIVASTAVA D. Wnt/beta-catenin signaling acts at multiple developmental stages to promote mammalian cardiogenesis. Cell Cycle 2008; 7:3815-8; MANISASTRY S M, HAN M, LINASK K K. Early temporal-specific responses and differential sensitivity to lithium and Wnt-3A exposure during heart development. Dev Dyn 2006; 235:2160-74; UENO S, WEIDINGER G, OSUGI T, et al. Biphasic role for Wnt/beta-catenin signaling in cardiac specification in zebrafish and embryonic stem cells. Proc Natl Acad Sci USA 2007; 104:6685-9690) The specification signaling cascade involving canonical Wnt/β-catenin (MANISASTRY S M, HAN M, LINASK K K. Early temporal-specific responses and differential sensitivity to lithium and Wnt-3A exposure during heart development. Dev Dyn 2006; 235: 2160-74; UENO S, WEIDINGER G, OSUGI T, et al. Biphasic role for Wnt/beta-catenin signaling in cardiac specification in zebrafish and embryonic stem cells. Proc Natl Acad Sci USA 2007; 104:6685-9690; GARCIA-CASTRO M I, MARCELLE C, BRONNER-FRASER M. Ectodermal Wnt function as a neural crest inducer. Science 2002; 297:848-51; YAMAGUCHI T P. Heads or tails: wnts and anterior-posterior patterning. Current Biology 2001; 11:R713-R724) is active during gestation when a woman may be unaware she is pregnant. In the human, the targeted experimental window extrapolates to 16-18 days post conception.

The inventors found that exposure of vertebrate embryos by a single injection to binge-drinking ethanol levels induced cardiac and valve defects. The severity of anomalies is related to timing of exposure during cardiac specification. To initiate cardiogenesis, the canonical Wnt antagonist Dickkopf-1 acts extracellularly to upregulate Hex an inducer of cardiogenesis. Exposure of stage 4 chick and quail embryos to 30% EtOH suppressed Wnt/β-catenin modulated gene expression of Hex (a marker of the primary heart field) and of Islet-1 (a marker for the second heart field) within the cardiogenic crescent. The inventors found that FA or FA/myo-inositol is capable of protecting the embryo from ethanol's adverse effects on development.

Avian Model

White Leghorn chick (*Gallus gallus*, Charles River, MA) and quail (*Coturnix coturnix*, Strickland Farms, GA) embryos were used because of accessibility to precisely determine the embryonic stage. Heart development in the avian embryo is similar to that in the mouse and human. Stage 4 embryos were incubated on an agar-albumin medium for 8 or 24 hrs at 38° C. (HAMBURGER V, HAMILTON H L. A series of normal stages in the development of the chick embryo. J. Morphol. 1951; 88:49-92; DARNELL D K, SCHOENWOLF G C. Culture of Avian Embryos. In: Tuan R S, Lo C W, eds. Developmental Biology Protocols. Totowa, N.J.: Humana Press, 2000 (vol 1)) The teratogenic EtOH dose was determined to be 25-30% EtOH. Control embryos were incubated on physiological saline in agar-albumin medium. For avian folate (FA, Sigma) rescue experiments, FA was added to the agar-albumin at a dose of 1 µg/ml previously determined. (HAN M, SERRANO M, LASTRA-VICENTE R, et al. Folate rescues lithium-, homocysteine-, and Wnt3A-induced vertebrate cardiac anomalies. Dis Models Mech 2009; 2:467-468) Myo-inositol (myo-Inositol, Sigma) was used at 277 mmol/L. For in ovo exposure, EtOH was injected into the blunt end egg airspace at doses of 10% or 30% in physiological saline.

Mouse Model

The C57Bl/6 mouse strain (Jackson Laboratories) was used. Mice handling was according to protocols approved by USF-IACUC. Morning of the vaginal plug was defined as embryonic day (E) 0.5. Pregnant mice were administered a binge drinking level of EtOH (i.e., intraperitoneal, i.p., injections of 306 µl of 2.9 g EtOH/kg maternal weight administered at 3 PM and at 6 PM on E6.75); one i.p. injection of EtOH (3.5 g/kg; or 370 µl), or a higher dose of 4.5 g/kg. Only the two i.p. exposure dose on E6.75 led to healthy adult mice and induced defects in embryonic cardiovascular function. The two i.p. regimen was used throughout these analyses. On E15.5, the circulations of the pregnant mice and embryos were examined in utero using Doppler ultrasonography. (GUI Y H, LINASK K K, KHOWSATHIT P, HUHTA J C. Doppler Echocardiography of Normal and Abnormal Embryonic Mouse Heart. Ped. Res. 1996; 40:633-642; LINASK K K, HUHTA J C. Use of doppler echocardiography to monitor embryonic mouse heart function. Developmental Biology Protocols 2000; 1:245-252)

Folate Rescue Mouse Diet

Animal chow supplemented with 0.5 mg/kg or 6.2 mg/kg FA was prepared by Harlan Laboratories: These doses are based on human population trials for rescue of craniofacial anomalies. (CZEIZEL A E, TIMAR, L., SARKOZI, A. Dose-dependent effect of folic acid on the prevention of orofacial clefts. Pediatrics 1999; 104:e66) Control mice received the baseline diet containing 3.3 mg FA/kg: this dose maintains health of the pregnant dam, but does not rescue the cardiac defects. The calculations for FA level in the FA-supplemented diets were based on the metabolic body weight (BW) of mice because of the BW difference between humans and mice. (HEUSNER A A. What does the power function reveal about structure and function in animals of different size? Ann. Rev. Physiol. 1987; 49:121-133) For mice it is calculated as $BW^{0.75}$ (Harlan Laboratories, Madison, Wis.). Dams were randomly assigned to an experimental group supplemented with the high 10.5 mg/kg or moderate 6.2 mg/kg dose of FA, or to a control group that received normal chow (3.3 mg/kg). On E0.5 pregnant mice assigned to the experimental groups were placed on the FA supplemented diets. On E6.75 experimental pregnant females received EtOH or the control dams, physiological saline, by i.p injection. One group of control pregnant mice remained uninjected (the untreated control).

Doppler Ultrasonography

On E15.5 Doppler ultrasonographic (echo) examinations were performed with a 40 mHz transducer, as previously described using the Vevo 770 (VisualSonics, Toronto, CA) instrumentation. (HAN M, SERRANO M, LASTRA-VICENTE R, et al. Folate rescues lithium-, homocysteine-, and Wnt3A-induced vertebrate cardiac anomalies. Dis Models Mech 2009; 2:467-468; CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518) Control and experimental chick embryos were analyzed using digoxigenin-labeled riboprobes with alkaline phosphatase detection. (LINASK K K, HAN M D, ARTMAN M, LUDWIG C A. Sodium-calcium exchanger (NCX-1) and calcium modulation. NCX protein expression patterns and regulation of early heart development. Dev. Dynamics 2001; 221:249-264)

Histology and Microscopy

The avian embryos were processed for immunohistochemistry according to published protocol. (LINASK K K, TSUDA T. Application of plastic embedding for sectioning wholemount immunostained early vertebrate embryos. Methods Mol Biol 2000; 135:165-73) The antibody MF20 from D. A. Fischman was used for localization of sarcomeric myosin. This was obtained from the Developmental Studies Hybridoma Bank, developed under the auspices of National Institute of Child Health and Human Development and maintained by the University of Iowa, Dept of Biological Sciences, Iowa City, Iowa 52242). Mouse embryonic heart sections also were stained with hemotoxylin-eosin.

Alcohol exposure of avian embryos during gastrulation alters heart development and Wnt-modulated gene expression.

Figure 15:
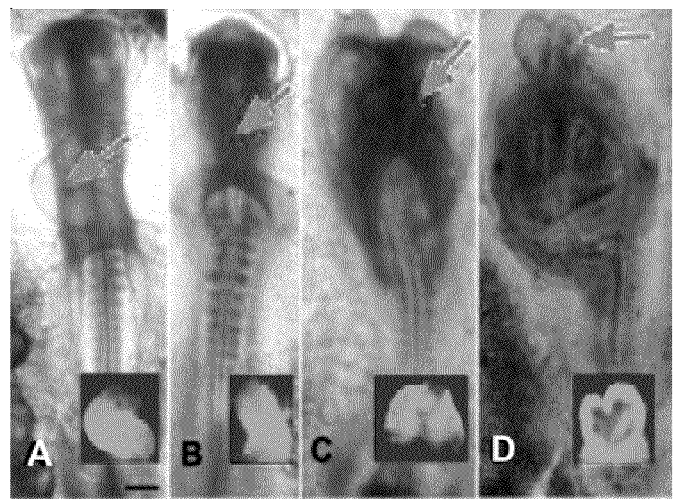
FIG. 15A-D are a series of images depicting EtOH induced cardiac malformations in the avian (quail) embryo after 24 hour incubation. Depicting heart shapes insets show fluorescent images of sarcomeric heavy chain localization (MF20 antibody) in the same hearts. A. Normal looping is shown of control heart. B. Embryo showing delayed development and a straight heart. C. Embryo displaying abnormal wide heart without fusion of the bilateral heart tubes. D. Embryo depicting cardiac tissue anterior to a truncated neural tube. Magnification bar (A) and for all images, 500 μm.
Figure 16:
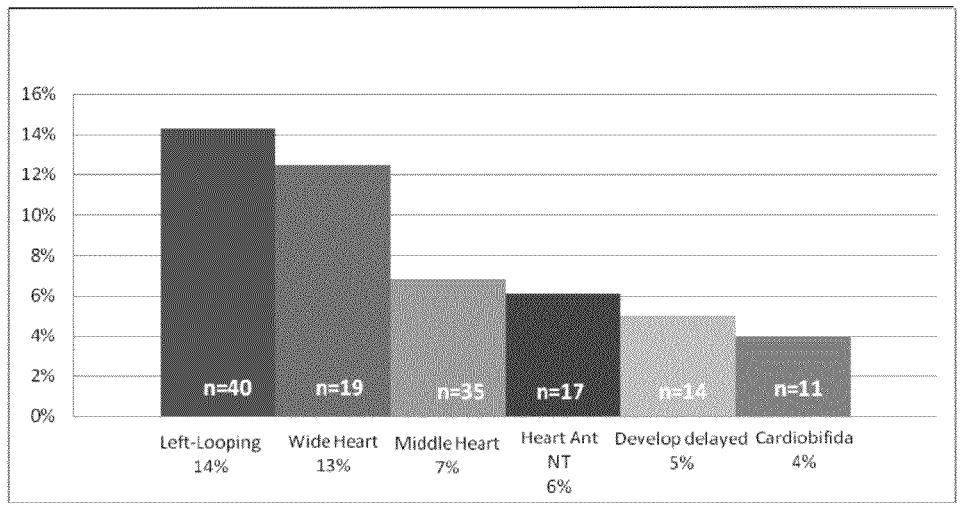
FIG. 16 is a graph depicting cardiac phenotypes with ethanol exposure in avian embryos.

Avian embryos exposed to EtOH in vitro at HH stage 4 displayed morphological defects of delayed growth and severe cardiac malformations (see FIG. 15A, control; 15B-D, EtOH exposed; FIG. 16). Embryonic heart shapes are shown in FIG. 15 (see arrows in FIGS. 15A through D); insets show the fluorescent images of sarcomeric heavy chain localization in the same hearts. FIG. 15A depicts normal dextral looping of the heart of a control embryo. FIG. 15B depicts an embryo showing delayed development and a straight tubular heart. FIG. 15C depicts an embryo displaying an abnormally wide heart due to lack of fusion of the bilateral heart tubes. FIG. 15D depicts an embryo with cardiac tissue situated seemingly anterior to a truncated neural tube. After 24 hrs, the early cardiac malformations included: wide hearts at embryonic middle, and cardia bifida, i.e., bilateral heart fields not fusing; cardiac tissue situated anterior to the head, signifying a truncation of the neural tube (NT) due to an inhibition of convergence-extension; and left-looping hearts arising from abnormal development of the second heart field. These defects most likely would be embryonic lethal.

Figure 17:
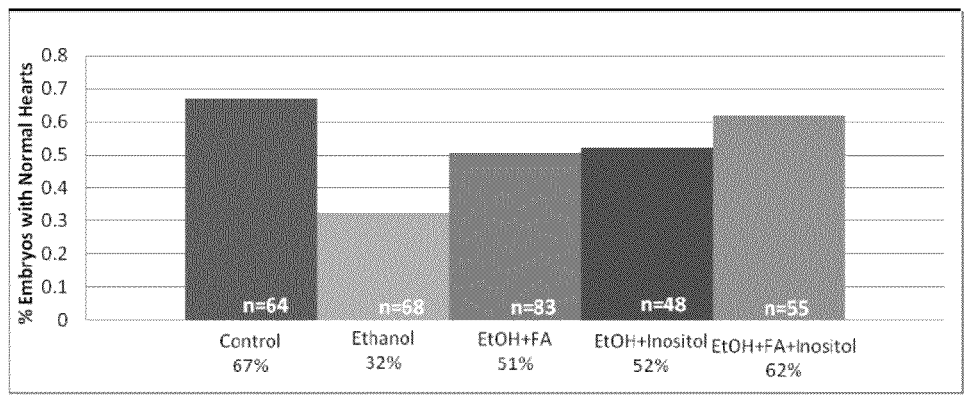
FIG. 17 is a graph depicting the percentage of stage 4 avian embryos with normal heart development after 24 hours incubation in the presence of ethanol with folate and/or myo-inositol supplementation.
Figure 18:
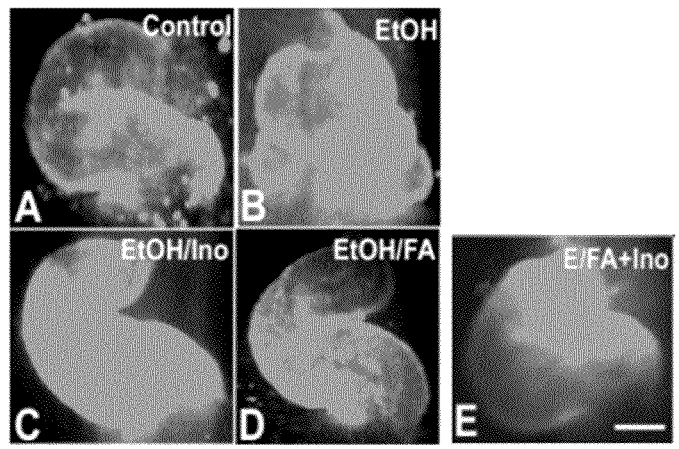
FIG. 18A-E are a series of images illustrating that FA or FA/myo-inositol (Ino) supplementation protects avian heart development after EtOH exposure at primitive streak stage. Avian hearts were immunostained for sarcomeric myosin heavy chain localization. Representative hearts for the different experimental groups are depicted in Figures A through E: (A) Control embryo, untreated; (B) EtOH only exposure; (C) EtOH exposure with high FA supplementation. (D) EtOH and myo-inositol only is protective; as well as (E) EtOH exposure with supplementation of combination of FA and myo-inositol. Magnification bar (E) and for all panels, 250 μm.

Using smaller quail eggs at stage 4, the inventors analyzed EtOH exposure effects in ovo by microinjecting 10%, 25% or 30% EtOH into the airspace at the blunt end of the egg. Ten percent EtOH had no adverse effects, but 25% and 30% EtOH produced cardiac valve anomalies in 68% of the embryos (32% normal). For both in vitro and in ovo regimens, administration of FA (10 mg/ml) concurrently with EtOH resulted in cardiac protection, with 51% displaying normal heart development. An additive protective effect occurred with the administration of FA/myo-inositol resulting in 62% normal embryos, close to the control level of 67% for this stage (FIG. 17, FIG. 18).

As shown in FIGS. 18A-E, avian embryo exposure to ethanol and FA affects heart development and Wnt-modulated gene expression. FA or FA/myo-inositol (Ino) supplementation protects avian heart development after EtOH exposure at primitive streak stage. Quail embryonic hearts were immunostained for sarcomeric myosin heavy chain localization. Representative hearts for the different experimental groups are depicted in FIGS. 18A through E: (A) Control embryo, untreated; (B) EtOH only exposure; (C) EtOH exposure with high FA supplementation. (D) EtOH and myo-inositol only is protective; as well as (E) EtOH exposure with supplementation of combination of FA and myo-inositol.

Figure 19:
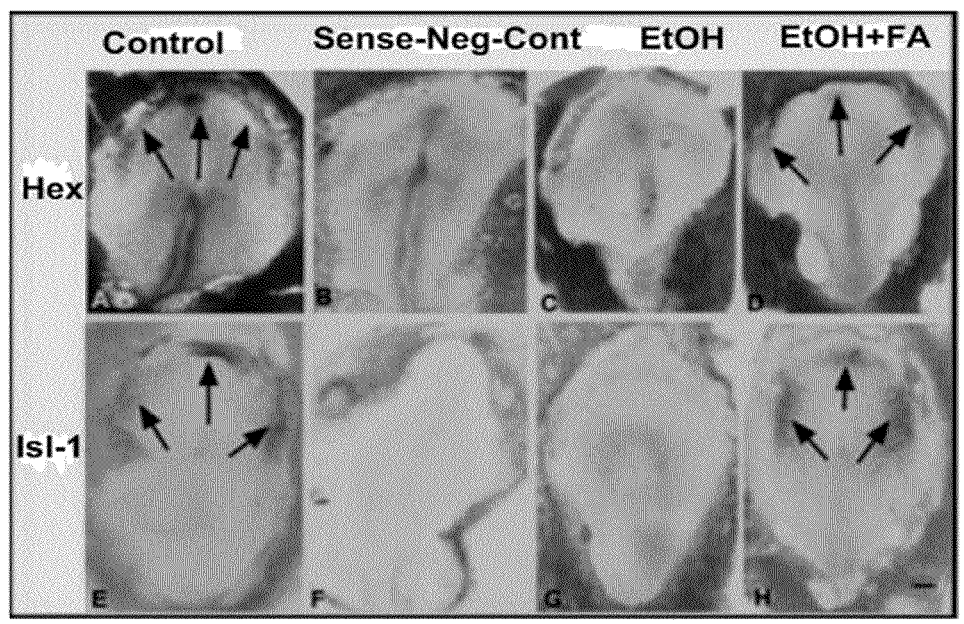
FIG. 19A-H are a series of images depicting the in situ hybridization of avian embryos. Suppression of Hex and Isl-1 expression was found after EtOH exposure of avian embryos at HH stage 4 with and without FA and after 8 hour incubation. Hex (A-D) and Isl-1 (E-H) expression are shown in the primary and second heart fields, respectively. A, D, Control expression; B, F, Sense probe, negative control; C, G, EtOH exposure only shows decreased or no signal; D, H, EtOH with FA supplementation restores gene expression to control levels. Magnification bar (H) for all panels, 200 μm.

The inventors found that EtOH alters the gene expression patterns of two Wnt-modulated genes critical in cardiac cell specification: Hex, a homeodomain gene involved in primary heart field specification signifying the left ventricle and part of the right, and Islet 1 (Isl-1), a marker of the second heart field (SHF) that gives rise to the outflow part of the right ventricle, including the tricuspid valve, and the conotruncal region and its derivatives. (VERZI M P, MCCULLEY D J, DE VAL S, DODOU E, BLACK B L. The right ventricle, outflow tract, and ventricular septum comprise a restricted expression domain within the secondary/anterior heart field. Dev Biol 2005; 287:134-45) Upon 30% EtOH exposure in the avian model, culture medium supplementation with FA, with and without myo-inositol, resulted in normal expression of the cardiac inducers Hex and Islet-1 often at higher levels in the chick heart fields than observed in the physiological saline exposed, control group. FIGS. 19A-H depict the in situ hybridization of avian embryos showing the suppression of Hex and Isl-1 expression after EtOH exposure of avian embryos at HH stage 4 with and without FA after an 8 hour incubation. FIGS. 19A-H depict Hex (FIGS. 19A-D) and Isl-1 (FIGS. 19E-H) expression in the primary and second heart fields, respectively. Hex and Isl-1 expression in control embryos is shown in FIGS. 19A and 19E, respectively (sense negative control, 19B and 19F). In comparison, EtOH exposure suppressed the canonical Wnt-modulated gene expression of Hex (19C) and of Isl-1 (19G). With FA supplementation, both gene expression patterns were normalized (19D and 19H) and appeared often at higher intensity levels than that seen in control embryos. In summary, FA suppressed EtOH inhibition and protected the cardiac progenitor cell expression of two early genes critical in cardiac induction.

Mouse Embryo Ethanol Exposure and Folate Protection

The inventors discovered that FA protects mouse hearts from the known adverse effects of an exposure to a binge-drinking dose of EtOH targeting a 3-hour window of gastrulation. Animal chow supplemented with the high 10.5 mg/kg diet or the moderate 6.2 mg/kg dietary dose of FA was fed to pregnant females starting on the morning of the vaginal plug. The pregnant mice were injected by i.p. with EtOH or control saline on E6.75 (gastrulation) at a level commonly used as a model of human binge drinking (HAN M, SERRANO M, LASTRA-VICENTE R, et al. Folate rescues lithium-, homocysteine-, and Wnt3A-induced vertebrate cardiac anomalies. Dis Models Mech 2009; 2:467-468; CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518; KOTCH L, SULIK K. Patterns of ethanol-induced cell death in the developing nervous system of mice: neural fold states through the time of anterior neural tube closure. Int J Dev Neurosci 1992; 10:273-279; WEBSTER W, WALSHO D, MCEWEN S, LIPSON A. Some teratogenic properties of ethanol and acetaldehyde in C57BL/6J mice: implications for the study of the fetal alcohol syndrome. Teratology 1983; 27:231-243)

Two injections straddling the previously defined target window were used, because one i.p. injection of 3.5 g/kg did not produce any abnormalities. One i.p. injection of 4.5 g/kg EtOH resulted in cardiac abnormalities, but the pregnant mouse appeared sickly. By administering two i.p. injections of 2.9 g/kg each (administered 3 hours apart) on E6.75, the pregnant dam remained healthy, but embryonic/fetal abnormalities were prevalent. Therefore, the two i.p. injection regimen was used in all subsequent studies using the mouse model.

More than a week after EtOH exposure, 87% of the mouse embryos had cardiac defects. The myocardial wall often appeared thinner and in these hearts trabeculation was decreased in comparison to control hearts. With acute exposure on E6.75 predominantly semilunar (aortic and pulmonary) valve regurgitation was noted (77%), with a lower percentage of embryos displaying atrioventricular (tricuspid) valve defects. Placental function was also compromised. Effects on heart and placental function were identified non-invasively by monitoring blood flow patterns using echocardiography on E15.5 (Tables 5, 6 and 7).

TABLE 5

Percentage E15.5 Mouse Embryos with Valvular Regurgitation and FA Rescue

| Valvular Regurgitation | control | Ethanol* | | EtOH* + FA (10.5 mg/kg) | EtOH* + FA (6.2 mg/kg) | |
|---|---|---|---|---|---|---|
| # Embryos | 42 | 30 | | 23 | 12 | |
| SLV | 0 | 23 | 77% | 0 | 6 | 50% |
| AVVR | 0 | 2 | 7% | 0 | 1 | 17% |
| SLV + AVVR | 0 | 1 | 3% | 0 | 0 | 0% |
| Total | 0% | 87% | | 0% | 58% | |
| Abnormal Rescue | NA | NA | | 100% | Partial rescue | |

*Ethanol Dose: i.p. twice (3 and 6 PM) on E6.75; 2.9 g/kg

Abbreviation:

NA, not applicable

All parameters of cardiac and placental function analyzed were significantly different in embryos exposed to in utero EtOH compared with non-exposed embryos (Table 6). Interestingly, pregnancies of dams that received injections of the vehicle, physiological saline, had significant changes in placental, but not cardiac, function compared with pregnancies of uninjected dams which can be due to the stress associated with injection. Physiological saline injections of FA on E6.75 produced a significant decrease in the length of the cardiac cycle and the E/A ratio remained decreased and similar to values with EtOH exposure, compared with untreated control embryos. Parameters associated with placental function remained increased which may indicate an increase in vascular resistance. Based on echo parameters, FA significantly protected the heart from valve dysmorphogenesis, and improved cardiac function to near normal levels in several categories. In all experimental groups, placental function remained significantly altered.

TABLE 6

Embryonic Mouse Heart (E15.5) Dopplar Ultrasound Parameters After Ethanol Exposure

| Parameters | Control | EtOH | | NaCl Inject control | | EtOH + FA | | FA | |
|---|---|---|---|---|---|---|---|---|---|
| No. Embryos | n = 24 | n = 30 | p-value* | n = 78 | p-value* | n = 24 | p-value* | n = 32 | p-value* |
| RR (ms) | 345 | 293 | 0.0023 | 331 | NS | 303 | 0.0445 | 314 | 0.0237 |
| HR (bpm) | 174 | 205 | 0.0025 | 182 | NS | 198 | NS | 191 | NS |
| ICT % | 6.85 | 10.09 | 0.0118 | 7.44 | NS | 8.91 | NS | 7.32 | NS |
| IRT % | 11.78 | 14.93 | 0.0002 | 11.37 | NS | 13.40 | NS | 12.82 | NS |
| MPI | 0.47 | 0.62 | 0.0004 | 0.46 | NS | 0.53 | 0.0499 | 0.50 | NS |
| OF (cm/sec) | 36.07 | 26.37 | 0.0093 | 34.90 | NS | 23.71 | <0.0001 | 34.30 | NS |
| E/A Ratio | 0.32 | 0.29 | 0.0106 | 0.31 | NS | 0.31 | NS | 0.28 | 0.0158 |
| DAPI | 1.46 | 1.73 | 0.0029 | 1.73 | 0.0025 | 1.84 | 0.0006 | 1.82 | 0.0005 |
| UAPI | 1.32 | 1.75 | <0.0001 | 1.65 | 0.0003 | 1.89 | <0.0001 | 1.71 | <0.0001 |
| DVPI | 0.85 | 1.21 | <0.0001 | 1.01 | 0.0003 | 1.22 | <0.0001 | 1.04 | <0.0001 |

Median of the variables in each of the groups is shown.
*Parameters showing significant values of ethanol (EtOH) exposure in comparison to untreated control group, as based on non-parametric Kruskal Wallis test. Significance (p-value) is based on values <0.05.
Abbreviations:
FA, folic acid;
HR, heart rate;
RR, cardiac cycle length;
PI = pulsatility index;
ICT % = proportion of isovolemic contraction time in the cardiac cycle;
IRT % = proportion of isovolemic relaxation time in the cardiac cycle;
MPI = myocardial performance index;
E = inflow velocity during early ventricular filling;
A = inflow velocity during atrial contraction;
OF = ventricular outflow tract;
DA, Descending Aorta;
UA, umbilical artery;
DV, ductus venosus.

Figure 20:
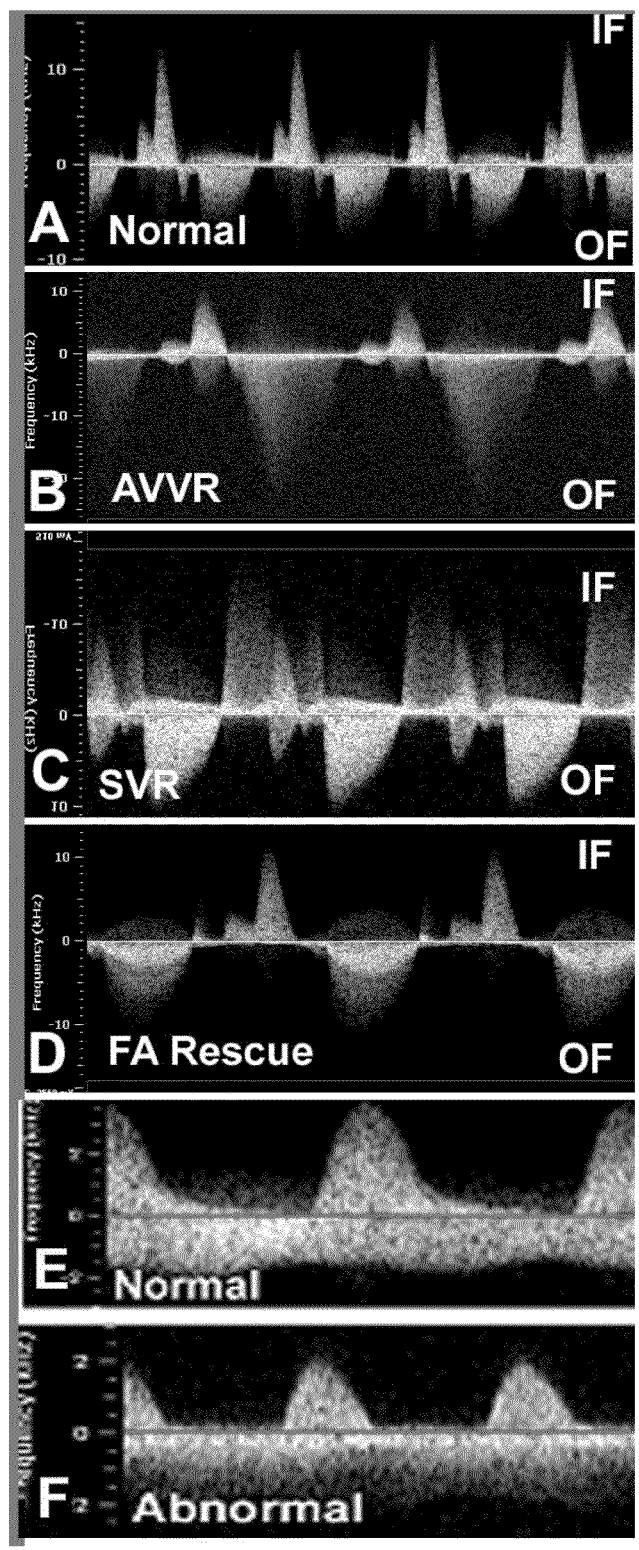
FIG. 20A-F are a series of images depicting echocardiography (echo) of embryonic mouse heart function. Defined abnormal Doppler ultrasound patterns of blood flow on ED 15.5 was shown, after EtOH exposure at binge-drinking levels was administered on embryonic day (ED) 6.75 of gestation. IF refers to inflow, and OF, outflow patterns. (A) Normal pattern depicts untreated, control heart; (B-C) EtOH-exposed embryonic heart displaying atrioventricular (AV) valve regurgitation (VR) or semilunar valve regurgitation (SVR), respectively. (D) Preservation of normal cardiac echo pattern with FA supplementation with EtOH exposure. (E) Embryo displaying normal umbilical artery blood flow is shown; (F) An embryo displaying abnormal umbilical artery blood flow after earlier EtOH exposure.

The echocardiography patterns that defined valve defects are depicted in FIG. 20. As shown in FIG. 20, mouse embryo exposure to ethanol results in valve regurgitation and administration of FA restores the normal cardiac echo pattern. Echocardiography (echo) of embryonic mouse heart function illustrated abnormal Dopplar ultrasound patterns of blood flow on E15.5, after EtOH exposure at binge-drinking levels was administered on E6.75 of gestation. A normal echo pattern is shown in panel 20A. Abnormal patterns with EtOH exposure revealed AV valve regurgitation (AVVR, 20B) or semilunar valve regurgitation (SVR, 20C). EtOH with FA supplementation restored the normal inflow and outflow patterns (20D). Compared with the normal pattern (20E), EtOH exposure produced abnormal umbilical artery blood flow (20F), indicating adverse effects on placental development. As shown in FIGS. 20A-F, FA is capable of rescuing the cardiac echo pattern embryos that are exposed to EtOH. The affected EtOH-exposed embryos displayed significant intrauterine growth retardation and smaller placental size (Table 7).

TABLE 7

Embryonic Mouse (E15.5) Morphometric Parameters with Ethanol Exposure

| Parameters | Litters/ #Embryos | CRL (mm) | Body Weight (g) | Placenta Weight (g) |
|---|---|---|---|---|
| 0.9% NaCl control | 8/42 emb. | 15.20 | 0.41 | 0.13 |
| Ethanol* | 4/30 emb. | 12.63 | 0.37 | 0.10 |
| Ethanol** | 2/10 emb. | 11.40 | 0.35 | 0.09 |
| EtOH* + FAD (10.5 mg/Kg) | 5/23 emb. | 14.43 | 0.44 | 0.12 |
| EtOH* + FAD (6.2 mg/Kg) | 3/12 emb. | 12.42 | 0.36 | 0.10 |

TABLE 7-continued

Figure 21:
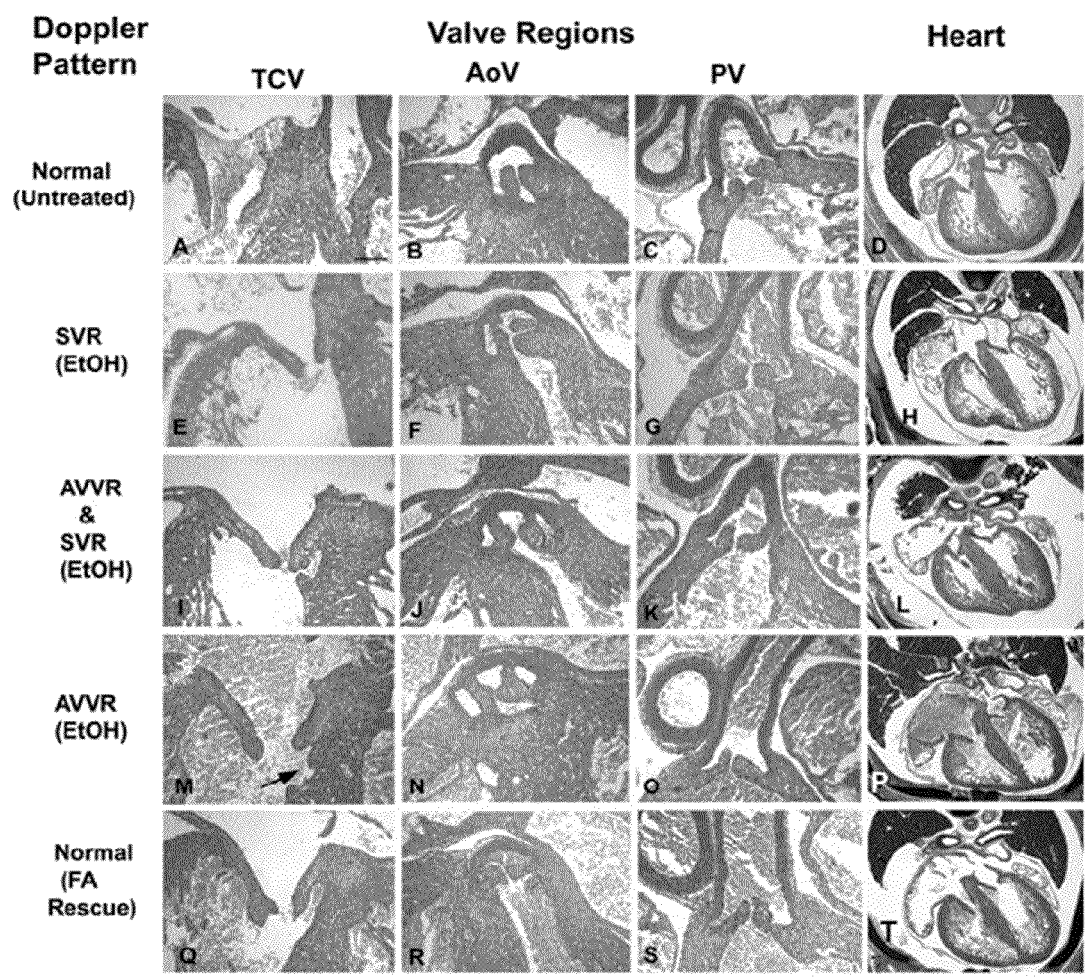
FIG. 21A-T are a series of images depicting histological sections through valve regions of control and of EtOH-exposed E15.5 mouse hearts showing abnormal echo patterns. Doppler results are shown in left column next to the row of images for that same heart. Sections showing full heart image for each experimental treatment are shown in last column. Sections were cut through tricuspid (TCV column), aortic (AoV column) and pulmonary (PV column) valves: Images are (A-D) normal control embryo; (E-H) acute EtOH exposed embryo displaying SV regurgitation (SVR); (I-L) acute EtOH exposed embryos displaying both AV and SV regurgitation; (M-P) acute EtOH exposed embryos displaying AV valve regurgitation; and (Q-T) FA-rescued embryos with EtOH exposure displaying normal echo pattern, valves, cardiac wall and trabeculation. Magnification bar (A) and for all valve related panels, 100 μm

Dose of Ethanol:
*30% EtOH: 2.9 g/Kg of maternal weight; twice by i.p. Volume: 306 μL @ 3:00 PM and 6:00 PM (E6.75)
**30% EtOH: 3.5 g/Kg of maternal weight; once by i.p. Volume: 370 μL @ 6 PM only, (E6.75)
Abbreviations:
CRL, crown to rump length;
EtOH, ethanol;
FAD, folic acid diet Pregnant mice fed the high FA supplemented diet (10.5 mg/kg) and administered the two i.p. EtOH injections on E6.75 had embryos with normal heart function, as defined by echocardiography on E15.5. In the 5 litters of dams in the high FA groups, there was only one resorbed embryo. When the diet of the pregnant mouse was supplemented with the moderate dose (6.2 mg/kg), only partial prevention occurred with 58% of embryos displaying valve regurgitation. The control group (FIG. 21A-D), the EtOH-exposed embryonic hearts displaying valve regurgitation (FIGS. 21E-P) and the embryonic hearts within the high FA-supplemented diet, rescued, group (FIG. 21Q-T) were processed for histology of the atrioventricular (tricuspid, TCV) and semilunar (aortic, AoV; pulmonary, PV) valve regions (FIG. 21). In comparison with normal valve regions of the control group (21A-D), the alcohol exposed embryos that displayed semilunar valve regurgitation (SVR), the aortic valve (AoV, 21F) and pulmonary valve regions (PV, 21G) appeared more disorganized than in the control. The heart wall often appeared thinner in places and showed less trabeculation (compare 21H and P hearts after ethanol exposure, with control 21D heart). Hearts showing AV valve regurgitation (AVVR) with echo monitoring (FIGS. 21I-21P), when viewing adjacent sections, the septal leaflet of the tricuspid valve was not clearly delaminated or the interventricular septal wall displayed outpocketings (arrows) and was not smooth The aortic valve leaflets often appeared malpositioned (21F, J). FA normalized valve function and histology (21Q-S). Heart wall and trabeculation appeared now normal (21T). In summary, dietary FA provided at a high, but not moderate dose at the time of conception and continued to the time of acute EtOH exposure, provided protection of normal cardiac valve development and returned cardiac function to near-control levels. Placental flow continued to show increased vascular resistance.

The mouse and avian results taken together illustrate that acute EtOH exposure potentiates Wnt/β-catenin inhibition of early cardiogenesis by suppressing expression of two cardiac inducing molecules, Hex and Isl-1. (CAI C L, LIANG X, SHI Y, et al. Isl1 identifies a cardiac progenitor population that proliferates prior to differentiation and contributes a majority of cells to the heart. Dev Cell 2003; 5:877-89; FOLEY A C, MERCOLA M. Heart induction by Wnt antagonists depends on the homeodomain transcription factor Hex. Genes Dev 2005; 19:387-96) These genes are activated when canonical Wnt signaling is inhibited by Wnt antagonists. The inventors have demonstrated that high dietary folate taken from time of conception can prevent the alcohol-induced heart defects. These results support a recent Canadian epidemiological human study reporting a 6% yearly decrease in the prevalence of severe heart defects in the seven years after FA fortification. (IONESCU-ITTU R, MARELLI A, MACKIE A S, PILOTE L. Prevalence of severe congenital heart disease after folic acid fortification of grain products: time trend analysis in Quebec, Canada. BMJ 2009; 338:b1673) The inventors have discovered that FA prevention of heart defects expands to the fetal alcohol syndrome in mammals, but indicates that folate protection is optimal at a higher dose than the current recommended dietary intake (400 μg/day). (BAILEY L B. Folate and vitamin B12 recommended intakes and status in the United States. Nutr Rev 2004; 62:S14-20; discussion S21) Women who have delivered an infant with a neural tube defect are currently advised to take 4 mg FA/day, a level lower than the moderate dose that provided only partial cardiac protection in our study.

Previous studies using the avian model have addressed the effects of EtOH at cardiac developmental time periods on day 3 and later. (CAVIERES M F, SMITH S M. Genetic and developmental modulation of cardiac deficits in prenatal alcohol exposure. Alcohol Clin Exp Res 2000; 24:102-9; MEMON S, PRATTEN M K. Developmental toxicity of ethanol in chick heart in ovo and in micromass culture can be prevented by addition of vitamin C and folic acid. Reprod. Toxicol. 2009; doi:10.1016/j.reprotox.2009.03.018) However, the previous studies did not examine the specifically targeted gastrulation at HH (Hamburger and Hamilton staging (HAMBURGER V, HAMILTON H L. A series of normal stages in the development of the chick embryo. J. Morphol. 1951; 88:49-92)) stage 4 which coincides with Wnt/13-catenin signaling cell fate decisions. (MARVIN M J, DI ROCCO G, GARDINER A, BUSH S M, LASSAR A B. Inhibition of Wnt activity induces heart formation from posterior mesoderm. Genes Dev 2001; 15:316-27) Gastrulation is a most critical early period, however, because pregnancy may be yet unrecognized and drug intake, alcohol ingestion, and smoking may be ongoing. At later stages, Wnt signaling is active in the outflow and phenotypically developing valves (CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518; COHEN E D, WANG Z, LEPORE J J, et al. Wnt/beta-catenin signaling promotes expansion of Isl-1-positive cardiac progenitor cells through regulation of FGF signaling. J Clin Invest 2007; 117:1794-804; HURLSTONE A F, HARAMIS A P, WIENHOLDS E, et al. The Wnt/beta-catenin pathway regulates cardiac valve formation. Nature 2003; 425:633-7) and may be also responsible for anomalies occurring from later exposures. C57BL/6J mice and White Leghorn chickens were used because these strains carry a high-risk for FAS related birth defects. (CAVIERES M F, SMITH S M. Genetic and developmental modulation of cardiac deficits in prenatal alcohol exposure. Alcohol Clin Exp Res 2000; 24:102-9; DATTA S, TURNER D, SINGH R, RUEST LB, PIERCE W M, JR., KNUDSEN T B. Fetal alcohol syndrome (FAS) in C57BL/6 mice detected through proteomics screening of the amniotic fluid. Birth Defects Res A Clin Mol Teratol 2008; 82:177-86)

In comparison with previous studies, the inventors used acute exposures, targeted gastrulation at E6.75, and used noninvasive echocardiography to identify embryos that developed abnormal AV and semilunar valves. E6.75 is a much earlier developmental stage than was previously thought to be linked with valve development. (ARMSTRONG E J, BISCHOFF J. Heart valve development: endothelial cell signaling and differentiation. Circ Res 2004; 95:459-70; BUTCHER J T, MARKWALD R R. Valvulogenesis: the moving target. Philos Trans R Soc Lond B Biol Sci 2007; 362:1489-503; DE LANGE F J, MOORMAN A F, ANDERSON R H, et al. Lineage and morphogenetic analysis of the cardiac valves. Circ Res 2004; 95:645-54) Several explanations can give rise to the more viable defects, i.e. of the right ventricle, including tricuspid valve, defects, as well as those of the outflow tract. One explanation is that the second/anterior heart field can be delayed in its development due to a suppression of Isl-1, a marker of the second heart field (SHF). In a recent cell lineage analysis, the cells of the SHF contribute to the right ventricle, tricuspid valve, and OFT tract, including aortic and pulmonary valve regions. (VERZI M P, McCULLEY D J, DE VAL S, DODOU E, BLACK B L. The right ventricle, outflow tract, and ventricular septum comprise a restricted expression domain within the secondary/anterior heart field. Dev Biol 2005; 287:134-45)

Another explanation relates to the subpopulation of cells undergoing epithelial-mesenchymal transformation (EMT) in the endocardial cushion regions that give rise to valves and that can be derived from prechordal plate cells that are present during gastrulation, (CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518; KIRBY M L, LAWSON A, STADT H, et al. Hensen's node gives rise to the ventral midline of the foregut, implications for organizing head and heart development. Dev Biol 2003; 253:175-188) express Hex and Dickkopf1 (Dkk1), and migrate into the endocardial endothelium. (KIRBY M L, LAWSON A, STADT H, et al. Hensen's node gives rise to the ventral midline of the foregut, implications for organizing head and heart development. Dev Biol 2003; 253:175-188) With canonical Wnt potentiation using Li, the prechordal plate cells stopped migrating. (CHEN J, HAN M, MANISASTRY S M, et al. Molecular effects of lithium exposure during mouse and chick gastrulation and subsequent valve dysmorphogenesis. Birth Defects Res A Clin Mol Teratol 2008; 82:508-518)

The observed AV valve regurgitation can result from: (1) increased afterload; (2) right ventricular dysfunction; or (3) tricuspid valve dysmorphology. In regards to increased afterload, the EtOH-exposed mouse embryos displayed smaller placentas and intrauterine growth retardation in comparison to the control embryos. The tricuspid valve regurgitation observed in the fetal mouse can reflect the noted increased placental resistance and thus increased afterload. The placental effects also can be associated with the low birth weight, preterm birth, and spontaneous abortions that occur with prenatal alcohol exposure in humans. (BAILEY B, SOKOL R. Pregnancy and alcohol use: Evidence and recommendations for prenatal care. Clin Obstet Gynecol 2008; 51:436-444) Additionally, Wnt signaling is known to be important in placentation. (SONDEREGGER S, HUSSLEIN H, LEISSER C, KNOFLER M. Complex expression pattern of Wnt ligands and frizzled receptors in human placenta and its trophoblast subtypes. Placenta 28, Suppl A. 2007; 21:S97-S102) Right ventricular dysfunction or tricuspid valve regurgitation can arise from EtOH delaying Isl-1 expression during SHF specification described above, suppressing normal activation of downstream signaling pathways. Even subtle local changes in the right ventricular myocardium/endocardium or in valve leaflets that are not apparent morphologically can lead to AV regurgitation. Which types of right ventricular or outflow tract defects are dominant and their severity relate to timing and level of alcohol exposure within a relatively narrow, sensitive window of early gastrulation coinciding with cardiac SHF specification.

Ethanol maintaining the cardiac precursor state and folate protecting cardiac cell differentiation, may involve one-carbon metabolism and epigenetic regulation. (WANG J, ALEXANDER P, WU L, HAMMER R, CLEAVER O, MCKNIGHT SL. Dependence of mouse embryonic stem cells on threonine catabolism. Science 2009; 325:435-439; SIERRA J, YOSHIDA T, JOAZEIRO C A, JONES K A. The APC tumor suppressor counteracts beta-catenin activation and H3K4 methylation at Wnt target genes. Genes Dev 2006; 20:586-600; WOHRLE S, WALLMEN B, HECHT A.

Differential control of Wnt target genes involves epigenetic mechanisms and selective promoter occupancy by T-cell factors. Mol Cell Biol 2007; 27:8164-77) Acetyl CoA is present at high levels in embryonic stem (ES) cells relative to differentiating cells. (WANG J, ALEXANDER P, WU L, HAMMER R, CLEAVER O, MCKNIGHT S L. Dependence of mouse embryonic stem cells on threonine catabolism. Science 2009; 325: 435-439) Degradation of ethanol by alcohol dehydrogenase to acetaldehyde and subsequently to acetyl-CoA may favor the undifferentiated state and downstream, to canonical Wnt signaling. As ES cells differentiate, methyltetrahydrofolate (MTHF) was predominant. (WANG J, ALEXANDER P, WU L, HAMMER R, CLEAVER O, MCKNIGHT S L. Dependence of mouse embryonic stem cells on threonine catabolism. Science 2009; 325:435-439) FA supplementation would favor methyl MTHF production and enable transitioning toward differentiation. Folate protection can also involve epigenetic regulation of Wnt/β-catenin signaling. (SIERRA J, YOSHIDA T, JOAZEIRO C A, JONES K A. The APC tumor suppressor counteracts beta-catenin activation and H3K4 methylation at Wnt target genes. Genes Dev 2006; 20:586-600; WOHRLE S, WALLMEN B, HECHT A. Differential control of Wnt target genes involves epigenetic mechanisms and selective promoter occupancy by T-cell factors. Mol Cell Biol 2007; 27:8164-77)

Within promoter regions of β-catenin target genes, histone methylation or deacetylation states are important in epigenetic regulation (WOHRLE S, WALLMEN B, HECHT A. Differential control of Wnt target genes involves epigenetic mechanisms and selective promoter occupancy by T-cell factors. Mol Cell Biol 2007; 27:8164-77; LIU Z, LI T, LIU Y, et al. WNT signaling promotes Nkx2.5 expression and early cardiomyogenesis via downregulation of Hdac1. Biochim Biophys Acta 2009; 1793:300-11) and in cell fate determination in development. (KIEFER J. Epigenetics in Development. Dev Dynamics 2007; 236:1144-1156; SOSHNIKOVA N, DUBOULE D. Epigenetic temporal control of mouse Hox genes in vivo. Science 2009; 324:1320-1323) Epigenetic effects additionally are associated with withdrawal symptoms in adult alcoholism which was shown to be associated with remodeling of chromatin in the adult brain and EtOH modulating histone deacetylase activity. (PANDEY S C, UGALE R, ZHANG H, TANG L, PRAKASH A. Brain chromatin remodeling: a novel mechanism of alcoholism. J Neurosci 2008; 28:3729-37)

EtOH potentiates the Wnt/β-catenin inhibition of early cardiogenesis by suppressing expression of two cardiac inducing molecules, Hex and Isl-1. These genes are normally activated when canonical Wnt signaling is inhibited by Wnt antagonists. There is an intersection between Wnt/β-catenin signaling, EtOH, and folate metabolism. Folate tips the balance toward the differentiated state, which includes formation of the important methyl group donor, S-adenosylmethionine (SAM).

In summary, exposure of pregnant mice similarly during gastrulation on ED 6.75 to an accepted binge-drinking dose of EtOH (i.e. two i.p. injections of 2.9 g/kg of body weight, administered 3 hrs apart) on ED 6.75 (morning of the vaginal plug is ED 0.5) induced atrioventricular and semilunar valve defects, as determined noninvasively by echocardiography on ED 15.5. In the mouse after high EtOH exposure on ED 6.75, FA (10.5 mg/per 25 g mouse) supplementation or FA in combination with myo-Inositol provided in the mouse chow beginning with the morning of the vaginal plug, resulted in normal valve development (100%) on ED 15.5 as assessed by echocardiography. Folate supplementation at a high dose, or in combination with myo-inositol, prevents alcohol potentiation of Wnt/β-catenin signaling allowing normal gene activation and cardiogenesis.

Example III

Combination of Folate and Inositol for Wound Healing

The inventors have shown that the combination of folate and inositol can ameliorate chronic wound development. It has been reported that a lack of understanding of the molecular mechanisms and pathogenesis of impaired healing in chronic wounds, as for example of the epidemis, is a serious health issue that contributes to limb amputations and mortality (Stojadinovic et al., 2005). The stabilization of nuclear β-catenin inhibited wound healing and keratinocyte migration and altered their differentiation by blocking epidermal growth factor response. The fact that a high level of nuclear β-catenin is involved in an inhibition of epidermal epithelialization indicates that potentiation of canonical Wnt signaling relates to the inhibition and prevents healing thus allowing chronic ulcers to form.

Wound healing is a complex process of tissue repair that involves a number of cellular and molecular processes. Healing efficiency of epithelial damage is critical to wound repair. β-catenin, an important molecular intermediary in the canonical Wnt signaling pathway is a recognized factor in the pathogenic impairment of wound healing. The inventors discovered that similar factors involving the canonical Wnt pathway are involved both in the induction of heart defects during early embryonic development as well as in wound healing efficiency. In the gastrulating embryo, exposure to either Li or elevated homocysteine potentiates Wnt/β-catenin signaling during specification of the epithelial compartment formation that results in congenital heart defects. The timing of exposure relative to the cardiac precursor population is a factor in severity of the induced congenital defects.

cally administered to the wound directly with an inert vanishing cream (provided by Carrollwood Pharmacy) as the vehicle of administration or also in combination with an orally administered dietary folic acid supplement. Doses are provided in Table 8.

TABLE 8

| Substance (list all substances including vehicle/control) | Species (administered to) | Dose/Volume/Route (3.0 mg/kg bw/0.1 ml/ i.p.) | Interval (1x, eod, ev $3^{rd}$ day) | Duration (5 weeks) |
|---|---|---|---|---|
| 1. Folic acid (FA) in vanishing cream | Mouse | 75 μm applied topically in inert cream | daily | 15 days |
| 2. FA/Myo-inositol in vanishing cream | Mouse | FA (above): Myo-inositol as 0.8 mM. Applied topically in inert cream | daily | 15 days |
| 3. Topical inert vanishing cream | Mouse | Vehicle only/topical application to cover wound area | daily | 15 days |

The inventors have demonstrated the reversal of congenital defects formation with appropriately timed administration of folic acid or of a combination of folic acid and myo-inositol. The prophylactic efficiency of folate was greatly enhanced with myo-inositol (Han et al., 2009). As chronic wound development is similarly associated with enhanced Wnt/β-catenin signaling, administering folic acid and myo-inositol precludes adverse molecular effects during wound healing and enhances the healing process. Specifically, a combination of folate and inositol is effective in suppressing the effects of the nuclear β-catenin presence in the epidermis thus allowing for the acceleration of healing. Also, it was shown that expression of fibronectin protein, an extracellular matrix molecule shown to be important in cell migration and wound healing, was upregulated in the wound area by the folate/myo-inositol combination. Fibronectin up-regulation is an important factor in the healing process and for normal tissue organization.

The combination of FA and inositol can be administered through injection or oral intake to reach higher serum levels of folate/inositol, and/or through formulation of a topical application (as a gel or cream) applied immediately after wounding occurs to prevent chronic wounds from forming and accelerate healing of the epidermis. The higher serum levels of folate/inositol given prior to wounding did not seem to alter the healing process which may be due to wounding removing the microcirculation to that area. These results indicate that topical applications are important with regard to wound healing. There are implications for healing internal wounds in relation to administering the molecules by gel pads or i.p. injection after an operation, for example to help prevent adhesions from developing.

Recently it was shown that Wnt/β-catenin signaling was involved in the pathogenesis of impaired wound healing (Stojadinovic et al., 2005). Given that FA can rescue Wnt/13-catenin signaling in the embryo, the effects of folic acid (FA) administered alone or in combination with myo-inositol, were evaluated on wound healing in appropriately treated mice and on cell migration effects in cell cultures. It was found that FA alone or FA administered concomitantly with inositol (for example, as a cream) early in wounding, can counteract adverse cellular effects of β-catenin potentiation to aid in the healing process and to prevent chronic wounds from developing.

For the mouse studies the animals were divided by random assignment into experimental groups, using both sexes. Folic acid and folic acid/myo-inositol in combination were topi- Dietary Supplementation:

Some of the animals were placed on a higher folate diet (10 mg/kg as empirically determined from previous studies to reverse Wnt effects in embryos), one week prior to wounding. The control animals were maintained on normal animal chow containing 3.3 mg/kg FA to maintain health of the animals. After wounding, animals were housed separately and maintained on their respective folate diets. The animals were maintained in cages that were wood chip free on a dust free base for the first several days, to prevent bedding and bedding dust from getting into the freshly made wounds to lessen chances of infection.

Surgery:

A preemptive analgesic agent was used as required by IACUC to prevent wind-up and to reduce postoperative pain prior to the first surgical incision. Because of the duration of analgesia ketoprofen was provided and administered at the mouse dose rate of 10 mg/kg body weight, subcutaneously.

After the animals were anesthetized, the hair on the dorsal area of the animal was clipped and depilated (Nair, Church & Dwight Co., Princeton, N.J.) so that there is enough border area to prevent fur from contaminating the incision site. The surgical site was scrubbed at least twice with a germicidal scrub, being careful to scrub from the center of the site toward the periphery. The site was then wiped with 70% alcohol and painted with dilute, tamed iodine solution. The area was draped with sterile drapes (Bioclusive®) to prevent stray fur from entering the surgical field. The animal was placed on a temperature controlled thermal pad to maintain its normal body temperature during the wounding procedure.

The animals were anesthetized using isoflurane inhalation. One 3-mm excisional circular wound was made using a dermal biopsy punch, followed by application of the experimental or control topical cream on the wound. The excised area remained uncovered and healing was closely monitored daily until wound was closed. At day 15 after wounding, the animal was euthanized.

As required the mice were provided post-operative analgesic ketoprofen agent coverage for the first 24 hours after surgery. Topical application of wound cream, experimental or control, was applied each morning, and animals were maintained on their respective diets until day 15 post-surgery. No wound infection was noted after the procedure.

Animals were euthanized and dorsum skin specimens were harvested at different postwounding days (PWD) (1, 2, 5, 7, and 15). The results are based on duplicate samples; a male and female mouse treated identically the same.

It was observed all the wounds had healed by 7 days. The data shown is with respect to day 2 after wounding; therefore, it is approximately a mid-healing stage. For cellular effects of the topical creams, the cells were immunostained for fibronectin (FN) and for β-catenin. Fibronectin is an extracellular matrix molecule known to be important in wound healing and in epithelialization. β-catenin is an important intermediary of canonical Wnt signaling and is important in cell adhesion because it forms a bridge between the cadherins (E-, N-, and P-cadherin) and alpha-catenin in the cytoskeleton.

There appeared to be no differences in healing with respect to gender or with dietary supplementation of folic acid. By direct observation, it appeared the wounds treated topically with FA/myo-inositol containing cream had decreased redness beginning with the end of day 1 post-wounding (PWD 1) when comparing with control cream or FA only cream. There were, however, no dramatic differences in the external characteristics of the wound in any of the treatment classes.

Figure 22:
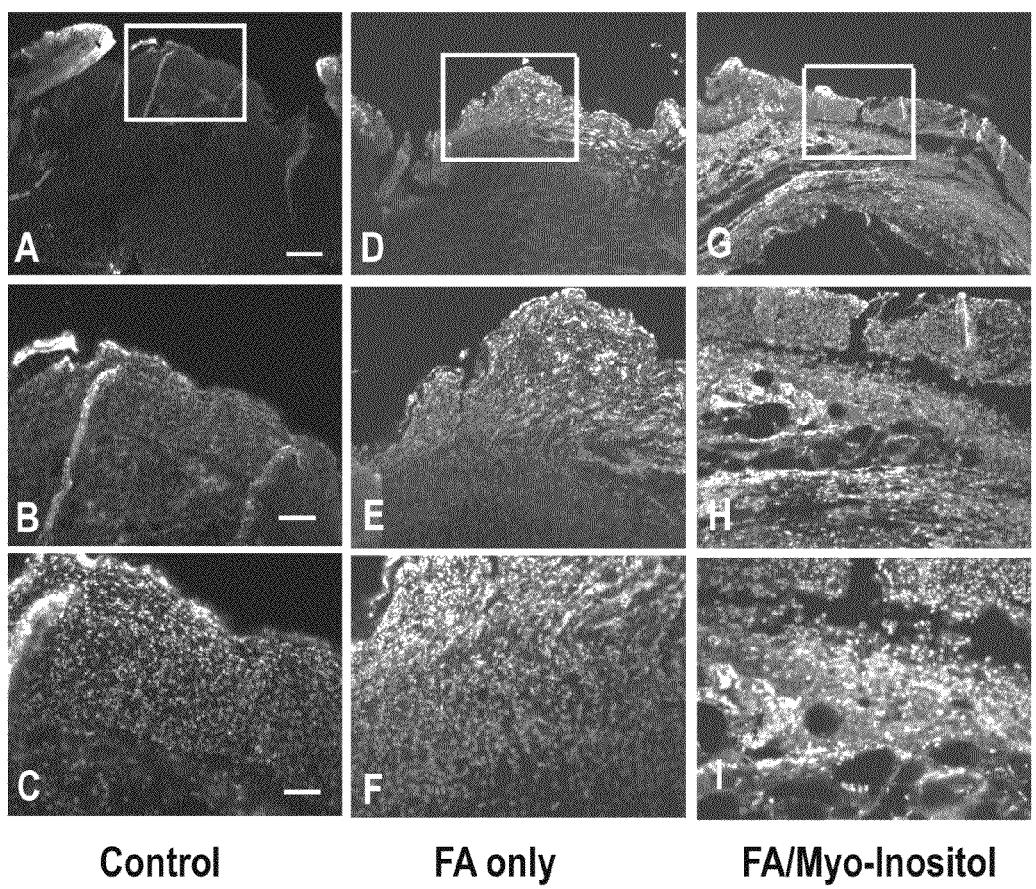
FIGS. 22A-I are a series of images illustrating the immunolocalization of FN in the center of the wound area of 6-week mouse dorsum area. The boxed-in region on PWD 2 is shown for each topical treatment at three magnifications. Top row, bar=993 μm; middle row, 399 μm; bottom row, 199 μm. Control wound area with topical application of inert cream (A-C) shows low level of FN. (D-F) Topical cream with FA supplementation shows a slight increase in FN localization above control. (G-I) Combination topical cream with FA and myo-inositol displays robust FN localization.
Figure 23:
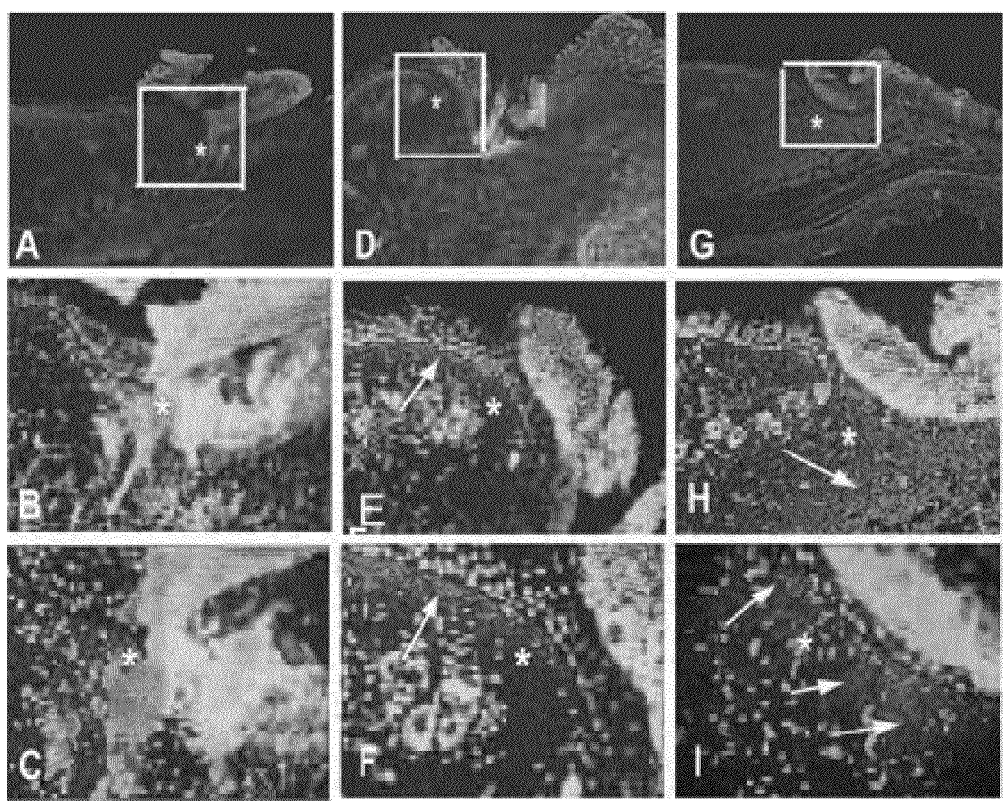
FIGS. 23A-I are a series of images illustrating the immunolocalization of FN in the edge of the wound area of the same 6-week mouse dorsum area as in FIG. 22. The boxed-in region on PWD 2 is shown for each topical treatment at three magnifications. Top row, bar=993 μm; middle row, 399 μm; bottom row, 199 μm. Control wound area with topical application of inert cream (A-C) shows low level of FN. Topical cream with FA supplementation shows a slight increase in FN localization above control (D-F). (G-I) Combination topical cream with FA and myo-inositol shows a high level and a wider field of FN expression and more normal tissue organization. Asterisks are for position information.

A square area around the central wound was removed on each specified post-wounding day (day 1, 2, 5, 7 and 15). The area was rinsed with PBS and fixed in 4% PFA in PBS and processed for paraffin sectioning. The wound areas (edge of the wound and middle of the wound area) for the various treatment creams (without dietary FA) are shown in FIGS. 22 and 23 for PWD 2. After sectioning, the tissues were immunostained for fibronectin (FIGS. 22 and 23). Although no gender difference was noted, only male skin specimens are shown to maintain uniformity for comparison (FIG. 22). The center of the wound is depicted in FIG. 22 while the edge of the wound is depicted in FIG. 23.

Figure 24:
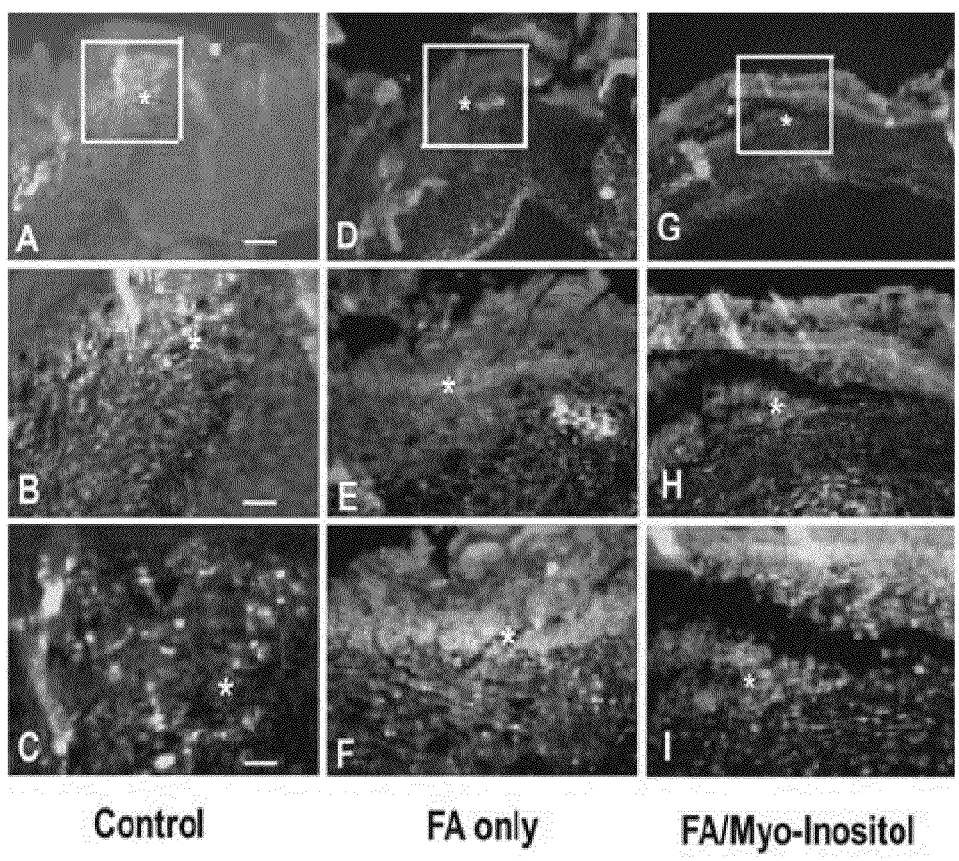
FIGS. 24A-I are a series of images illustrating the immunolocalization of 13-catenin in the center of the wound area of a 6-week mouse dorsum area. The boxed-in region on PWD 2 is shown for each topical treatment at three magnifications. Top row, bar=993 μm; middle row, 399 μm; bottom row, 199 μm. Control wound area with topical application of inert cream (A-C) shows a less organized pattern of β-catenin localization in dermal region. (D-F) Topical cream with FA supplementation shows an increase in β-catenin localization above control and a more finite expression in suprabasal epithelial layer. (G-I) Combination topical cream with FA and myo-inositol displays similar β-catenin localization as with FA alone.
Figure 25:
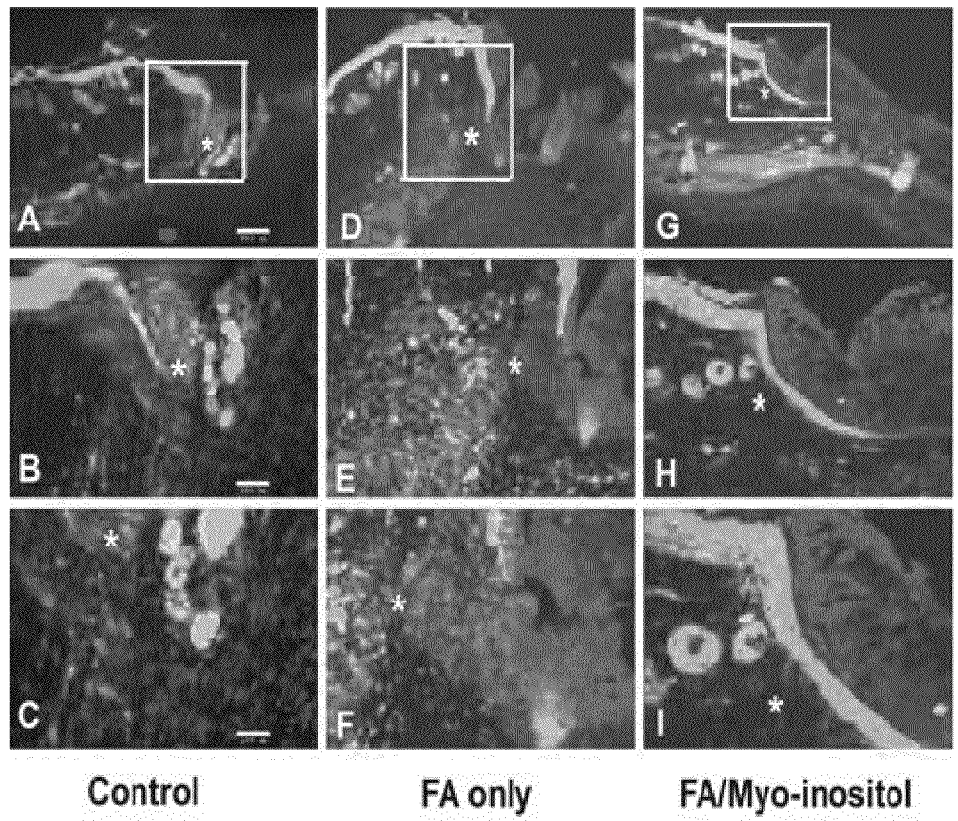
FIGS. 25A-I are a series of images illustrating the immunolocalization of β-catenin in the edge of the wound area of 6-week mouse dorsum area. The boxed-in region on PWD 2 is shown for each topical treatment at three magnifications. Top row, bar=993 μm; middle row, 399 μm; bottom row, 199 μm. Control wound area with topical application of inert cream (A-C) shows a high level of β-catenin expression in the normal skin epithelium, but low level in dermal layer. (D-F) Topical cream with FA supplementation shows an increase in β-catenin localization above control in the dermal region adjacent to the wound. (G-I) Combination topical cream with FA and myo-inositol shows a control high level of β-catenin expression in the skin epithelium and this now extends further into the healing area (see H).

As observed in FIGS. 22 and 23, the combination FA/myo-inositol cream induced the highest expression level of fibronectin (FN). FA is known to accelerate wound closure. The combination FA/myo-inositol cream also appears to maintain tissue integrity, as exemplified by the expression of normal skin architecture after wounding (FIGS. 22G-I). The same wound areas were then immunostained for β-catenin expression. The localization patterns are shown in FIGS. 24 and 25.

The above results on fibronectin and β-catenin localization taken together suggest that the combination FA/myo-inositol cream accelerates the healing process, by upregulating the extracellular matrix molecule as fibronectin (FN) that enhances cell migration into the wound area. The combination cream also enhances normal cell organization underneath the wound area. An elevation of β-catenin is noted in the dermal region of the wound area, both with FA alone and with the FA/myo-inositol combination.

Based on experiments using embryos, FA protection of normal processes involves epigenetic modulation of a Wnt antagonist by DNA methylation, as well as modulating enzymes in one-carbon metabolism based on microarray data (data not shown). Myo-inositol is associated with phosphatidylinositol signaling in the cytoplasm (Han et al., 2009). Together FA and myo-inositol act in an additive/synergistic manner at different levels of cell regulation.

Cell Culture Wound Model:

In previous studies by the inventors analyzing the effects of lithium and the metabolite homocysteine (HCy) on early heart development, the results were similar. Both factors inhibited Wnt/β-catenin—mediated gene expression during induction stages of cardiogenesis. The inventors have demonstrated that Li directly potentiates canonical Wnt signaling by inhibiting glycogen-synthase kinase-3 and thus affecting cardiogenesis (Manisastry et al., 2006; Chen et al., 2008). Folate protects the embryo from these adverse effects (Han et al., 2009). It was also noted that normal placental development was adversely affected by Li and HCy. A human trophoblast cell line, HTR-8/SVneo cells, was used to determine whether Li or HCy affect the migration of these cells in vitro and whether FA or FA/myo-inositol would protect the cells from adverse effects of the two cardiac teratogens.

Figure 26:
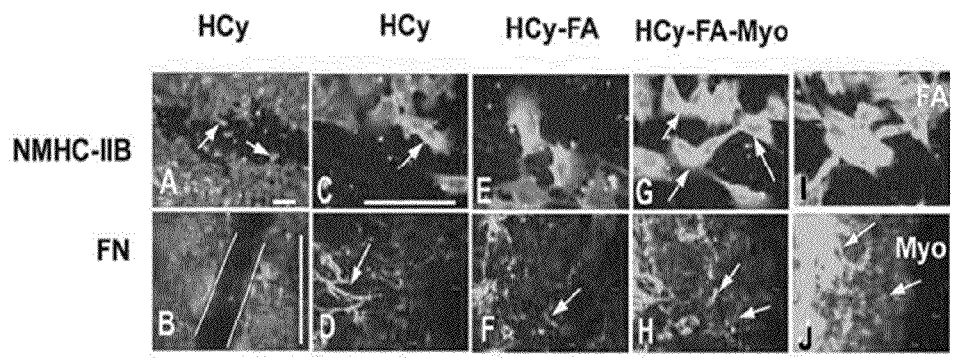
FIGS. 26A-J are a series of images depicting an in vitro wound assay addressing the protective effects of FA and FA/myo-inositol on human trophoblast HTR-8 cell migration. Different magnifications are shown A (mag bar=100 μm) and B (horizontal mag bar=1000 μm) and for C-J (mag bar=100 μm). Top row shows NMHC-IIB localization; bottom row, FN. Columns depict the various treatments.

HCy exposure experiments were conducted. The inventors immunostained for nonmuscle myosin heavy chain-IIB (NMHC-IIB), an important cytoskeletal molecule in fibroblast cell migration (Lo et al., 2004), and for fibronectin (FN) synthesis, the extracellular matrix glycoprotein that is known also to facilitate cell migration (Linask and Lash, 1986; Linask and Lash, 1988a; Linask and Lash, 1988b; Linask and Lash, 1990). The HTR-8 cells were allowed to reach confluency and then a "wound" line was made in the middle of the culture by scraping across the center of the culture dish with a rubber policeman. Cell migration was followed as the HTR-8 cells closed the wound area. In FIG. 26, the first column (A and B) shows lower magnifications of the wound area. The wound edges are depicted by a white line in B. In panel A, it can be seen that the wound area is smaller. Administration of a combination of FA/myo-inositol, FA alone or myo-inositol alone, enhanced the expression of NMHC-IIB and FN to facilitate cell migration. However the administration of the combination of FA and myo-inositol elicited an additive/synergistic effect similar to the mouse wound model.

Folate in combination with myo-inositol provides the greatest protection in an additive/synergistic manner against adverse Wnt/β-catenin-mediated effects on cell processes relating to cell differentiation, proliferation, and migration and that also relate to wound healing.

REFERENCES

Ai, D., Fu, X., Wang, J., Lu, M. F., Chen, L., Baldini, A., Klein, W. H. and Martin, J. F. (2007). Canonical Wnt signaling functions in second heart field to promote right ventricular growth. Proc Natl Acad Sci USA 104, 9319-9324.

Alvarez-Medina, R., Cayuso, J., Okubo, T., Takada, S. and Marti, E. (2008). Wnt canonical pathway restricts graded Shh/Gli patterning activity through the regulation of Gli3 expression. Development 135, 237-47.

Belmaker, R. H., Agam, G., van Calker, D., Richards, M. H. and Kofman, O. (1998). Behavioral reversal of lithium effects by four inositol isomers correlates perfectly with biochemical effects on the PI cycle. Neuropsychopharmacology 19, 220-232.

Boot, M. J., Steegers-Theunissen, R. P., Poelmann, R. E., van Iperen, L. and Gittenberger-de Groot, A. C. (2004). Cardiac outflow tract malformations in chick embryos exposed to homocysteine. Cardiovasc Res 64, 365-73.

Cai, C. L., Liang, X., Shi, Y., Chu, P. H., Pfaff, S. L., Chen, J. and Evans, S. (2003). Isl1 identifies a cardiac progenitor population that proliferates prior to differentiation and contributes a majority of cells to the heart. Dev Cell 5, 877-89.

Chen, J., Han, M., Manisastry, S. M., Trotta, P., Serrano, M. C., Huhta, J. C. and Linask, K. K. (2008). Molecular effects of lithium exposure during mouse and chick gastrulation and subsequent valve dysmorphogenesis. Birth Defects Res A Clin Mol Teratol 82, 508-518.

Clevers, H. (2006). Wnt/B-catenin signaling in development and disease. Cell 127, 469-480.

Cohen, E. D., Wang, Z., Lepore, J. J., Lu, M. M., Taketo, M. M., Epstein, D. J. and Morrisey, E. E. (2007). Wnt/β- catenin signaling promotes expansion of Isl-1-positive cardiac progenitor cells through regulation of FGF signaling. J Clin Invest 117, 1794-804.

Cohen, L. S., Friedman, J. M., Jefferson, J. W., Johnson, E. M. and Weiner, M. L. (1994). A reevaluation of risk of in utero exposure to lithium. Jama 271, 146-50.

Corstius, H., Zimanyi, M. A., Maka, N., Herath, T., Thomas, W., Van der Laarse, A., Wreford, N. G. and M. J., B. (2005). Effect of intrauterine growth restriction on the number of cardiomyocytes in rat hearts. Pediatr Res 57, 796-800.

Csepregi, A., Rocken, C., Hoffmann, J., Gu, P., Saliger, S., Muller, O, Schneider-Stock, R., Kutzner, N., Roessner, A., Malfertheiner, P. et al. (2007). APC promoter methylation and protein expression in hepatocellular carcinoma. J Cancer Res Clin Oncol.

Darnell, D. K. and Schoenwolf, G. C. (2000). Culture of Avian Embryos. In Developmental Biology Protocols, vol. 1 (ed. R. S. Tuan and C. W. Lo), pp. 31-38. Totowa, N.J.: Humana Press.

Ernest, S., Carter, M., Shao, H., Hosack, A., Lerner, N., Colmenares, C., Rosenblatt, D. S., Pao, Y. H., Ross, M. E. and Nadeau, J. H. (2006). Parallel changes in metabolite and expression profiles in crooked-tail mutant and folate-reduced wild-type mice. Hum Mol Genet 15, 3387-93.

Foley, A. and Mercola, M. (2004). Heart induction: embryology to cardiomyocyte regeneration. Trends Cardiovasc Med 14, 121-5.

Foley, A. C. and Mercola, M. (2005). Heart induction by Wnt antagonists depends on the homeodomain transcription factor Hex. Genes Dev 19, 387-96.

Gao, Y. and Wang, H. Y. (2007). Inositol pentakisphosphate mediates Wnt/13-catenin signaling. J. Biol. Chem 282, 26490-26502.

Garcia-Castro, M. I., Marcelle, C. and Bronner-Fraser, M. (2002). Ectodermal Wnt function as a neural crest inducer. Science 297, 848-51.

Gould, T. and Manji, H. (2005). Glycogen synthase kinase-3: a putative molecular target for lithium memetic drugs. *Neuropsychopharmacology* 30, 1223-1237.

Gui, Y. H., Linask, K. K., Khowsathit, P. and Huhta, J. C. (1996). Doppler Echocardiography of Normal and Abnormal Embryonic Mouse Heart. Ped. Res. 40, 633-642.

Han M, Serrano M, Lastra-Vicente R, Brinez P, Acharya G, Huhta J, Chen R, Linask K. 2009. Folate rescues lithium-, homocysteine-, and Wnt3A-induced vertebrate cardiac anomalies. Dis Models Mech 2:467-468.

Hamburger, V. and Hamilton, H. L. (1951). A series of normal stages in the development of the chick embryo. J. Morphol. 88, 49-92.

Hurlstone, A. F., Haramis, A. P., Wienholds, E., Begthel, H., Korving, J., Van Eeden, F., Cuppen, E., Zivkovic, D., Plasterk, R. H. and Clevers, H. (2003). The Wnt/β-catenin pathway regulates cardiac valve formation. Nature 425, 633-7.

Iqbal, M. and Mahmud, S. (2001). The effects of lithium, valproic acid, and carbamazepine during pregnancy and lactation. J. Toxicol. Clini Toxicol. 39, 381-392.

Jacobson, S., Ceolin, L., Kaur, P., Pastuszak, A., Einarson, T., Koren, G., Jones, K., Johnson, K. S., D., Donnenfeld, A. E., Rieder, M. and Santelli, R. (1992). Prospective multicentre study of pregnancy outcome after lithium exposure during first trimester. Lancet 339, 530-533.

Kamudhamas, A., Pang, L., Smith, S. D., Sadovsky, Y. and Nelson, D. M. (2004). Homocysteine thiolactone induces apoptosis in cultured human trophoblasts: A mechanism for homocysteine-mediated placental dysfunction. Am J. Obstet. Gynecol. 191, 563-571.

Klein, P. S. and Melton, D. A. (1996). A molecular mechanism for the effect of lithium on development. Proc. Natl. Acad. Sci. U.S.A. 93, 8455-8459.

Kwon, C., Arnold, J., Hsiao, E. C., Taketo, M. M., Conklin, B. R. and Srivastava, D. (2007). Canonical Wnt signaling is a positive regulator of mammalian cardiac progenitors. Proc Natl Acad Sci., USA 104, 10894-10899.

Lin, L., Cui, L., Zhou, W., Dufort, D., Zhang, X., Cai, C. L., Bu, L., Yang, L., Martin, J., Kemler, R. et al. (2007). B-catenin directly regulates Islet1 expression in cardiovascular progenitors and is required for multiple aspects of cardiogenesis. Proc Natl Acad Sci USA 104, 9313-8.

Linask, K. K., Han, M. D., Artman, M. and Ludwig, C. A. (2001). Sodium-calcium exchanger (NCX-1) and calcium modulation. NCX protein expression patterns and regulation of early heart development. Dev. Dynamics 221, 249-264.

Linask, K. K., Knudsen, K. A. and Gui, Y. H. (1997). N-Cadherin-Catenin Interaction: Necessary component of cardiac cell compartmentalization during early vertebrate heart development. Dev. Biol. 185, 148-164.

Linask K K, Lash J W. 1986. Precardiac cell migration: Fibronectin localization at mesoderm-endoderm interface during directional movement. Dev. Biol. 114:87-101.

Linask K K, Lash J W. 1988a. A role for fibronectin in the migration of avian precardiac cells. I. Dose dependent effects of fibronectin antibody. Dev. Biol. 129:315-323.

Linask K K, Lash J W. 1988b. A role for fibronectin in the migration of avian precardiac cells. II. Rotation of the heart-forming region during different stages and its effects. Dev. Biol. 129:324-329.

Linask K K, Lash J W. 1990. Fibronectin and integrin distribution on migrating precardiac mesoderm cells. Ann. N.Y. Acad. Sci. 588:417-420.

Linask, K. K. (1992). N-cadherin localization in early heart development and polar expression of Na, K-ATPase, and integrin during pericardial coelom formation and epithelialization of the differentiating myocardium. *Dev. Biol.* 151, 213-224.

Lo C M, Buxton D B, Chua G C, Dembo M, Adelstein R S, Wang Y L. 2004. Nonmuscle myosin IIb is involved in the guidance of fibroblast migration. Mol Biol Cell 15:982-989.

Liu, Z., Choi, S. W., Crott, J. W., Keyes, M. K., Jang, H., Smith, D. E., Kim, M., Laird, P. W., Bronson, R. and Mason, J. B. (2007). Mild depletion of dietary folate combined with other B vitamins alters multiple components of the Wnt pathway in mouse colon. J. Nutr. 137, 2701-2708.

Louvi, A., Yoshida, M. and Grove, E. A. (2007). The derivatives of the Wnt3a lineage in the central nervous system. J Comp Neurol 504, 550-69.

Manisastry, S. M., Han, M. and Linask, K. K. (2006). Early temporal-specific responses and differential sensitivity to lithium and Wnt-3A exposure during heart development. Dev Dyn 235, 2160-74.

Mohamed, O. A., Jonnaert, M., Labelle-Dumais, C., Kuroda, K., Clarke, H. J. and Dufort, D. (2008). Uterine Wnt/β-catenin signaling is required for implantation. Proc Natl Acad Sci., USA 102, 8579-8584.

Morrison, J. L., Botting, K. J., Dyer, J. L., Williams, S. J., Thornburg, K. L. and McMillen. (2007). Restriction of placental function alters heart development in the sheep fetus. Am J. Physiol. Integr Comp. Physiol 293, R306-R313.

Ochi, H., Matsubara, K., Kusanagi, Y., Furutani, K., Katayama, T. and Ito, M. (1999). The influence of the maternal heart rate on the uterine artery pulsatility index in the pregnant ewe. Gynecol. Obstet. Invest. 47, 73-75.

Raykan, V. K., Chong, S., Champ, M. E., Cuthbert, P. C., Morgan, H. D. and Luu, K. V. (2003). Transgenerational inheritance of epigenetic states at the murine Axin (Fu) allele occurs after maternal and paternal transmission. Proc Natl Acad Sci USA 100, 2538-2543.

Rosenquist, T. H., Ratashak, S. A. and Selhub, J. (1996). Homocysteine induces congenital defects of the heart and neural tube: effect of folic acid. Proc Natl Acad Sci USA 93, 15227-32.

Schmidt, C., McGonnell, I., Allen, S. and Patel, K. (2008). The role of Wnt signalling in the development of somites and neural crest. Adv Anat Embryol Cell Biol 195, 1-64.

Schou, M., Weinstein, M. R. and Villeneuve, A. (1973). Lithium and pregnancy. I. Report from the Register of Lithium Babies. Br. Med. J. 2, 135-136.

Sierra, J., Yoshida, T., Joazeiro, C. A. and Jones, K. A. (2006). The APC tumor suppressor counteracts β-catenin activation and H3K4 methylation at Wnt target genes. Genes Dev 20, 586-600.

Snarr, B. S., Wirrig, E. E., Phelps, A. L., Trusk, T. C. and Wessels, A. (2007). A spatiotemporal evaluation of the contribution of the dorsal mesenchymal protrusion to cardiac development. Dev Dyn 236, 1287-94.

Spiegelstein, O., Mitchell, L. E., Merriweather, M. Y., Wicker, N. J., Zhang, Q., Lammer, E. J. and Finnell, R. H. (2004). Embryonic development of folate binding protein-1 (Folbp1) knockout mice: Effects of the chemical form, dose, and timing of maternal folate supplementation. Dev Dyn 231, 221-31.

Stajodinovic, O., Brem, H., Vouthounis, C., Lee, B., Fallon, J., Stallcup, M., Merchant, A., Galiano, R. D. and Tomic-Canic, M. (2005). Molecular pathogenesis of chronic wounds. *Am. J. Pathol.* 167, 59-69.

Tang, L. S., Wlodarczyk, B. J., Santillano, D. R., Miranda, R. C. and Finnell, R. H. (2004). Developmental consequences of abnormal folate transport during murine heart morphogenesis. Birth Defects Res A Clin Mol Teratol 70, 449-58.

Ueno, S., Weidinger, G., Osugi, T., Kohn, A. D., Golob, J. L., Pabon, L., Reinecke, H., Moon, R. T. and Murry, C. E. (2007). Biphasic role for Wnt/β-catenin signaling in cardiac specification in zebrafish and embryonic stem cells. Proc Natl Acad Sci USA 104, 6685-9690.

Ulloa, F. and Briscoe, J. (2007). Morphogens and the control of cell proliferation and patterning in the spinal cord. Cell Cycle 6, 2640-9.

Willert, K. and Jones, K. (2006). Wnt signaling: is the party in the nucleus? Genes Dev 20, 1394-1404.

Williams, K. T. and Schalinske, K. L. (2007). New insights into the regulation of methyl group and homocysteine metabolism. J Nutr 137, 311-4.

Wohrle, S., Wallmen, B. and Hecht, A. (2007). Differential control of Wnt target genes involves epigenetic mechanisms and selective promoter occupancy by T-cell factors. Mol Cell Biol 27, 8164-77.

Yonkers, K. A., Stowe, Z., Leibenluft, E., Cohen, L., Miller, L., Manber, R., Viguera, A., Suppes, T. and Altshuler, L. (2004). Management of bipolar disorder during pregnancy and the postpartum period. Am. J. Psychiatry 161, 608-620.

Yu, W., McDonnell, K., Taketo, M. M. and Bai, C. B. (2008). Wnt signaling determines ventral spinal cord cell fates in a time-dependent manner. Development 135, 3687-96.

Zhang, F., Phiel, C., Spece, L., Gurvich, N. and Klein, P. (2003) Inhibitory phosphorylation of glycogen synthase kinase-3 (GSK-3) in response to lithium. J. Biol. Chem. 278, 33067-33077.

Zhu, H., Wlodarczyk, B. J., Scott, M., Yu, W., Merriweather, M., Gelineau-van Waes, J., Schwartz, R. J. and Finnell, R. H. (2007). Cardiovascular abnormalities in Folr1 knockout mice and folate rescue. Birth Defects Res A Clin Mol Teratol 79, 257-68.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described, What is claimed is:

1. A method of treating a congenital cardiac defect caused by altered canonical Wnt signaling in a patient in need thereof comprising the step of administering a therapeutically effective combination of a folate compound and an inositol compound to a mother of the patient wherein the altered canonical Wnt signaling is caused by elevated homocysteine levels, exposure to lithium or exposure to alcohol during pregnancy wherein the congenital cardiac defect is selected from the group consisting of valve defects including valve regurgitation and valve dysmorphogenesis, altered myocardial thickness, outflow tract defects, cardiabifida, looping defects and ventricular defects.

2. The method of claim 1, wherein the combination of the folate compound and the inositol compound is administered to the mother after conception and through first trimester of pregnancy.

3. The method of claim 1, wherein the combination of the folate compound and the inositol compound is administered to the mother throughout the pregnancy.

4. The method of claim 1, wherein the folate compound is folic acid.

5. The method of claim 1, wherein the inositol compound is myo-inositol.

6. A method of reducing the formation of a congenital cardiac defect caused by altered canonical Wnt signaling in a patient at risk therefrom comprising the step of administering a therapeutically effective combination of a folate compound and an inositol compound to the patient wherein the altered canonical Wnt signaling is caused by elevated homocysteine levels, exposure to lithium or exposure to alcohol during pregnancy wherein the congenital cardiac defect is selected from the group consisting of valve defects including valve regurgitation and valve dysmorphogenesis, altered myocardial thickness, outflow tract defects, cardiabifida, looping defects and ventricular defects.

7. The method of claim 6, wherein the combination of the folate compound and the inositol compound is administered to the mother after conception and throughout first trimester of pregnancy.

8. The method of claim 6, wherein the combination of the folate compound and the inositol compound is administered to the mother throughout the pregnancy.

9. The method of claim 6, wherein the inositol compound is myo-inositol.

10. The method of claim 6, wherein the folate compound is folic acid.

11. A method of upregulating fibronectin in a surgical wound of a patient by administering a therapeutically effective combination consisting essentially of a folate compound and an inositol compound to a patient in need thereof.

12. The method of claim 11, wherein the folate compound is folic acid.

13. The method of claim 11, wherein the inositol compound is myo-inositol.

* * * * *